United States Patent
Babbitt et al.

(10) Patent No.: US 9,453,193 B2
(45) Date of Patent: Sep. 27, 2016

(54) SYSTEMS AND METHODS FOR DELIVERY OF GASES TO ALGAL CULTURES

(75) Inventors: Guy Robert Babbitt, Fort Collins, CO (US); Michael Ryan Buehner, Fort Collins, CO (US); David Jacob Rausen, Fort Collins, CO (US); Richard Charles Schoonover, Fort Collins, CO (US); Christopher Wayne Turner, Windsor, CO (US); Kristina Weyer-Geigel, Fort Collins, CO (US); Bryan Dennis Willson, Fort Collins, CO (US); Peter Michael Young, Fort Collins, CO (US); David Eli Sherman, Fort Collins, CO (US); Jason Charles Quinn, Fort Collins, CO (US)

(73) Assignees: COLORADO STATE UNIVERSITY RESEARCH FOUNDATION, Fort Collins, CO (US); SOLIX ALGREDIENTS, INC., Fort Collins, CO (US)

(*) Notice: Subject to any disclaimer, the term of this patent is extended or adjusted under 35 U.S.C. 154(b) by 232 days.

(21) Appl. No.: 13/257,565

(22) PCT Filed: Mar. 18, 2010

(86) PCT No.: PCT/US2010/027883
§ 371 (c)(1),
(2), (4) Date: Dec. 16, 2011

(87) PCT Pub. No.: WO2010/108049
PCT Pub. Date: Sep. 23, 2010

(65) Prior Publication Data
US 2012/0107792 A1    May 3, 2012

Related U.S. Application Data

(60) Provisional application No. 61/161,723, filed on Mar. 19, 2009.

(51) Int. Cl.
| | | |
|---|---|---|
| C12N 1/12 | (2006.01) | |
| C12M 1/00 | (2006.01) | |
| C12M 1/34 | (2006.01) | |
| C12M 1/107 | (2006.01) | |
| C12M 1/36 | (2006.01) | |

(52) U.S. Cl.
CPC ............ *C12M 21/02* (2013.01); *C12M 23/36* (2013.01); *C12M 29/24* (2013.01); *C12M 41/34* (2013.01); *C12M 41/48* (2013.01)

(58) Field of Classification Search
CPC .... C12M 21/02; C12M 23/36; C12M 29/24; C12M 41/34; C12M 41/48
USPC .......................................... 435/286.6, 296.1
See application file for complete search history.

(56) References Cited

U.S. PATENT DOCUMENTS

| | | |
|---|---|---|
| 4,272,379 A | 6/1981 | Pollock |
| 2001/0043508 A1* | 11/2001 | Zhou ............................ 366/273 |
| 2003/0059932 A1* | 3/2003 | Craigie et al. ............. 435/292.1 |
| 2004/0043481 A1 | 3/2004 | Wilson |
| 2005/0158701 A1 | 7/2005 | West |
| 2008/0160591 A1* | 7/2008 | Willson et al. ............... 435/132 |

OTHER PUBLICATIONS

Yun et al., Development of gas recycling photobioreactor system for microalgal carbon dioxide fixation. Korean Journal of Chemical Engineering, vol. 14, No. 4 (1997) pp. 297-300.*
International Search Report and Written Opinion issued in PCT/US2010/27883, mailed May 18, 2010, 13 pages.

* cited by examiner

*Primary Examiner* — Kara Johnson
(74) *Attorney, Agent, or Firm* — Faegre Baker Daniels LLP

(57) ABSTRACT

Photobioreactors according to embodiments of the present invention deliver nutrient gas intermittently to the photobioreactor media. In some embodiments, one or more gases are delivered according to a duty cycle or timing pattern. According to some embodiments, algae is grown in a photobioreactor using intermittent introduction of carbon dioxide. In other embodiments, carbon dioxide is supplied to algae grown in a photobioreactor in whole or in part from a head space above the media of the photobioreactor.

14 Claims, 42 Drawing Sheets

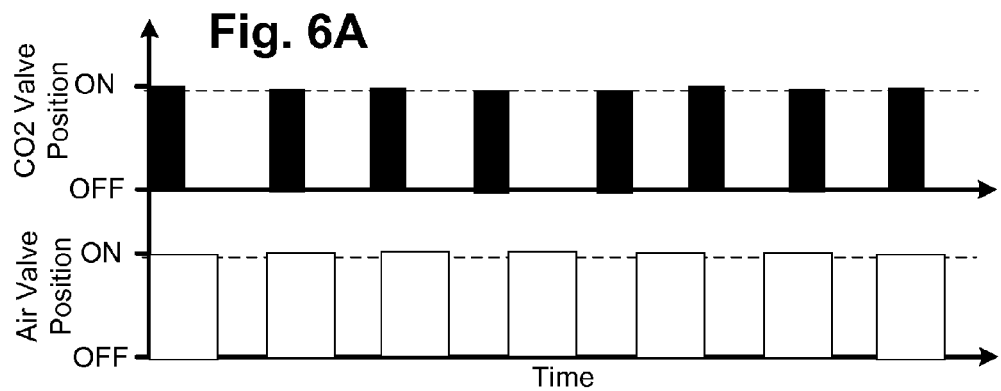
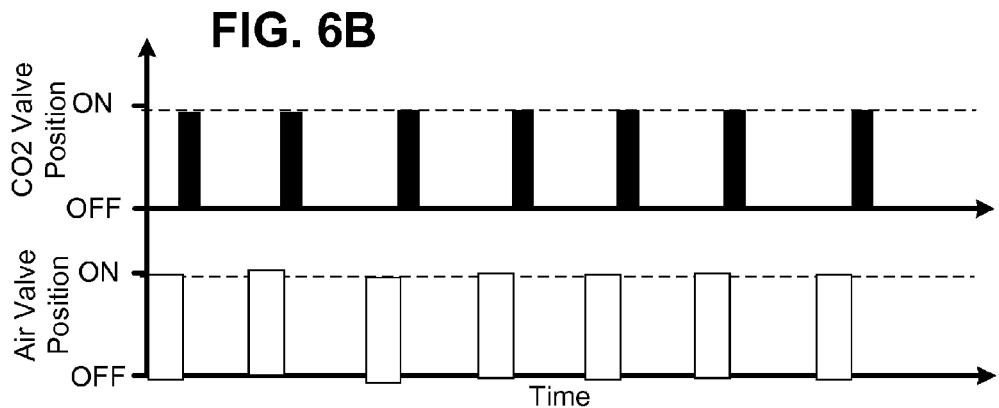
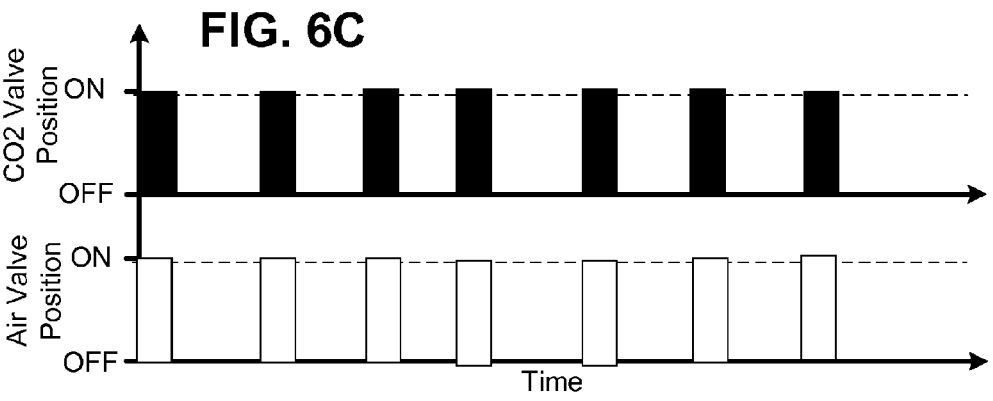

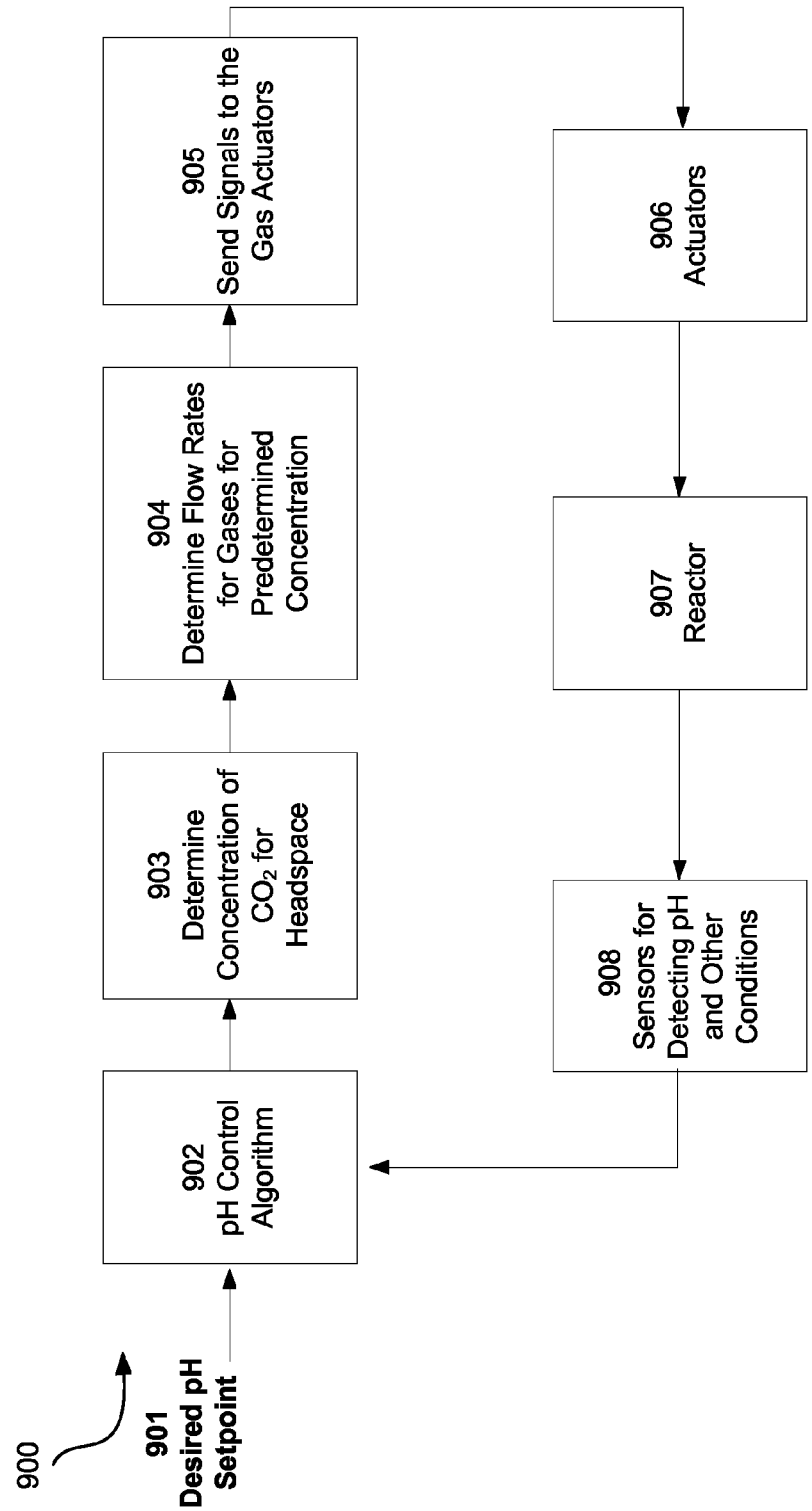

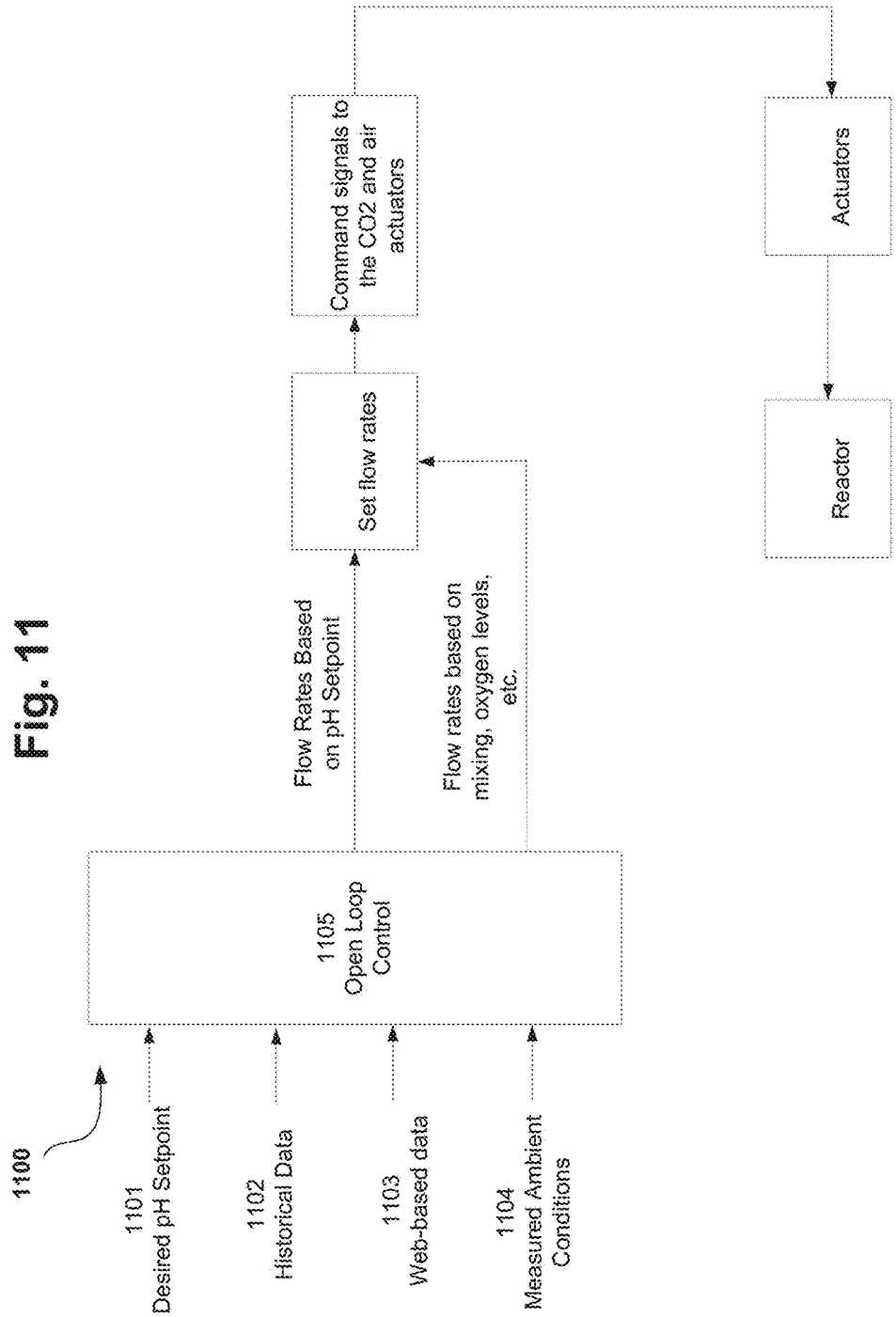

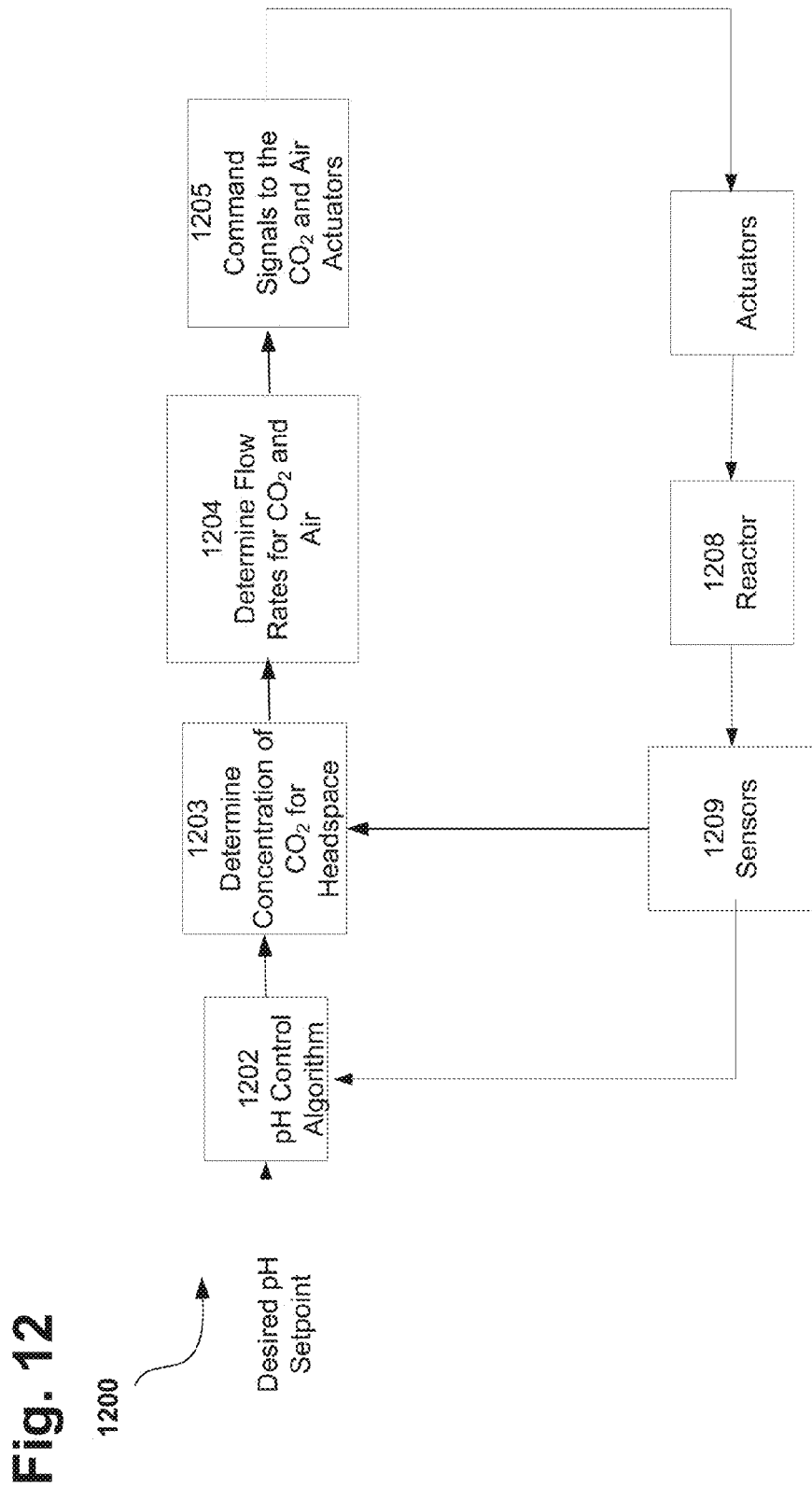

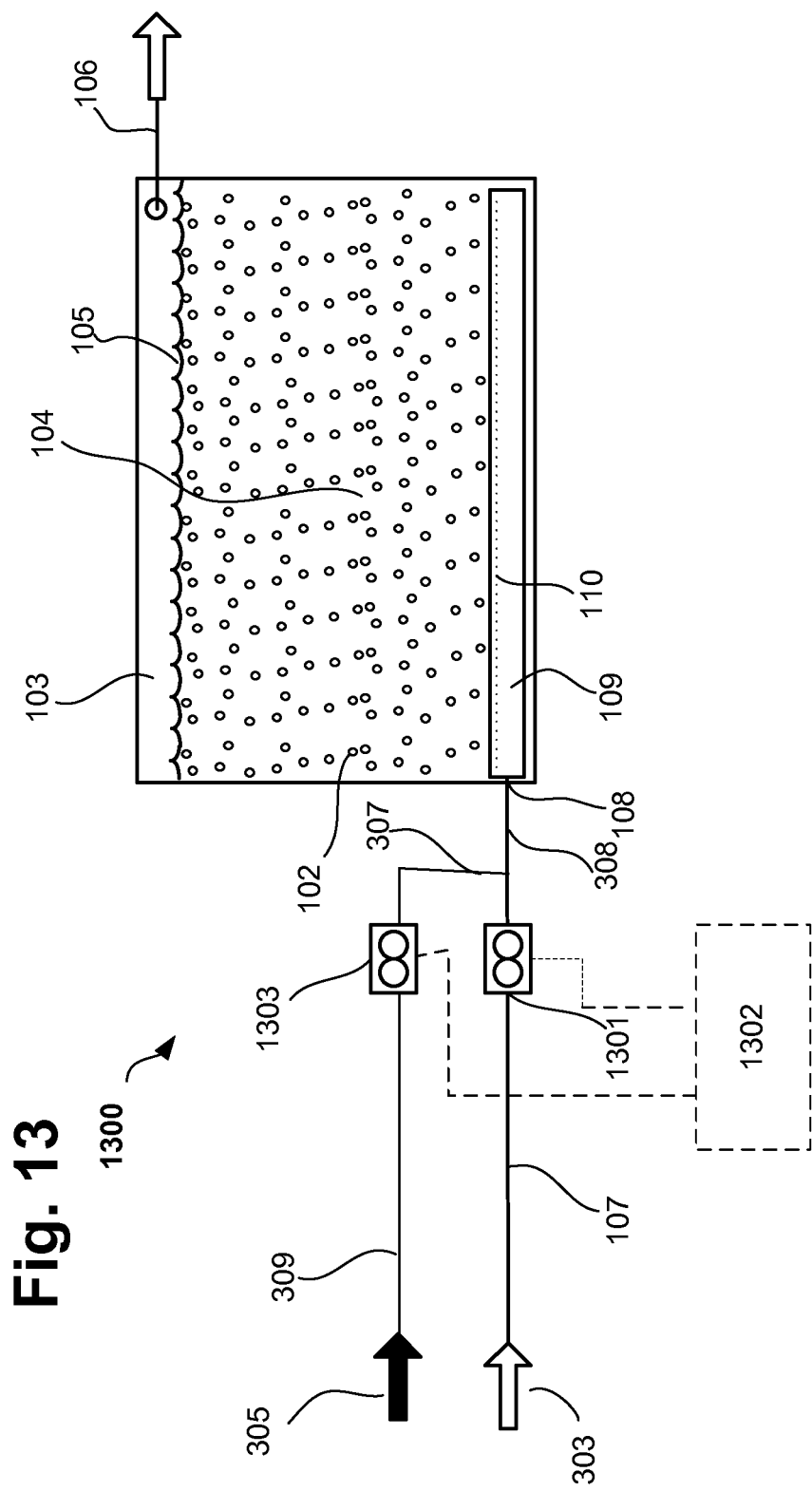

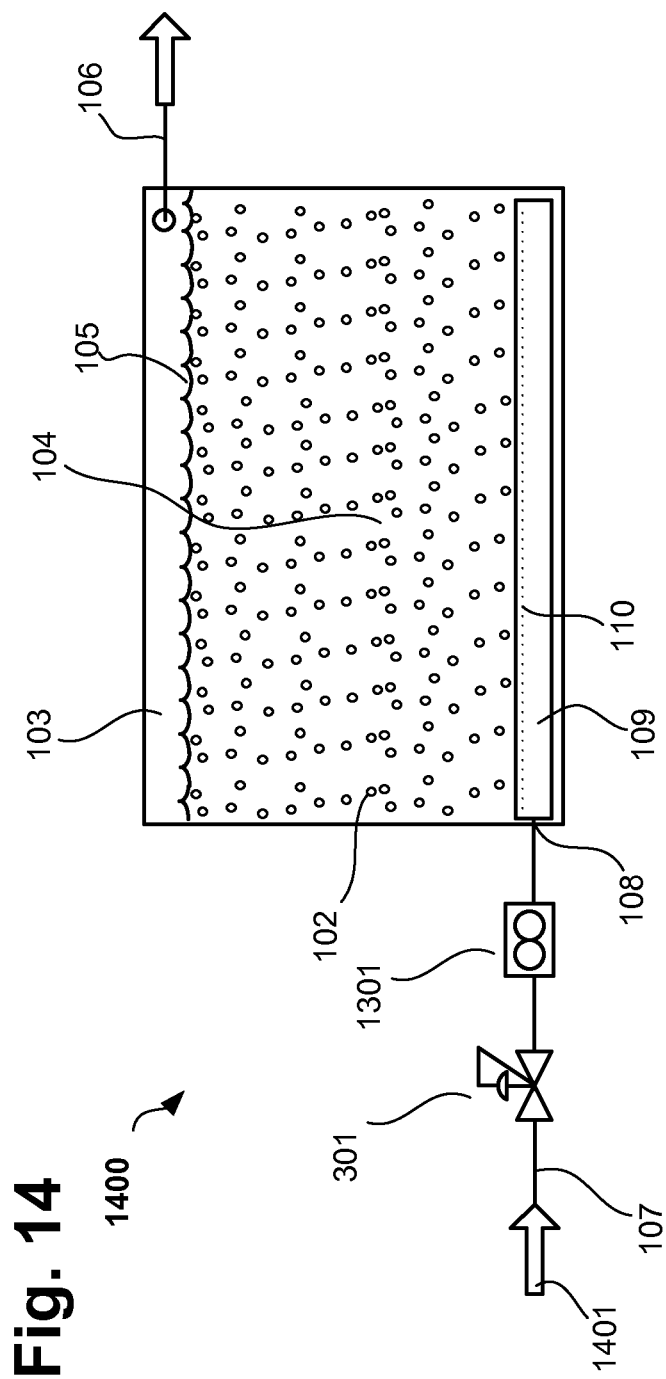

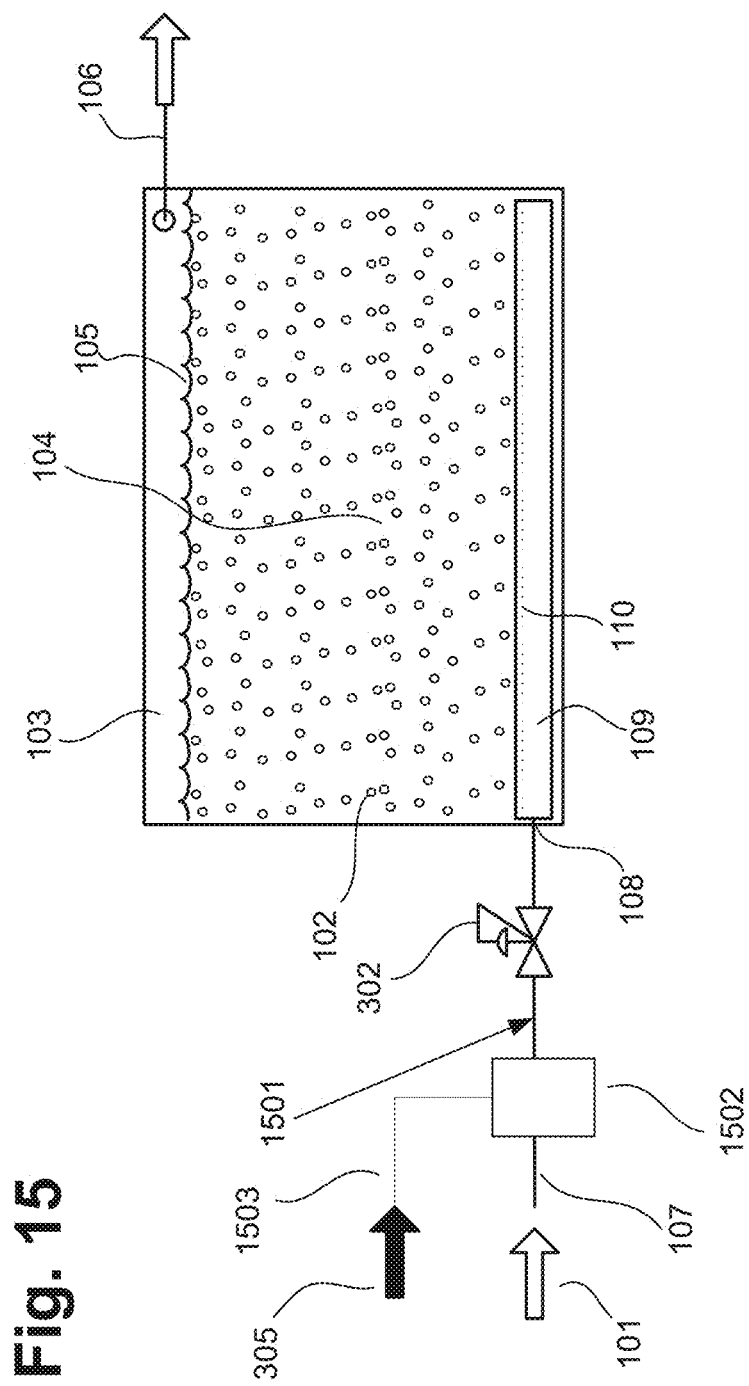

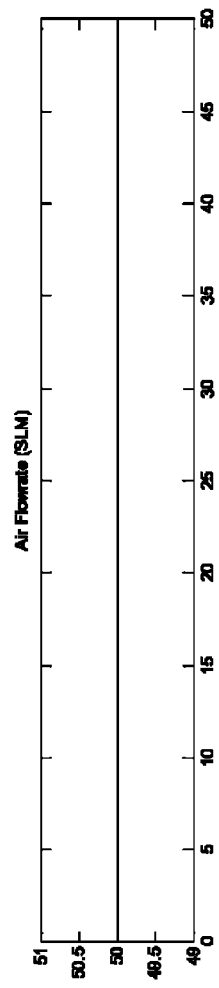
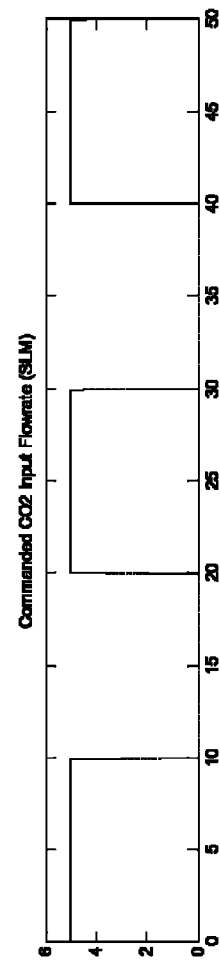
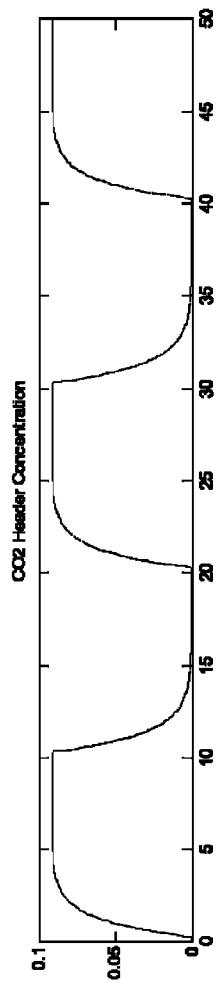

SYSTEMS AND METHODS FOR DELIVERY OF GASES TO ALGAL CULTURES

CROSS-REFERENCE TO RELATED APPLICATIONS

This application claims the benefit of U.S. Provisional Patent Application Ser. No. 61/161,723, filed on Mar. 19, 2009, which is incorporated herein by reference.

FIELD

Embodiments of the present invention relate generally to systems and methods for delivery of gases to photobioreactors, and more specifically to periodic and/or interval delivery of gases to photobioreactors.

BACKGROUND

Producing biofuels, such as biodiesel, bioethanol, and/or biogasoline, from renewable energy sources provides numerous benefits. Increasing costs, increasing difficulty of extraction, and depletion of known fossil fuel reserves help to spur the development of alternative fuel supplies. Efforts have been made to develop renewable energy fuels such as ethanol from corn grain or biodiesel from canola, rapeseed and other sources. The amount of biofuel that can be derived from food plant materials is often limited and the underlying increase in food commodity prices often negatively impacts food availability in developing countries and food prices in the developed world.

Efforts are underway to generate biofuels from non-food materials, such as cellulosic ethanol from wood pulp, corn stover or sugar cane bagasse. Algae and other photosynthetic microorganisms can provide feedstock for biofuel synthesis.

SUMMARY

Cultures of microorganisms can be grown by introducing one or more gases to the cultures for a predetermined duration, wherein the duration is no longer than ninety percent of the time during which the algae are growing and/or is intermittently delivered, according to embodiments of the present invention. Duty cycle refers to the percentage of ON time of one or more gas supplies relative to the percentage of OFF time of the one or more gas supplies.

According to certain embodiments of the present invention, free space at the top of a closed photobioreactor creates an interface between liquid media and gas that may be controlled to exchange desired gas constituents. For example, carbon dioxide or oxygen may be exchanged from the free space to the media, and dissolved gases may be transferred from the media into the free space. In addition, delivery and recovery of gases can increase growth of cultures, reduce lag time and at the same time reduce cost for growing cultures. Increased efficiency for regulating gas input can result in better growth, better control and reduced power consumption.

According to some embodiments of the present invention, one or more gases is introduced to a photobioreactor in a manner that is controlled temporally and/or spatially. In accordance with such embodiments, intermittent introduction of gases to a photobioreactor can involve sparging of one or more gases into a photobioreactor where the one or more gases are intermittently introduced. In certain embodiments, temporal intermittent introduction of gases to a photobioreactor varies by time. Other embodiments of spatial intermittent introduction of gases to a photobioreactor can relate to varying geometry of hardware, varying location of gas introduction and/or dimension of gaseous bubbles and frequency of introduction. Yet other embodiments use both such intermittent methods for introducing one or more gases to a photobioreactor. In yet other embodiments of the present invention, carbon dioxide introduced to the media can be recaptured and/or reused. These embodiments a can result in cost savings, increased robustness, better growth, better control and reduced power consumption.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 6A-6D represent exemplary patterns for introducing one or more gases to a photobioreactor, according to embodiments of the present invention.

FIG. 9 depicts a flow chart showing a method for determining carbon dioxide delivery for one or more photobioreactors, according to embodiments of the present invention.

FIG. 11 represents a flow chart illustrating a method for gas delivery in an open loop system, according to embodiments of the present invention.

FIG. 12 represents a flow chart illustrating a method for gas delivery in a closed loop system, according to embodiments of the present invention.

FIG. 13 illustrates a photobioreactor system utilizing variable gas flow rates, according to embodiments of the present invention.

FIG. 14 illustrates a photobioreactor system utilizing carbon dioxide delivery only, according to embodiments of the present invention.

FIG. 15 illustrates a photobioreactor system that operates at a constant ratio of gas delivery, according to embodiments of the present invention.

FIG. 32 illustrates an air flow rate using a dynamic modeling simulation for a photobioreactor having no diffusion dynamics, according to embodiments of the present invention.

FIG. 33 illustrates a commanded carbon dioxide input flow rate using a dynamic modeling simulation for a photobioreactor having no diffusion dynamics, according to embodiments of the present invention.

FIG. 34 illustrates a carbon dioxide header concentration using a dynamic modeling simulation for a photobioreactor having no diffusion dynamics, according to embodiments of the present invention.

Figure 1:
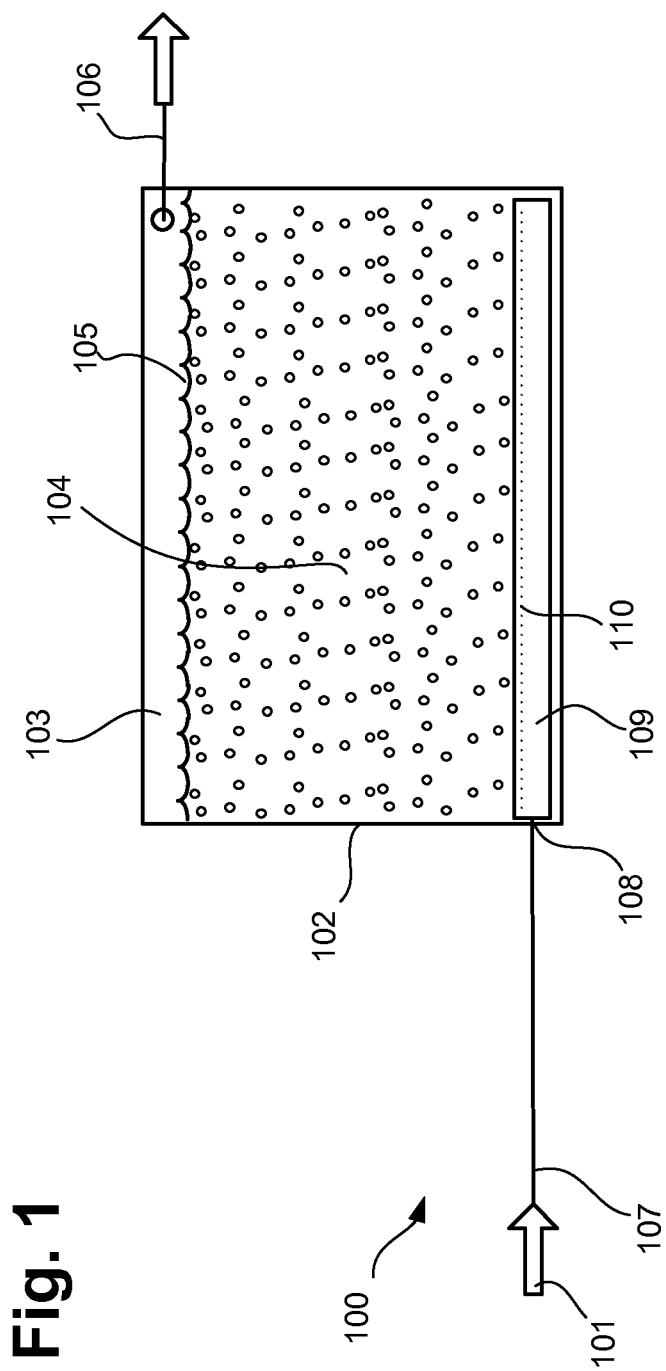
FIG. 1 illustrates a photobioreactor system utilizing a sparging system for gas delivery, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention and of the present disclosure.

DETAILED DESCRIPTION

Growing algae as a feedstock for biodiesel may involve growing the algae inside of closed bioreactors. Carbon, usually in the form of carbon dioxide ($CO_2$), is often added to the bioreactor media to support photosynthesis. Similarly, the process of photosynthesis liberates oxygen ($O_2$) which dissolves in the media. Relying on an open bioreactor exposed to ambient air in order to receive carbon dioxide from the air and vent the liberated oxygen to the air often does not yield enough carbon to support effective algae growth, due to the relatively low carbon dioxide content of air. Bubbling carbon dioxide directly into the bioreactor media may often involve a relatively low carbon dioxide absorption into the media, such that supplying the carbon dioxide often requires more energy than is produced by the algae growth. In addition, using a complex membrane contactor to promote absorption of carbon dioxide into the media often involves a relatively high expense, which also often requires a greater cost than the value of the energy produced through algae growth.

In the following sections, various exemplary systems and methods are described in order to detail various embodiments. It will be obvious to one skilled in the art that practicing the various embodiments does not require the employment of all or even some of the specific details outlined herein, but rather that times, system components and other specific details may be modified through routine experimentation.

Embodiments of the present invention include systems and methods for delivering and/or capturing various gases for growing cultures. In certain embodiments, systems and methods deliver and/or capture various gases for growing cultures in photobioreactors. Cultures can be microorganisms; for example, cultures can be algal cultures. Systems according to embodiments of the present invention feed single or multiple photobioreactors by networks designed for delivering and/or capturing various gases of the photobioreactors.

Researchers are exploring growing algae as a feedstock for biodiesel. In many designs the algae is grown inside closed reactors comprised of glass or plastic. Examples of closed system bioreactors suitable for growth of algae and other microorganisms are described in U.S. patent application Ser. No. 11/871,728, filed Oct. 12, 2007 and published on Jul. 3, 2008 as U.S. Patent Application Publication No. 2008/0160591, which is incorporated by reference herein in its entirety.

Some embodiments herein concern introducing carbon dioxide into the media, or the water in which the algae is grown, by allowing the free surface of the media to be exposed to atmospheric air. Typical air contains approximately 0.038% carbon dioxide by volume. While such a configuration is relatively easy to implement, it does not allow for much carbon to be added to the media and therefore the effectiveness of the algae growth may not be as high in such circumstances.

Photobioreactors may be used for growing algae. Algae grown in a bioreactor have various needs. For example, increased growth performance can be obtained if the concentrations of many of the system variables are be controlled. Amounts of various gases introduced to media of algal cultures were examined. In one example, carbon dioxide added to the media may directly control the productivity and/or growth of cultures of a photobioreactor system. Some photobioreactor systems deliver carbon dioxide to the media using simple sparging; often, some photobioreactor systems have poor uptake utilization which can waste gases, while others use complicated and expensive systems which are cost-prohibitive for mass production.

Algae or photosynthetic microorganisms may be grown in a photobioreactor. Microorganisms include, but are not limited to, *Nannochloropsis oculata, Nannochloropsis gaditana, Nannochloropsis salina, Tetraselmis suecica, Tetraselmis chuii, Nannochloropsis* sp., *Chlorella salina, Chlorella prototheocoides, Chlorella ellipsoidea, Dunaliella tertiolecta, Dunaliella salina, Phaeodactulum tricornutum, Botrycoccus braunii, Chlorella emersonii, Chlorella minutissima, Chlorella pyrenoidosa, Chlorella sorokiniana, Chlorella vulgaris, Chroomonas salina, Cyclotella cryptica, Cyclotella* sp., *Euglena gracilis, Gymnodinium nelsoni, Haematococcus pluvialis, Isochrvsis galbana, Monoraphidium minutum, Monoraphidium* sp., *Neochloris oleoabundans, Nitzschia laevis, Onoraphidium* sp., *Pavlova lutheri, Phaeodactylum tricornutum, Porphyridium cruentum, Scenedesmus obliquuus, Scenedesmus quadricaula Scenedesmus* sp., *Stichococcus bacillaris, Spirulina platensis,* and *Thalassiosira* sp. These cultures may be grown separately, or as combination cultures.

Embodiments of the present invention include photobioreactor systems that feature improved or optimal biomass growth, oil production, energy consumption, efficiency of carbon dioxide utilization, and/or other important metrics of operation by using systems capable of efficient cost effective delivery of various gases to bioreactors. According to some embodiments of the present invention, free surfaces of liquid-gas interfaces in a reactor are used to introduce carbon dioxide and other gases to the media. In other embodiments, gases are introduced to the photobioreactor intermittently, for example by sparging. Such processes for growing cultures can have significant power and cost savings. According to embodiments of the present invention, intermittent gas introduction includes temporally intermittent gas introduction and/or gas collection where introduction is varied with time, and/or spatially intermittent gas introduction where introduction of gas(es) varies with location within a bioreactor system.

In other embodiments, photobioreactor systems increase carbon content of water or media of a culture. For example, increasing carbon content can be accomplished by bubbling or sparging, gaseous carbon dioxide through the media or water. For example, carbon dioxide may be sparged through media either in pure form or mixed with other gases, for example, air. Bubbles formed will rise through the media and a portion of the carbon dioxide will be absorbed into the media, adding carbon to the media or water. In accordance with such embodiments, pH of the media and water can be adjusted or changed by altering the introduction of carbon dioxide with or without other gases. Typically, carbon dioxide bubbles do not have adequate time to be absorbed before reaching the surface of the media within a system. In many cases, a very small portion of the carbon dioxide is absorbed and the non-absorbed carbon dioxide is expelled through the media or water surface or vented air, resulting in relatively low uptake efficiency. Often, costs to preprocess and pump the carbon dioxide gas in such cases is relatively high.

Residence time of bubbles in media of a culture system is increased before the bubbles reach free surface. For example, carbon dioxide as bubbles may be injected at the bottom of a pipe oriented vertically with the media flowing from top to bottom, such that the average velocity of the media in the pipe is approximately the same, or slightly slower than, the velocity at which the bubbles rise. While this increases the residence time of the bubbles in the media, energy is expended in continuously pumping the fluid, thus the cost of injecting bubbles into a counterflow is often high.

FIG. 1 illustrates a schematic of a gas delivery system 100 for a photobioreactor 102 used to grow microorganisms. The reactor 102 is comprised of a film bag, and may include a gas delivery conduit 109 with perforations 110. The bioreactor 102 may be partially filled with a mixture of media and microorganisms and may have a volume of gas 103 above the free surface 105 of the media 104. The microorganisms use photosynthesis to grow in the presence of light, which is typically sunlight, but which could also be supplied by artificial sources such as an electric light. The microorganisms need a variety of nutrients to grow, one being carbon, often delivered to organisms by means of dissolving carbon dioxide into the media 104.

In certain embodiments, media 104 may include, but is not limited to, water, macro and micronutrients and, optionally, salts. If, for example, the media is intended to grow organisms that would normally grow in salt water, salts are added to the media. In certain embodiments, typical salt concentrations are on the order of 15-36 parts per thousand (ppt) but can vary depending on needs of the organism. In other embodiments, macronutrients can include, but are not limited to, nitrogen and phosphates. Macronutrient concentrations can be added on the order of about 0.05-0.05 grams/liter, according to embodiments of the present invention. Micronutrients concentrations can include, but are not limited to, trace metals such as zinc, iron and copper. Micronutrient concentrations can be added on the order of concentrations of about 20-3000 micrograms/liter, for example.

Carbon can be added to the media in many different ways. One method is to add the carbon chemically in the form of sugars (e.g. sucrose) or alcohols (e.g. ethanol). Growing microorganisms in this manner is often referred to as heterotrophic. Microorganisms grown in a photobioreactor are grown autotrophically, using carbon dioxide. Mixtatrophic growth involves providing a microorganism, for example, algae, with carbon from both carbon dioxide and other carbon sources. Embodiments of the present invention permit autotrophic and/or mixtratrophic growth of microorganisms.

In certain embodiments of the present invention, carbon dioxide is introduced through porous or non-pourous membranes that allow carbon dioxide to permeate from one side of the membrane to the media on the other side of the membrane. Utilizing membranes in conjunction with plastic film photobioreactors is outlined in detail in U.S. Patent Provisional Application No. 61/059,863 filed Jun. 9, 2008, incorporated by reference herein in its entirety.

Porous membranes have microscopic holes that allow the gas on one side of the membrane to form a bubble across the hole. This allows the liquid on the other side of the membrane to have direct contact with the gas. A difference in the partial pressure of the gas in the gas mixture and the gas in the media causes the gas in the gas mixture to diffuse from one side of the membrane to the other until the partial pressure difference reaches equilibrium. Because these interfaces between the gas and the liquid occur only where there are holes in the membrane, the diffusion rate of the gas into the media, or vice versa, on a per area basis is generally less than could be achieved with a continuous interface of gas and liquid under similar conditions.

Non-porous membranes work by allowing carbon dioxide or other gases to effectively dissolve into the membrane, then diffuse through the membrane and dissolve into the media. In certain embodiments, one porous membrane can be a silicone rubber membrane which can be effective at adding carbon dioxide to media. Like porous membranes, the diffusion rates of gases through non-porous membranes tend to be less than that for a free surface under comparable conditions.

While using membranes can be a very effective method to get carbon dioxide into the media, membranes can be expensive, difficult to handle and permeability can be less than that obtained with a pure liquid/gas interface. Furthermore, integrating membranes into photobioreactors can complicate the manufacturing process resulting in a potentially more expensive and possibly less robust product.

Figure 2:
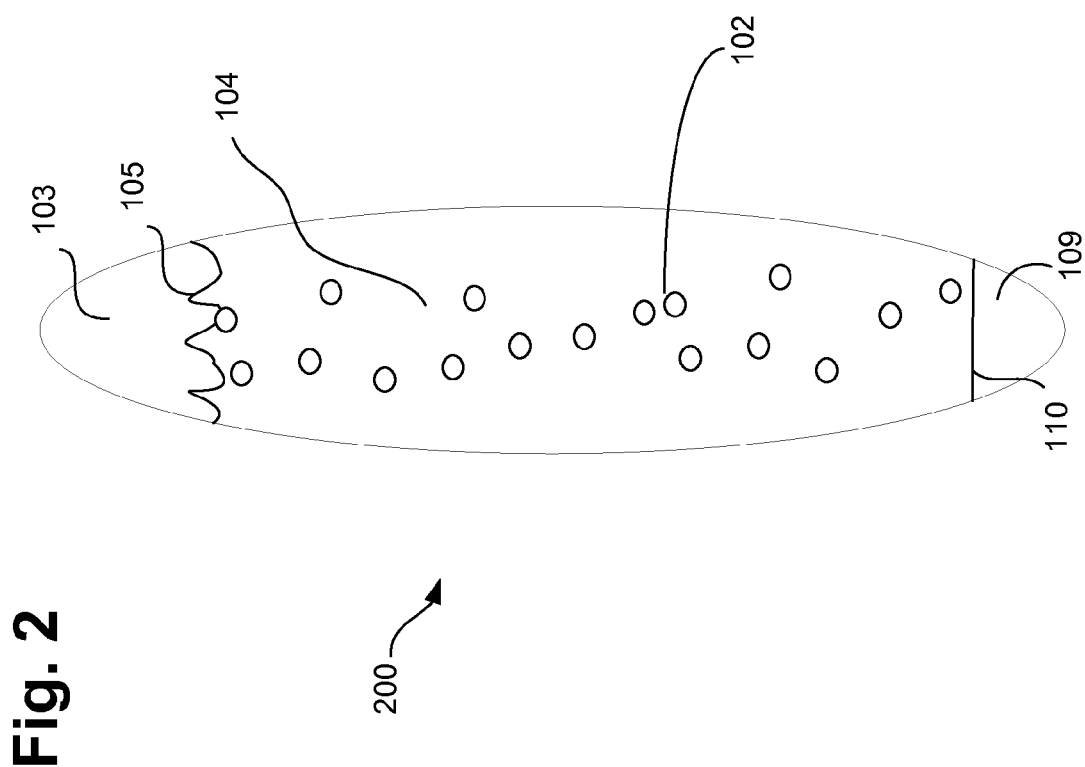
FIG. 2 illustrates a cross-sectional view of a photobioreactor system utilizing a sparging system for gas delivery, according to embodiments of the present invention.
Figure 3:
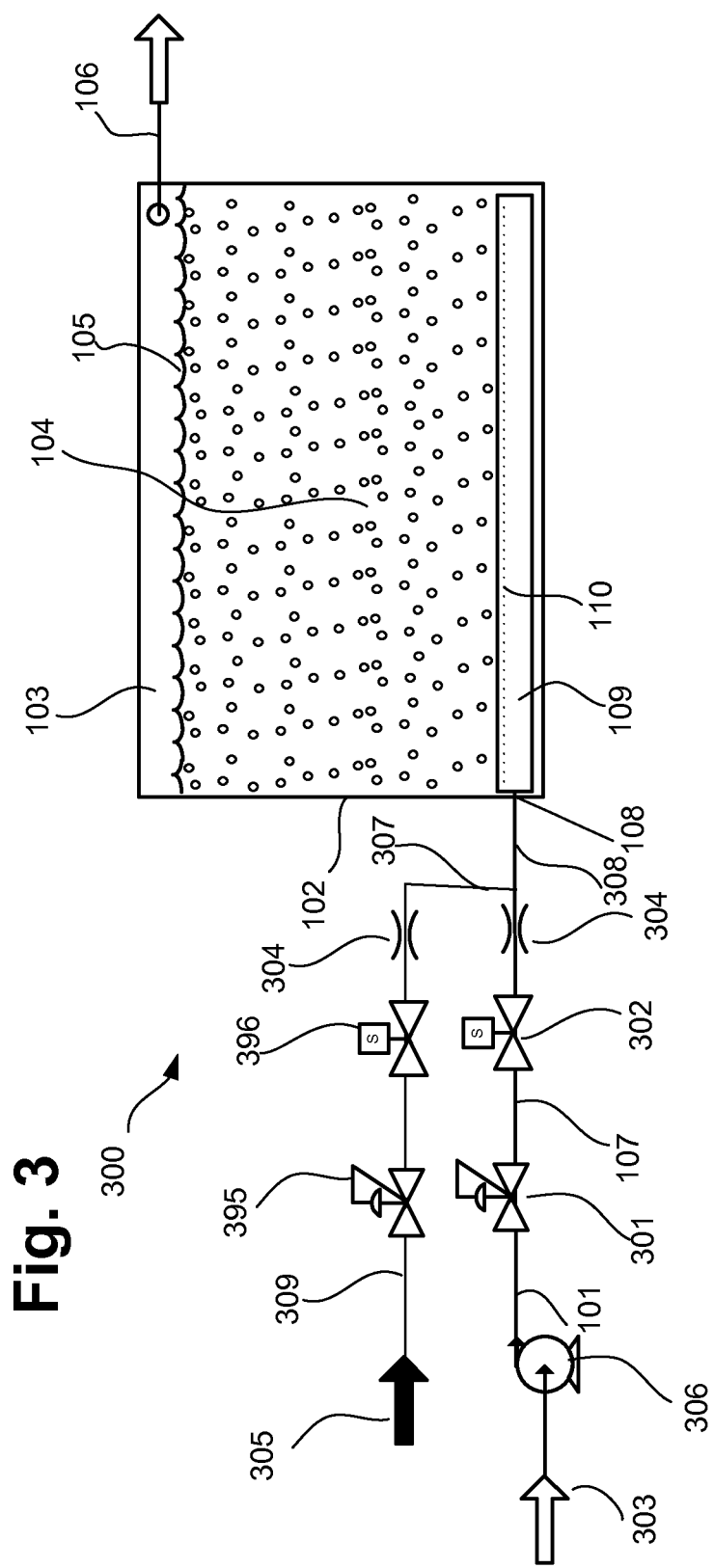
FIG. 3 illustrates a photobioreactor system having integrated sparging, according to embodiments of the present invention.

Carbon dioxide may be introduced to the media by sparging with gas of the desired concentration. FIG. 2 illustrates a cross section of reactor 200 with a sparge tube 110 in it. The sparge tube 110 can be supplied with gases from one or more sources of pressurized gas. FIG. 3 illustrates a similar system 300. FIG. 3 shows a reactor bag 104 for retaining media and a microorganism (e.g. algae), at least one sparge tube 110, a source of pressurized carbon dioxide 305 and an air compressor 303 used to supply gas(es), (e.g. carbon dioxide) via lines or tubes 101, 307, 308, 309. A pressure regulator 395 can be used to control the pressure of delivered carbon dioxide. A control valve 396 can be used to turn the supply of delivered carbon dioxide on and off. An orifice or throttling valve 304 can be used to control the flow rate of gases. In certain embodiments of the present invention, air pressure can be controlled by one or more pressure regulators 301 and, optionally, an air control valve 302 used to turn the air supply on and off. An orifice or throttling valve 304 can be used to control the flow of the air when the air control valve is on. Both the carbon dioxide control valve 396 and the air control valve 302 can be operated in concert or independently to provide flexibility in gas supply to a system. Throttling valves 304 can be manually, passively, or electronically controlled valves. In one embodiment, throttling valves are Mass Flow Controllers (MFCs).

In certain embodiments of the invention, when the control valves 302 are in an "on" position, pressurized gas flows to the delivery tube (e.g. sparge tube 109) and out of holes in the delivery tube 110. Once outside of the tube 109, gas forms bubbles that rise through the media until reaching a free surface interface 105 of the bag 102. In some embodiments, one or more delivery tubes 109 can be made in a variety of ways and from a variety of materials. For example, delivery tube 109 may include pipes or tubes with holes drilled, machined, laser drilled, or produced by other means; porous rocks; bubblers molded from various materials; natural materials that are inherently porous; and/or plastic film tubes with small holes in them. In certain embodiments, delivery tubes 109 are formed of plastic film with small holes manually punched or manufactured using lasers.

During the time when the bubbles rise through media, if partial pressure of carbon dioxide gas is higher than the equivalent partial pressure of the dissolved carbon dioxide in the media, the carbon dioxide will diffuse from the gas and be absorbed into the media. For a given media and temperature, the amount of carbon dioxide that diffuses into the media is a function of the partial pressure of the gas in the bubble, the equivalent partial pressure in the media, the surface area of the gas bubble, the residence time of the gas bubble in the media, the motion or movement of the bubble in the media, and other factors such as the number of bubbles present in the media. Bubbles that reach a media surface usually collapse, and gas from the bubble then combines with the gas above the media. Diffusion between the gas and the media then continues until the partial pressure and equivalent partial pressures reach equilibrium.

In many bioreactors, depth of media is shallow enough that the time it takes the bubbles to rise to the surface is very short. In certain embodiments, bioreactors have media depths of about twelve inches and the bubbles can rise to the surface in one to two seconds. This short period of time often does not permit much carbon dioxide to diffuse into the media, and can result in low efficiency of carbon dioxide use, unless the carbon dioxide can be captured and reused in some manner. Furthermore, considerable energy can be expended to raise the gas mixture containing carbon dioxide to a sparging pressure.

A larger portion of the carbon dioxide-enriched gas is used by increasing the time it takes for the bubbles to reach the surface. This may be accomplished by imparting a downward flow to the media through which the bubbles rise. This downward flow counteracts the motion of the rising bubble and, with careful design, the flow can be set at a rate that matches the rate at which the bubbles would rise, thus effectively causing the bubbles to have little or no net velocity toward the surface. While this does increase the efficiency of carbon dioxide utilization, the energy cost to do this can be prohibitive for commodity products such as, for example, microorganism-based transportation fuels.

According to other embodiments of the present invention, gas can be introduced to the media for other reasons. For example, a bioreactor may use certain gas delivery methods to reduce settling out of cultures from a suspension. In addition, methods for agitating a culture can be used to minimize dead material or dead organisms from building up and adversely affecting a culture. Agitation can increase availability of nutrients and reduce culture death, as well as reducing the build-up of dead matter on the bottom of a bioreactor. In other embodiments, gas delivery causing agitation can be used to mix nutrients, reducing stratification of temperature, pH and/or other conditions that can affect the media. Gas delivery causing agitation (e.g. sparging) can be an effective method to reduce the amount of dissolved oxygen in the media.

Because of the costs associated with sparging, in certain embodiments of the present invention gases may be delivered to one or more cultures in a more limited and/or time-controlled fashion. For example, sparging of gases can be performed on an as-needed basis. In other embodiments, a photobioreactor allows additional time for gases to remain suspended above media, permitting significantly longer time for gas diffusion from the space above the media into the media. In accordance with such embodiments, transfer of gases through a liquid-gas interface, or free surface, along with the timing and control of gas delivery and its chemical composition enhance carbon dioxide absorption in the media.

As illustrated in FIG. 3, gas bubbles rise through media to the top of a bioreactor where the gases collect 103. A free surface 105 is created, where the gas can diffuse into the bioreactor. Depending on the bioreactor 300 gases may reside inside a bioreactor 300 above media where the gases can diffuse into the media until a desired result is reached. Such methods are effective for getting carbon dioxide into media with increased uptake efficiency and reduced power. Such a method may be referred to as using the free surface, according to embodiments of the present invention. In certain embodiments, rates at which carbon dioxide can diffuse from gases in a bubble form rising through media, or as a gas collected above media, are a function of difference between the partial pressure of carbon dioxide, and the equivalent partial pressure of that gas in the liquid media. For example, at sea level and ambient conditions of 25° C., atmospheric air contains approximately 0.038% carbon dioxide and has a partial pressure of about 38.5 Pa.

In other embodiments of the present invention, the total amount of carbon dioxide diffused in or out of media is a function of the available surface area and the difference in partial pressures of carbon dioxide in the gas and carbon dioxide in the media, at the media/gas interface. For example, larger media/gas interface areas can have higher rates of carbon dioxide transfer. The pH and amount of carbon dioxide in a given media at a given temperature and salinity is a function of the partial pressure of the carbon dioxide in the gas and the media in the bioreactor. Each of these variables can be affected by the interface area between the media and the head space in the bioreactor. In certain embodiments, microorganisms grown in a bioreactor consume carbon dioxide from media and release oxygen into the media. The systems of such embodiments may not necessarily be in equilibrium. In such embodiments, varying area of a free surface 105 can affect the pH in the media by affecting the relative rate(s) at which carbon dioxide goes in and out of the media. Thus varying the surface area can control the pH of the media and the culture, even if a constant concentration of carbon dioxide is used for gas delivery (e.g. sparging), or used as gas left in the free space above the media in a closed photobioreactor.

The equations, below, may be used to determine pH of distilled water at equilibrium for gas above its free surface containing the specified concentration of carbon dioxide. According to embodiments of the present invention, these equations are used for assessing, monitoring, and/or programming gas delivery in a photobioreactor. For example, one or more of these equations may be used to program a photobioreactor system for maintaining a constant pH where maintaining a constant pH can be a function of regulating carbon dioxide or other gas delivery to a system.

$$temp_C := 16$$

$$P_{atm} := 1 \cdot atm$$

$$temp_K := (temp_C + 273.15) \cdot K$$

$$Conc_{CO2} := 0 \cdot \%, .001 \cdot \% \ldots 100 \cdot \%$$

$$P_{CO2}(Conc_{CO2}) := P_{atm} \cdot Conc_{CO2}$$

$$C_{CO2} := 2400 \cdot K$$

$$k_{CO2\_298K} := 29.412 \cdot \frac{liter \cdot atm}{mol}$$

$$k_{CO2\_temp} := k_{CO2\_298K} \cdot e^{\left[-C_{CO2} \cdot \left(\frac{1}{temp_K} - \frac{1}{298 \cdot K}\right)\right]}$$

$$CO2(Conc_{CO2}) := \frac{P_{CO2}(Conc_{CO2})}{k_{CO2\_temp}}$$

$$pH(Conc_{CO2}) := \log\left(\sqrt{4.45 \cdot 10^{-7} \cdot CO2(Conc_{CO2}) \cdot \frac{liter}{mol}}\right)$$

$temp_C$ = Media Temperature in degrees Celsius $temp_K$ = Media Temperature in degrees Kelvin $P_{atm}$ = Atmospheric pressure $Conc_{CO2}$ = Volumetric concetration of $CO_2$ in sparge/free surface gas $P_{CO2}(Conc_{CO2})$ = Partial pressure of $CO_2$ in gas $C_{CO2}$ = Coefficient for the temperature dependance of CO2 solubility in water $k_{CO2\_298K}$ = Henry's Constant for $CO_2$ in water at 298 K $k_{CO2\_temp}$ = Henry's Constant for $CO_2$ in water at a given temperature $CO2(Conc_{CO2})$ =

$CO_2$ concentration in water that is in equilibrium with the gas $pH(Conc_{CO2})$ = pH of water that is in equilibrium with the gas.

Figure 4:
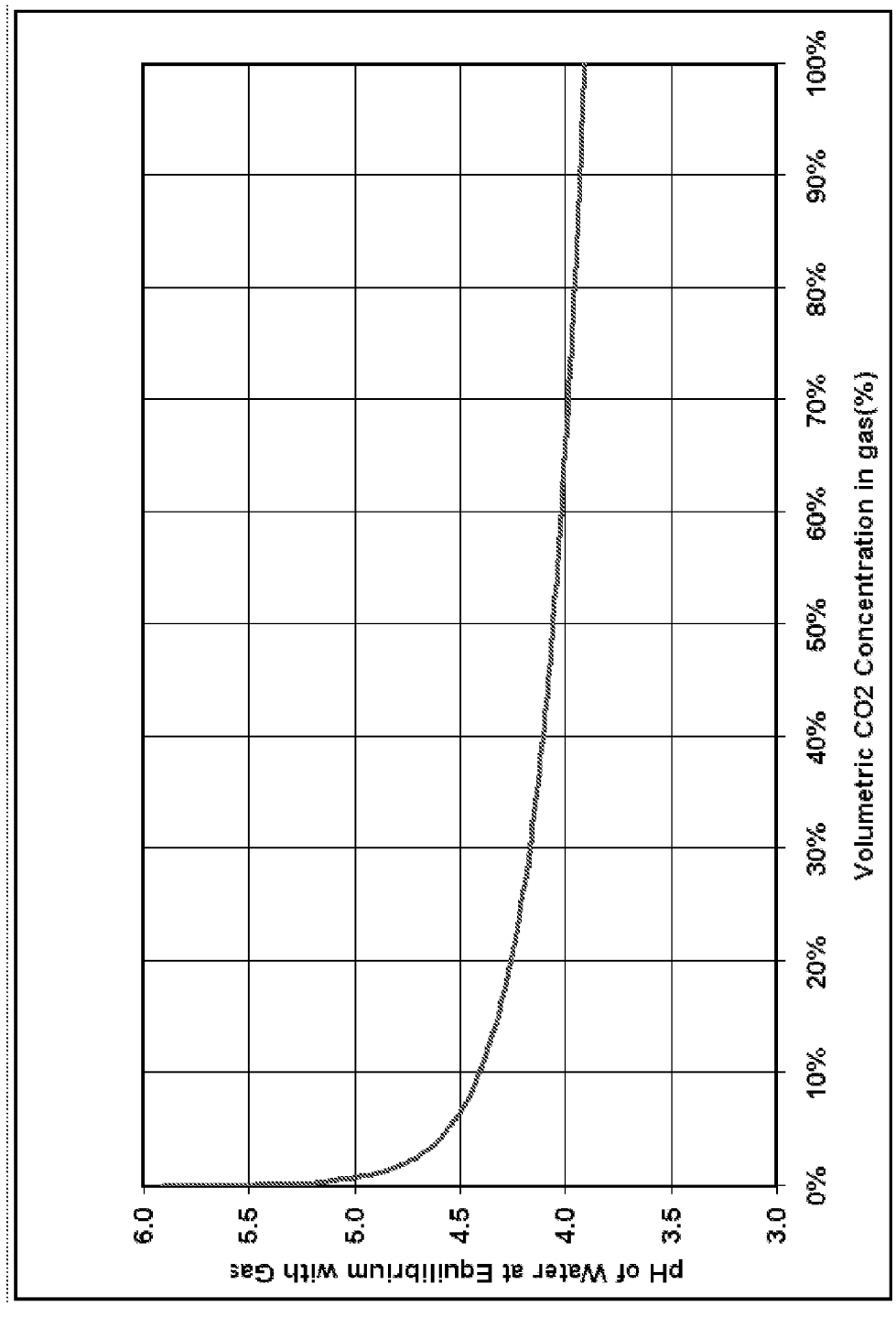
FIG. 4 represents a graph illustrating pH of pure water in a photoreactor versus concentration of carbon dioxide gas, according to embodiments of the present invention.

FIG. 4 illustrates a plot reflecting a correlation between volumetric carbon dioxide concentration in gas and pH of distilled water at equilibrium. This equation may vary for different medias in which other chemical constituents are present, such as, for example, salts. Pressure differences or temperature changes in a media may vary this equation.

According to some embodiments of the present invention, if the amount of carbon dioxide that can be supplied to the media exceeds what can be consumed, time may be given for the system to equilibrate to a predetermined pH or move toward a desired pH based on the concentration of carbon dioxide in gases being delivered to the system and gases trapped above a free surface of the media. If a system does not have capacity to supply a required amount of carbon dioxide, there can be a deficit and media pH can rise. Alternatively, a system may have some ability to self regulate, because a reduction in carbon from the media by the algae may affect the equivalent partial pressure and therefore cause more carbon dioxide to diffuse into the media. However, this self-regulation may not be as strong as desired and pH of the media can rise above predetermined levels for a given growth of a microorganism.

One way to achieve free surface carbon dioxide delivery to media involves delivering gas to the media intermittently, such as, for example, by sparging. Thus, power consumption can be reduced and a more favorable net energy return on the entire process can be achieved. Reduced power consumption can lead to a reduction in operating costs and reduced capital costs if smaller equipment can be used and/or if decreased equipment use can be achieved over multiple bioreactors. For example, equipment reduction can include elimination of or reduction in the size of: compressors, scrubbing equipment, valves, and/or other related equipment. Such a free surface design can create a higher uptake efficiency of carbon dioxide by reducing wasted gases; for example, exhaust carbon dioxide can be recycled and re-delivered to the media for growing cultures. A free surface design increases energetics and permits carbon sequestration for current or later use, according to embodiments of the present invention.

Figure 5:
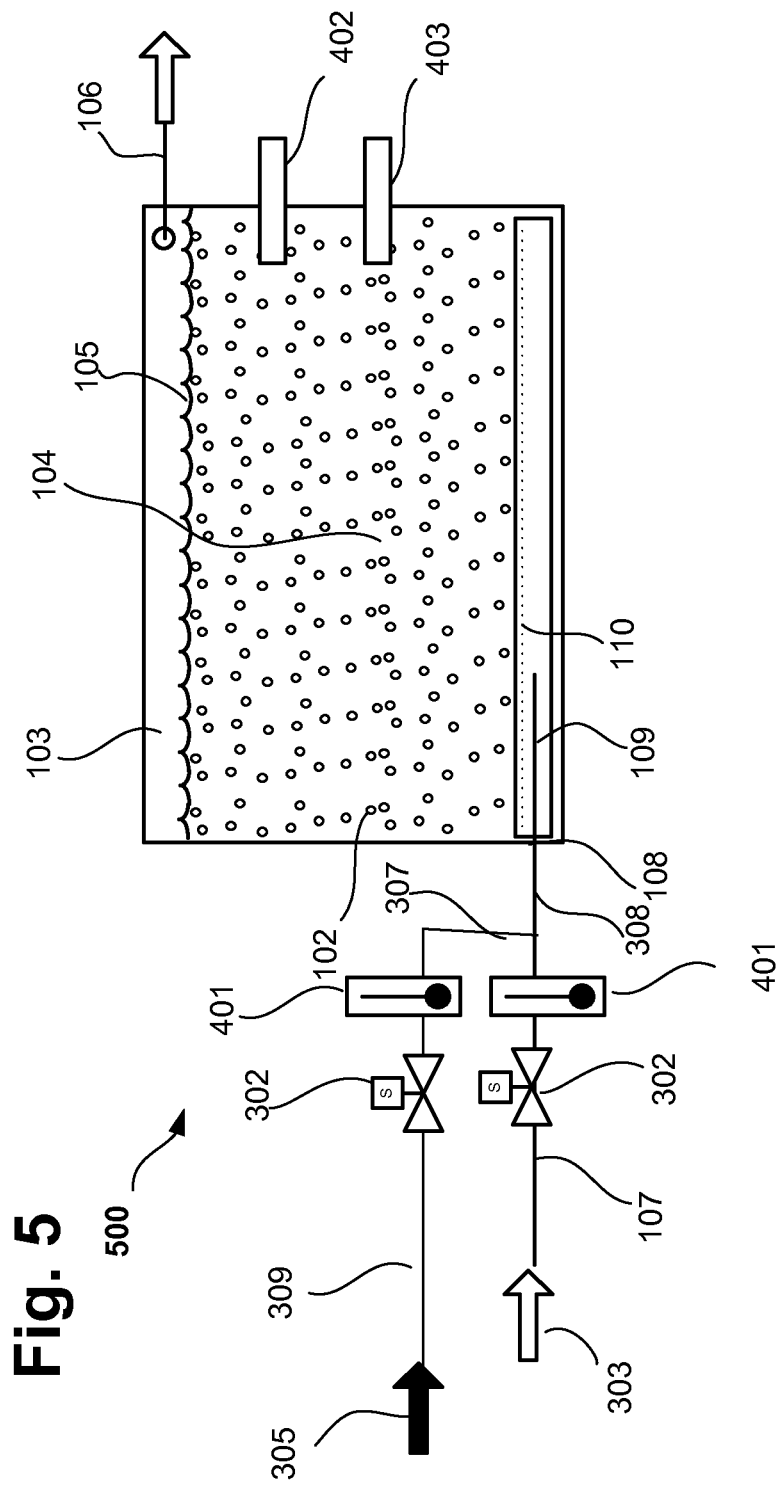
FIG. 5 illustrates a photobioreactor system having integrated sparging, according to embodiments of the present invention.
Figure 6D:
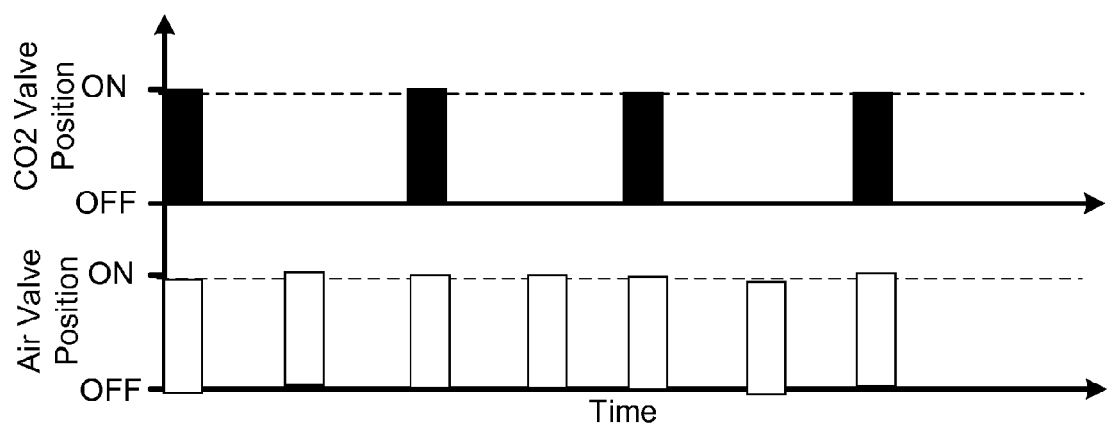

FIG. 5 illustrates a bioreactor configured for intermittent gas delivery to a culture of microorganisms. According to some embodiments of the present invention, system 500 delivers at least two gas compositions, carbon dioxide 305 and air 303, through a connecting member 107, 309 to a valve (e.g. solenoid valve) 302. Such delivery is regulated by a rotameter 401 and valve 302; rotameter 401 may be manual, timed, or automated, for example. A member 107 in fluid communication with the rotameter 401 is also in fluid communication with a delivery member 308 that delivers gases into the media 104 of a bioreactor. According to embodiments of the present invention, carbon dioxide 305 can be premixed with air 303 prior to delivery 308 to the bioreactor. FIGS. 6A-6D illustrate some duty cycles, or delivery patterns, for delivery of gases to a bioreactor. FIG. 6A illustrates delivery timing for air and carbon dioxide, in which the delivery of air occurs in a relatively fixed duration over relatively regular periods while delivery of carbon dioxide is asynchronous with the delivery of air. Although delivery of carbon dioxide and air is described, one of ordinary skill in the art will recognize, based on the present disclosure, that a similar delivery timing cycle may be used for other kinds of gases. FIG. 6B illustrates delivery of air first for any given cycle, followed by delivery of carbon dioxide to achieve a desired carbon dioxide partial pressure for each cycle. FIG. 6C illustrates synchronized delivery of one or more gases having an irregular delivery period. FIG. 6D illustrates exemplary delivery of one gas (e.g. carbon dioxide) where the gas is delivered less frequently than one or more other gases (e.g. air).

Figure 7A:
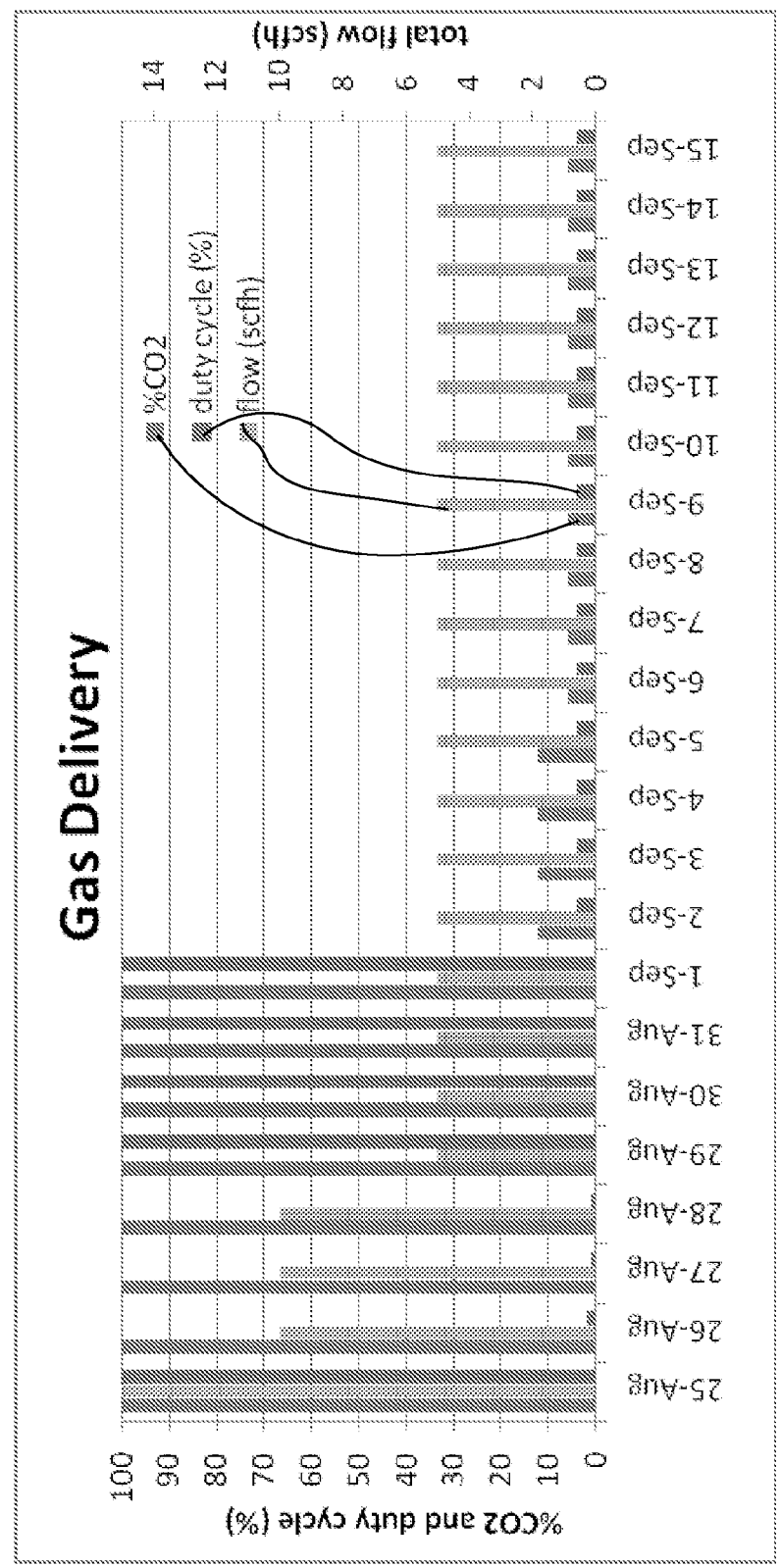
FIG. 7A depicts a bar graph of experimental conditions including percent gas, duty cycle and flow of gas over time, according to embodiments of the present invention.
Figure 7B:
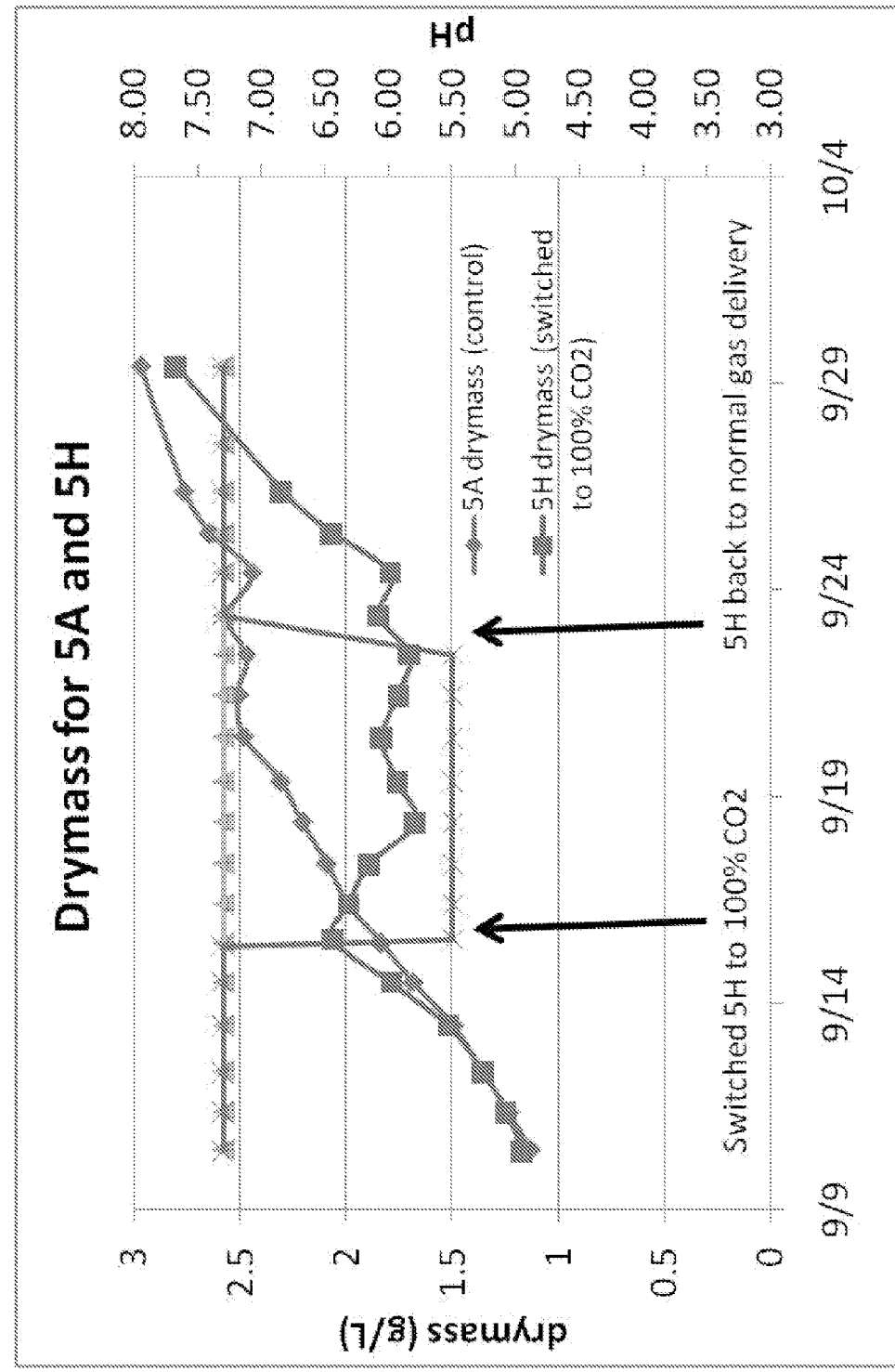
FIG. 7B represents a chart of pH level, and drymass for control and experimental algae cultures over time, under different gas delivery conditions, according to embodiments of the present invention.

FIG. 7A depicts a graph of experimental conditions including percent carbon dioxide concentration, duty cycle (percentage of time during which gas delivery is "on") and flow rate of gas when gas was on, according to embodiments of the present invention. FIG. 7B is a chart showing pH level and drymass (g/L) for control and experimental algae cultures over time, under different gas delivery conditions, according to embodiments of the present invention.

Figure 8:
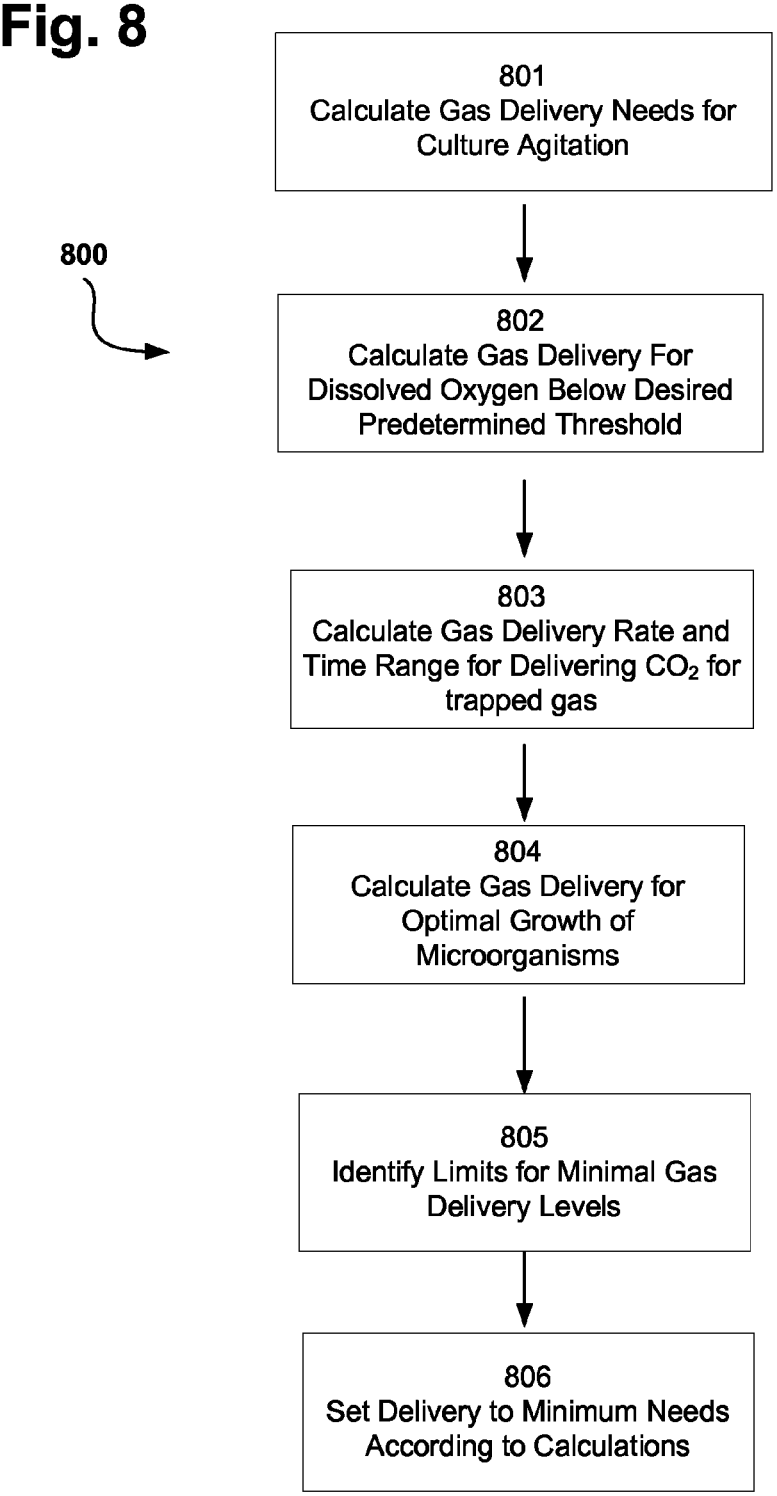
FIG. 8 depicts a flow chart showing a method for determining gas delivery for one or more photobioreactors, according to embodiments of the present invention.

FIG. 8 depicts a flow chart 800 showing a method for determining carbon dioxide delivery for one or more photobioreactors, according to embodiments of the present invention. For a given system, minimal gas delivery needs can be identified. A duty cycle is a timing pattern representing the percentage of time during which gas delivery is on versus off. Gas delivery intensity is represented by flow rate. According to some embodiments of the present invention, the photobioreactor system uses the least amount of sparging required to minimize energy consumption and the cost of preparing and possibly reprocessing the sparge gases. In flow chart 800, an estimate of the amount of gas delivery required to satisfy certain constraints is made. An estimate for gas delivery needs for culture agitation is calculated in block 801. An estimate for gas delivery for mixing is calculated in block 802. An estimate for gas delivery for removing dissolved oxygen is calculated in block 803. Blocks 803 and 804 calculate gas delivery for carbon dioxide addition and optimal culture growth, according to embodiments of the present invention. Optionally, additional blocks with more factors that could affect the amount of gas delivery may be added at block 805. At block 806, gas delivery needs are set to match or approximate the gas delivery need that calls for the most frequent and/or longest length of time, such that all needs for a particular culture are met, according to embodiments of the present invention.

FIG. 9 depicts a flow chart 900 showing a method for determining gas delivery based on carbon dioxide requirements for one or more photobioreactors, according to embodiments of the present invention. According to such embodiments of the present invention, a determination of carbon dioxide needs in the free space (block 903) is used to determine gas needs for a photobioreactor system (block 904). When the free surface method is used to introduce carbon dioxide or other gases into the media, continuous gas introduction can be eliminated in many situations. For example, a signal can be sent to one or more gas actuators (block 906) instructing intermittent gas delivery instead of continuous gas delivery, according to embodiments of the present invention. In fact, in the event gas delivery, either by sparging or direct delivery, is not required to provide any other function such as removing dissolved O2 or mixing, gas delivery in the reactor can be left off for long periods. For example, gas delivery in a photobioreactor can be left off for one hour to several hours. FIG. 9 illustrates a representative algorithm inside one of the blocks of FIG. 8. Flow chart 900 represents one way in which carbon dioxide delivery to a bioreactor may be controlled where block 901 represents a preset pH for a bioreactor. Based on a desired pH 901 setpoint, an algorithm 902 is used to determine carbon dioxide concentrations 903 for the head space and based on concentrations determined in 903, flow rates for gas delivery are determined 904 similar to block 803 as described in FIG. 8, according to embodiments of the present invention. Signals are received by gas actuators 905 which affect reactor 907. Sensors for (908, e. g. pH) can be used for measuring certain parameters (e. g. pH) and delivery can be set similar to block 806 as described in FIG. 8.

Delivery of gases to a bioreactor can serve many functions including, but not limited to, keeping microorganisms (e.g. algae) in suspension, diffusing different gases into the media, and removing dissolved oxygen in the media. In certain embodiments, microorganisms may need agitation to a culture for maintaining a suspension. In some embodiments, different algae strains may require frequent sparging or media agitation to keep them in suspension, but may not require as much sparging for removal of dissolved oxygen or addition of carbon dioxide during nighttime. In other situations, algae may need an increase in frequency, flow rate, and/or flow duration of carbon dioxide delivery to remove dissolved oxygen during periods of high light, long days and high culture density.

Figures 10A, 10B:
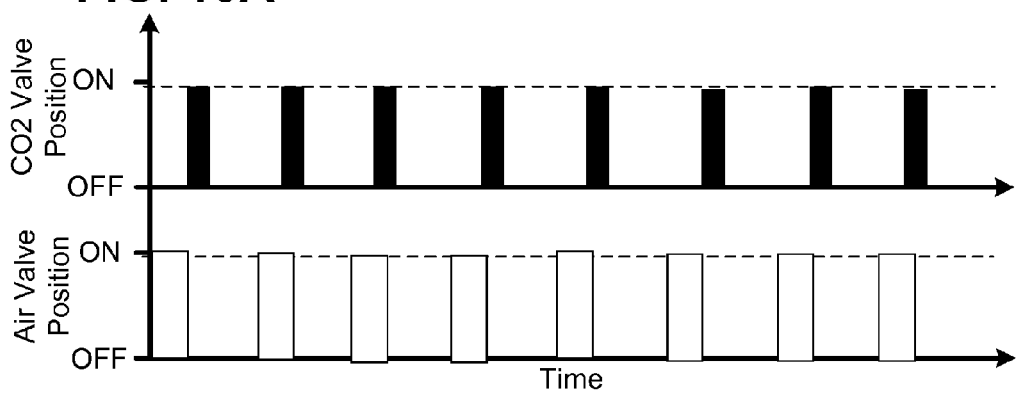
FIGS. 10A and 10B illustrate timing patterns corresponding to delivery of air and carbon dioxide to one or more photobioreactors, according to embodiments of the present invention.

FIGS. 10A and 10B illustrate additional timing patterns for delivering one or more gases to a culture, according to embodiments of the present invention, in which the carbon dioxide delivery follows the air delivery for each cycle. FIG. 10A illustrates a graph of intermittent introduction of two gases, carbon dioxide (solid bars) and air (open bars). In this gas delivery pattern, carbon dioxide is introduced for a shorter period of time and at a different time than air is introduced. FIG. 10B illustrates an alternative pattern for gas introduction to a culture. Initial introduction of carbon dioxide is longer than three subsequent additions of carbon dioxide, according to such embodiments of the present invention. One of ordinary skill in the art, based on the disclosure herein, will appreciate the wide range of gas delivery timing patterns that may be employed for intermittent delivery of gas to a photobioreactor. According to some embodiments of the present invention, gas delivery needs are dictated by the need to mix the media. In such cases, it may be beneficial to deliver gases most of the time with air or other gases, and add carbon dioxide selectively at the end of a cycle as a mixture or as concentrated or pure carbon dioxide.

FIG. 11 illustrates a block diagram 1100 illustrating photobioreactor control according to embodiments of the present invention. In this diagram, several factors and/or variables (e. g. 1101, 1102, 1103, 1104) can be considered by an open loop controller 1105 to determine rates of gas delivery, according to embodiments of the present invention. There are many control algorithms that could be employed to control free surface and/or the intermittent gas delivery to a system. One method involves using no feedback sensors, but instead relying on an open loop model (for example, as illustrated in the block diagram 1100) or look up tables (1103) with predetermined levels for optimal gas concentrations and gas delivery times (e. g. patterns of past delivery (previous year, previous month, previous week), historical data of sun position, etc., 1102). For example, an open loop controller could use stored historical data, data from the internet or other sources, or could use simple global sensors at the facility such as temperature or sunlight (see FIG. 11). FIG. 12 illustrates a diagram 1200 for a closed loop gas delivery system and carbon dioxide controller, according to embodiments of the present invention. In this diagram, an algorithm 1202 for pH control determines concentration of carbon dioxide for free space for a predetermined pH (block 1203). Flow rates can be determined for carbon dioxide and other gases, such as air (block 1204). Based on the determined rates, a signal may be sent to actuators (block 1205) for controlling delivery of gases to a reactor (block 1208). In addition, conditions in a system can be measured by sensors 1209 for adjusting delivery rates of gases and as a method for feedback control, in which the sensor signals (block 1209) are fed back into the pH control algorithm (block 1202) and optionally back into the algorithm determining the carbon dioxide concentration for the head space (block 1203).

Certain embodiments include controllers grouped into families of controllers. In other embodiments, gas delivery to the free surface is controlled with a feedback controller (e.g. 1206) capable of receiving feedback variables. Some embodiments include a pH sensor to assist in controlling media pH. In accordance with such embodiments, carbon dioxide levels are varied to maintain a constant pH. For example, the process outlined in FIG. 12 can be employed in the control of carbon dioxide delivery to a photobioreactor based on a sensed pH and a pH setpoint (or set range), according to embodiments of the present invention.

According to some embodiments of the present invention, rule-based or heuristic control schemes may be used for developing controllers of a bioreactor system. For example, embodiments may be combined to have open loop and/or closed loop controllers for regulating gas delivery to a bioreactor system. Numerous combinations of sensors can be used for both open loop and closed loop control. Some of the signals that could be used for open loop control include, but are not limited to, temperature, photosynthetically active radiation (PAR), culture density, pH, light conditions, humidity, and free surface and head space variations. Some of the feedback signals might include, but are not limited to, pH, optical density, nutrient levels, dissolved oxygen levels, and carbon levels. Controllers may be interrupt driven, may operate at a fixed frequency, or may operate at a frequency that varies by period, pulse width, and/or overall duration, according to embodiments of the present invention.

While it is possible to control carbon dioxide concentrations in gas mixtures by timing opening and closing of valves that only have an open and closed state, it may be desirable to control the flow rate of gases such as carbon dioxide, air, and any other gases introduced to a reactor. FIG. 13 illustrates a bioreactor system 1300 in which the bioreactor is capable of having variable gas delivery flow rates. Mass flow controllers 1301, 1303 can continuously adjust flow rates of various gases as the gas is delivered to the system by conduits 307, 308. Certain embodiments may include a controller 1302 for adjusting the one or more flow controllers 1301, 1303 of a system. A controller may be programmed and/or have stored data for controlling conditions of the bioreactor system (e.g. pH). In addition, a controller 1302 can be operably connected to one or more flow controller 1301 in order to control specific ratios of the one or more gases delivered to the bioreactor and, optionally, in order to deliver a predetermined mixture of gases or deliver one of the one or more gases at separate intervals. In this system 1300, exhaust gases exit head space 103 by a separate opening 106.

FIG. 14 illustrates a photobioreactor system 1400 with multiple gas delivery, according to embodiments of the present invention. The gas 1401 delivered in the gas delivery system may be a pre-mixed gas, according to embodiments of the present invention.

In other embodiments, pH can be controlled by adjusting gas delivery timing. As shown in FIG. 15, a photobioreactor delivers one or more gases in a constant ratio, pre-mixed in a pre-mixer 1502 before delivery to the bioreactor 103. As illustrated, gases 305, 101 are introduced via lines 1503, 107 to a mixing member 1502 (such as, for example, a mixing valve), and then delivered through line 1501 as a predetermined ratio of gases through a valve 302 to a bioreactor 103, according to embodiments of the present invention.

Figure 16:
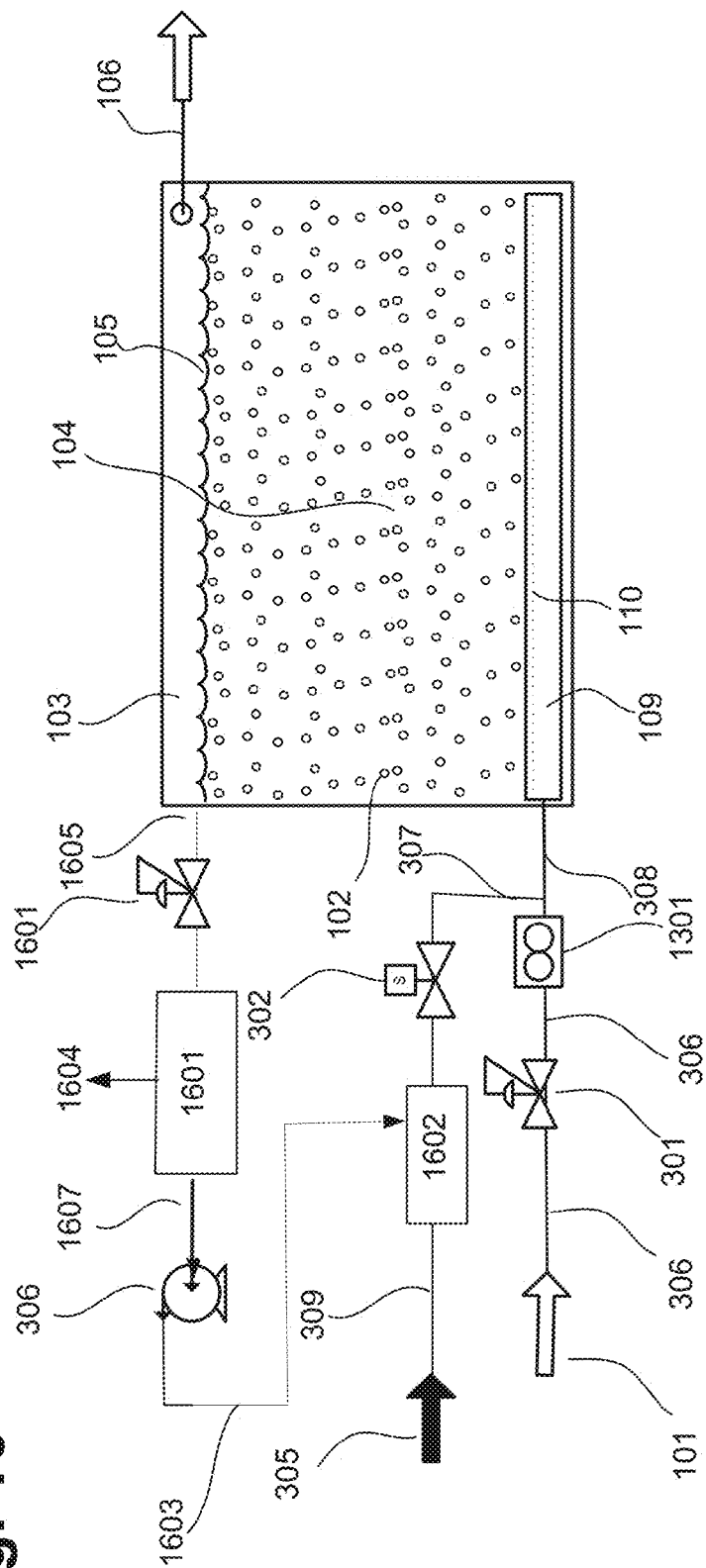
FIG. 16 illustrates a photobioreactor system for capturing and recycling exhaust gases from the system, according to embodiments of the present invention.

In certain embodiments, gas delivery may be controlled by operating conditions other than delivering the desired amount of carbon dioxide. For example, gas delivery may be governed by a need to mix the media. There may be situations in which gases exiting a bioreactor through the exhaust port 106 contain enough carbon dioxide offset the costs of collecting and recycling or storing the carbon dioxide. FIG. 16 illustrates a photobioreactor system capable of capturing one or more gases in a head space (or above a media free surface) and/or capable of reusing the captured gases. In FIG. 16, one or more gases 101, 305 are introduced to a bioreactor by lines 306, 309, which may be tubing or pipes, for example. Carbon dioxide can be stored in a tank 1602 or delivered via a valve 302 and/or flow controller 1301. In addition, gases accumulating in the head space of a system 103 can exit a port 1605, optionally regulated by a regulator 301 (e.g. pressure regulator). The regulator can be in fluid communication with a gas separator 1601, allowing some gases to be separated 1604 and capturing other gases for reuse (e.g. carbon dioxide). Then captured gases from tank 1601 can flow through line 1607 to pump 306 for delivery through line 1603 to a gas storage tank 1602 for reuse, according to embodiments of the present invention.

According to some embodiments of the present invention, a photobioreactor gas delivery system employs only carbon dioxide and no other gases. One advantage of such a system is that gas in the head space will be carbon dioxide and oxygen. There would be only two gases leaving the bioreactor port 106 or recycled through a recycling port 1605 in such systems. A lack of nitrogen in gases exiting a bioreactor can facilitate separating of carbon dioxide for reuse, according to embodiments of the present invention. According to some embodiments of the present invention, the system illustrated in FIG. 16 is used with only carbon dioxide 305 in the entry ports and no other gases. Additionally, it may be beneficial to use only carbon dioxide and another gas that has little if any oxygen in it, such as processed stack gas, for example. This may permit the system to be run with the desired concentration of carbon dioxide, yet still have a very low concentration of oxygen, which would be desirable for maximum growth.

Figure 17:
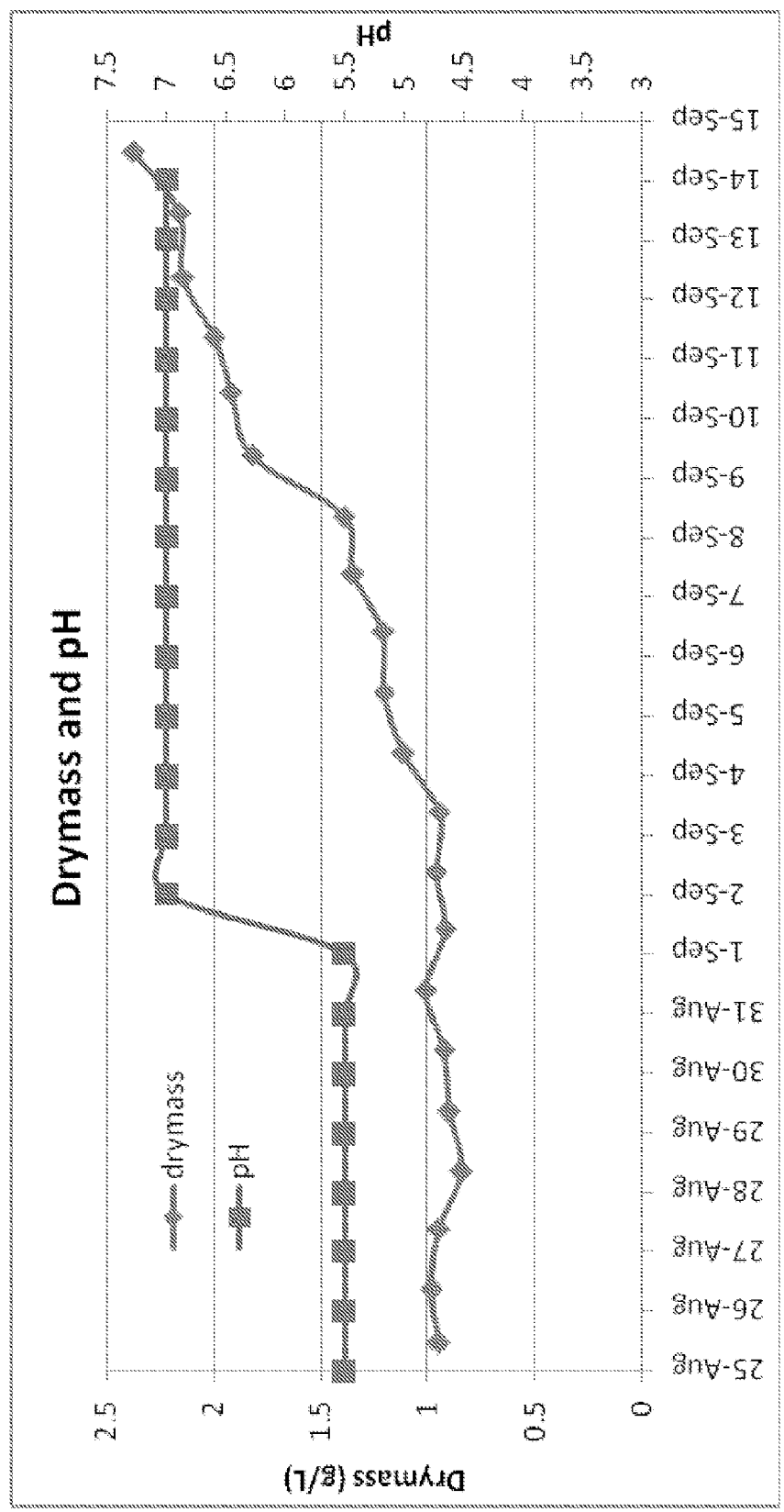
FIG. 17 is a plot illustrating drymass produced and pH over time of a photobioreactor system utilizing carbon dioxide delivery only, according to embodiments of the present invention.

FIG. 17 represents a plot from data obtained using a system having only carbon dioxide delivered to a bioreactor. This plot illustrates daily measurements of pH and dry mass of an algal photobioreactor. As illustrated in this plot, such a setup may result in a relatively low pH. Other species of algae or other microorganisms may not be as sensitive to the low pH and could tolerate such conditions. Nevertheless, the test illustrated the viability of a photobioreactor using only carbon dioxide delivered to a photobioreactor. According to other embodiments of the present invention, chemicals or other nutrients are supplied to the media to offset the low pH that sometimes results from a higher concentration of carbon dioxide delivery.

Figure 18:
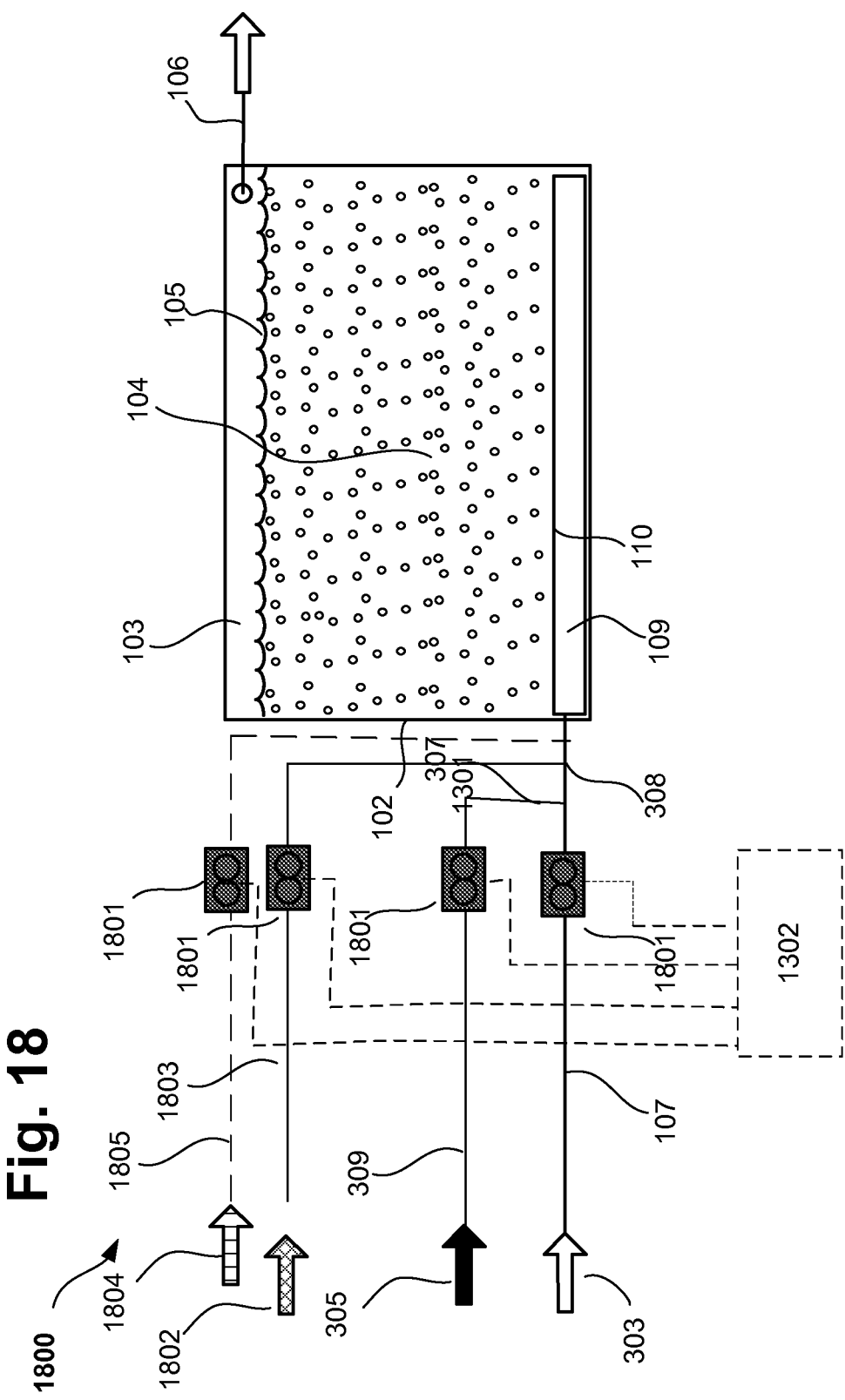
FIG. 18 illustrates a photobioreactor system with multiple gas delivery, according to embodiments of the present invention.

In other embodiments, a photobioreactor system uses a combination of gases, for example: air, carbon dioxide, and/or an inert gas like nitrogen. Such a gas combination reduces the amount of dissolved oxygen in the system, according to embodiments of the present invention. In addition, a reduced level of oxygen in a culture leads to lower power consumption due to the lower amount of gas delivery (e.g. sparging) for removing the dissolved oxygen, according to embodiments of the present invention. In certain embodiments of the present invention, gases delivered to a system include, but are not limited to, air, carbon dioxide and an inert gas like nitrogen. Such gases or gas combinations may be delivered in a fixed duration, in an interval, and/or in varied concentrations. Alternatively, delivery of these gases may vary in duration, interval or concentration in order to provide more flexible control. FIG. 18 illustrates a photobioreactor 1800 system in which gases 303, 305, 1802 and 1804 are introduced to a photobioreactor 102. Various controllers or valves may be used for delivering the one or more gases to the system. Optionally, an inert gas 1802 may be introduced. Mass flow controllers may be used to control delivery of one or more gases, but numerous different valving systems, such as solenoids, could be made to work with good performance.

In other embodiments, systems can be designed to operate with a combination of multiple gases, each having different properties (e.g. concentrations, mixtures, duty cycles) that can be more favorable at different times and/or under different bioreactor conditions. In accordance with these embodiments, relative concentrations of air, carbon dioxide and other gases can be fixed or varied with time to provide more flexible control of a system. In the system 1800 of FIG. 18, member 1801 can be a flow controller, for example a mass flow controller, for the one or more gases controlled by one or more controller(s) 1302. In addition, entry of gases to a photobioreactor chamber 103 may be carried to the system via one or more pipes and/or lines and/or tubes 107, 309, 1301, 308, 1803, 1805. Entry of the one or more gases 308 may be by a single entry line or more than one entry line. One skilled in the art, based on the disclosure provided herein, will recognize the wide array of combinations of hardware, controllers, valves, gas delivery methods, and methods for configuring systems to achieve intermittent gas delivery to a bioreactor, according to embodiments of the present invention.

In other embodiments of the present invention, a photobioreactor system operates on carbon dioxide and an inert gas, for example nitrogen. One advantage of such a system can be an ability to regulate pH using varying concentrations of carbon dioxide and the inert gas, thus eliminating additional oxygen in the system. Embodiments of such systems may be implemented with the system of FIG. 18, in which carbon dioxide 305 and an inert gas 1802 can be selected as the only gases delivered to the bioreactor 103. Controller 1302 may be used to control the flow and/or regulate mass flow controller 1801 for delivery of the gases for such a system, according to embodiments of the present invention.

Mass flow rate controllers are capable of continuous variable control of flow rate of each gas from zero flow (off position) to a maximum flow (wide open position) for any given gas, according to embodiments of the present invention. In certain embodiments, variable flow rate for each gas may be achieved using mass flow controllers 1801 on each line, or by using fixed orifices on each line and then varying the upstream pressure of that circuit with an electronically controlled pressure regulator or the like. In other embodiments, variable speed pumps or compressors may be used. According to some embodiments of the present invention, variable flow control of carbon dioxide is achieved with a mass flow controller and air flow control is achieved with a solenoid valve. Gases may be introduced to the photobioreactor via sparging through a perforated film; the perforated film can be used to limit the flow area of gases into the culture suspension media.

Figure 19:
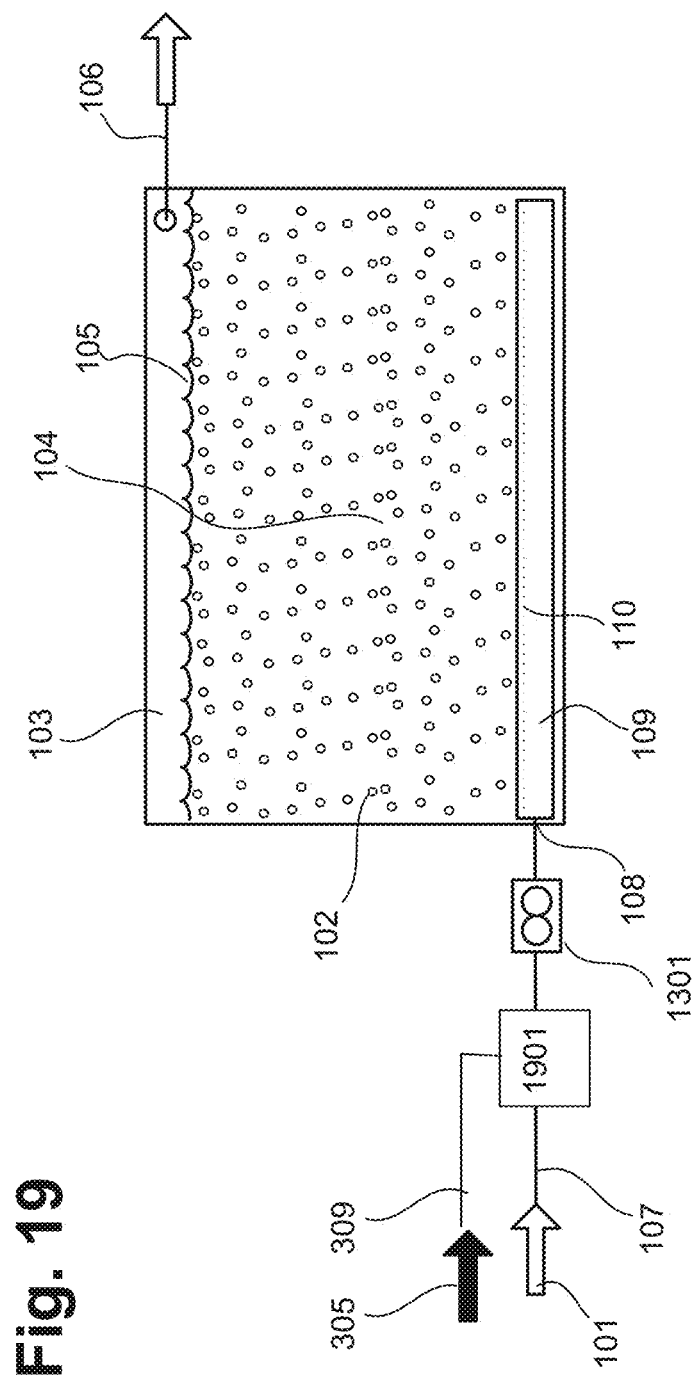
FIG. 19 illustrates a photobioreactor system with carbon dioxide delivery, a mixing apparatus and a flow controller, according to embodiments of the present invention.

Systems according to embodiments of the present invention may be designed with mixing valves or other hardware that creates a gas mixture with a constant concentration of carbon dioxide and the other gases in the mixture. Then the pH can be controlled by controlling the flow of the gas mixture to the reactor. As depicted in FIG. 19, flow can be controlled using a simple on off valve or with a device that continuously regulates the flow rate like a mass flow controller. In certain embodiments, gases for delivery to a bioreactor may be premixed in a mixing tank 1901 with varying ratios and concentrations depending on needs of a system and flow can be controlled with mass flow controller 1301 prior to entry to a bioreactor 102.

Figure 20:
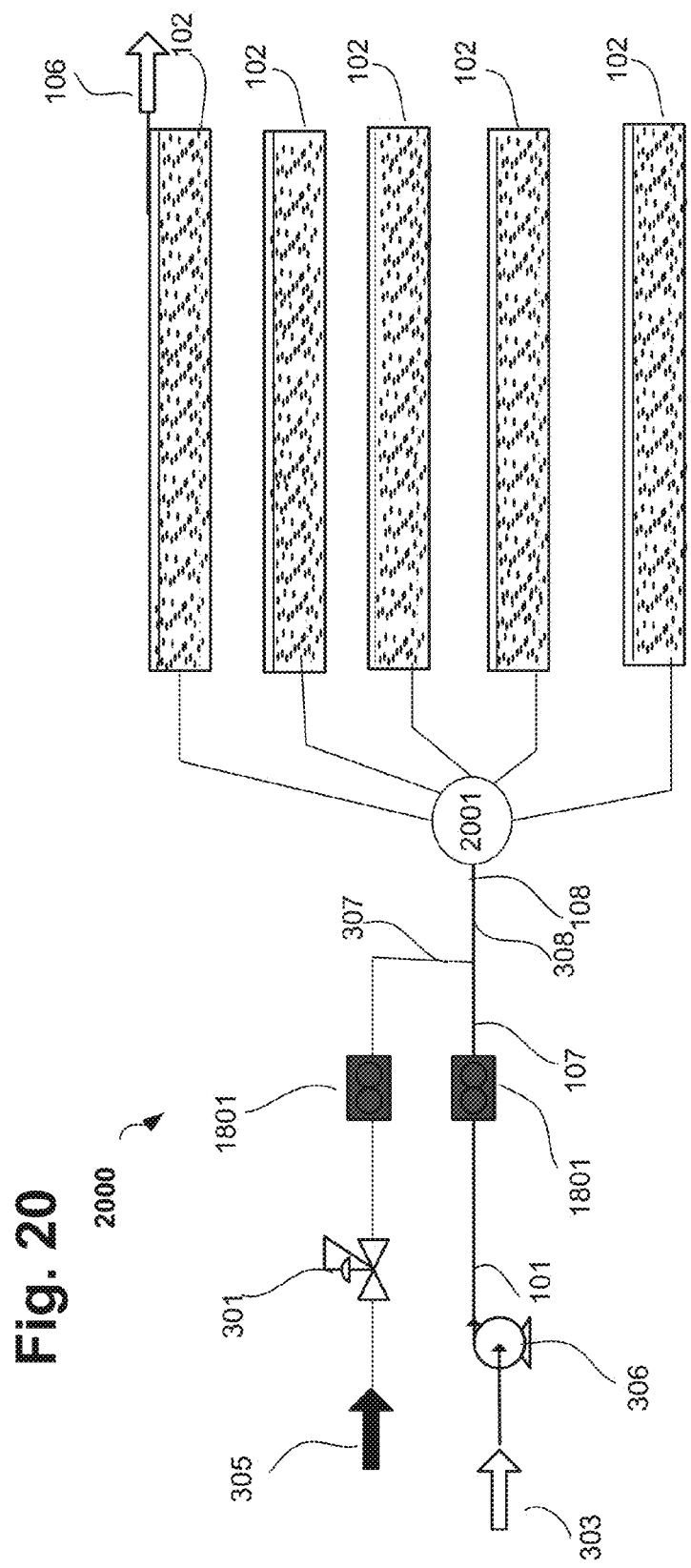
FIG. 20 illustrates a system configured to deliver gases to multiple photobioreactor systems, according to embodiments of the present invention.
Figure 21:
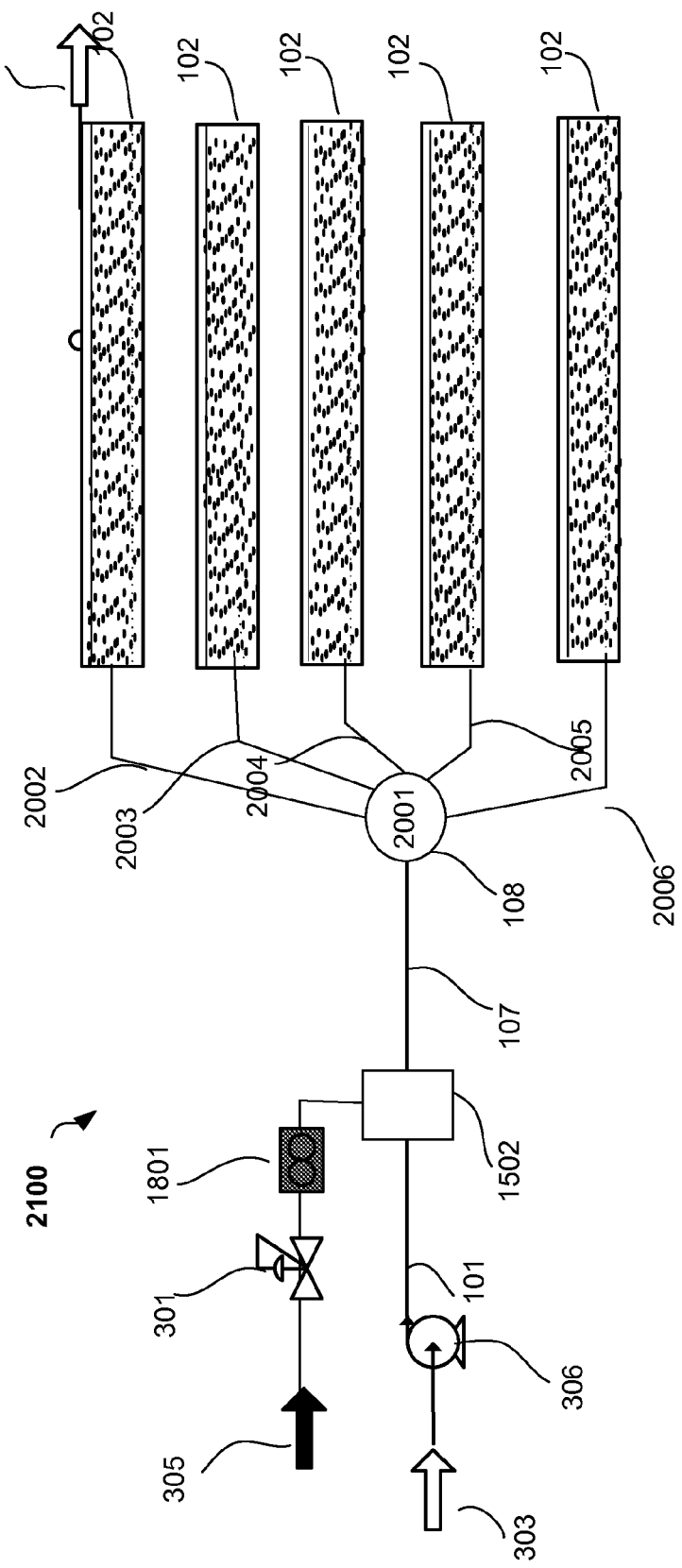
FIG. 21 illustrates an alternative system configured to deliver gases to multiple photobioreactor systems, according to embodiments of the present invention.

In some embodiments, intermittent delivery of gas can permit air and other gas supply hardware sized for one bioreactor, or bioreactor bank, to be shared, or multiplexed to supply multiple bioreactors or bioreactor banks. A valving compressor appropriately sized for one bioreactor bank can service additional bioreactors by switching a compressor or blower from one bioreactor bank to another. Alternatively, a smaller compressor with a larger gas storage tank may be used with intermittent gas delivery. FIG. 20 illustrates a gas delivery system 2000 in which one compressor serves multiple bioreactors 102 by means of a distributor member 2001. The distributor 2001 may be, for example, a valve. Pipes and/or tubing can deliver one or more gases to one or more bioreactors simultaneously or at predetermined concentrations and timing patterns. A distributor member 2001 can be operably connected to one or more mass flow controllers, flow controller and/or other valves 1801. As illustrated in FIG. 21, a multi-bioreactor system 2100 includes a mixing valve 1502 for premixing various gases prior to delivery to a distributor member 2001. The mixing of gases may vary depending on needs of a particular bioreactor at a particular time. Microorganisms grown in a given bioreactor of a multi-bioreactor system may be at different stages of growth (e.g. first to end stages of culture growth) or at similar stages of growth, according to embodiments of the present invention.

Figure 22:
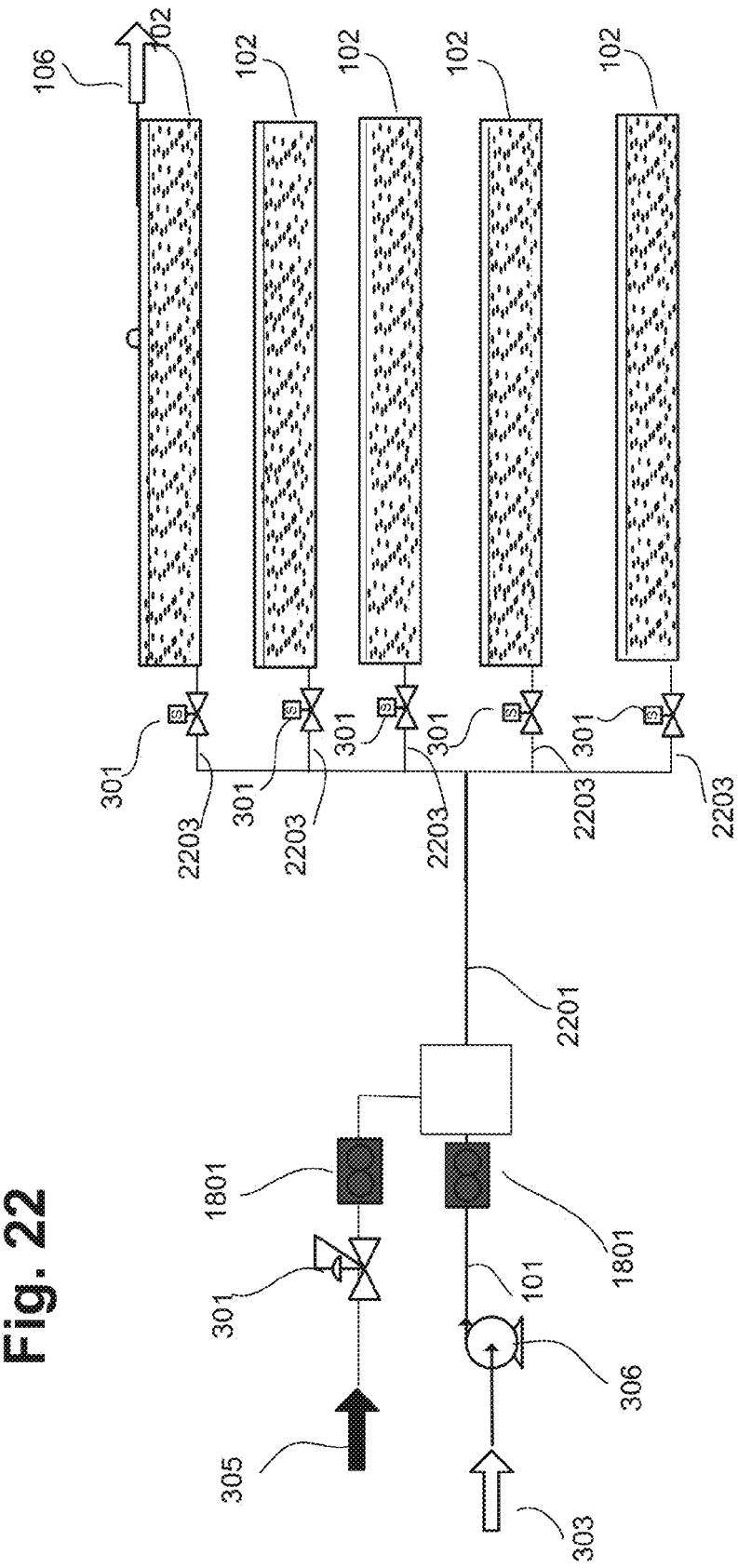
FIG. 22 illustrates yet another alternative system configured to deliver gases to multiple photobioreactor systems, according to embodiments of the present invention.

As illustrated in FIG. 22, multiple bioreactors 102 may be connected in fluid communication by a single pipe or tube 2201 and then operably connected to a source of gas or gases. This single tube or pipe 2201 can be linked to various pipes or tubes 2203 that deliver gas and/or gases to the multiple bioreactors 102. Optionally, each bioreactor may have a regulating member 301 for regulating delivery of gas(es) to each bioreactor. Here, a distributor member (similar to that described with respect to FIG. 21) can be replaced with individual solenoid valves 301 that control the flow of the air and/or other gases to each reactor or reactor bank. In addition, gases delivered to each of the bioreactors of a multi-bioreactor system may be premixed such that each bioreactor receives gases on predetermined schedule for a predetermined duty cycle. According to other embodiments of the present invention, gas delivery control is achieved with a motor that supplies air to the bioreactors as needed.

Figure 23:
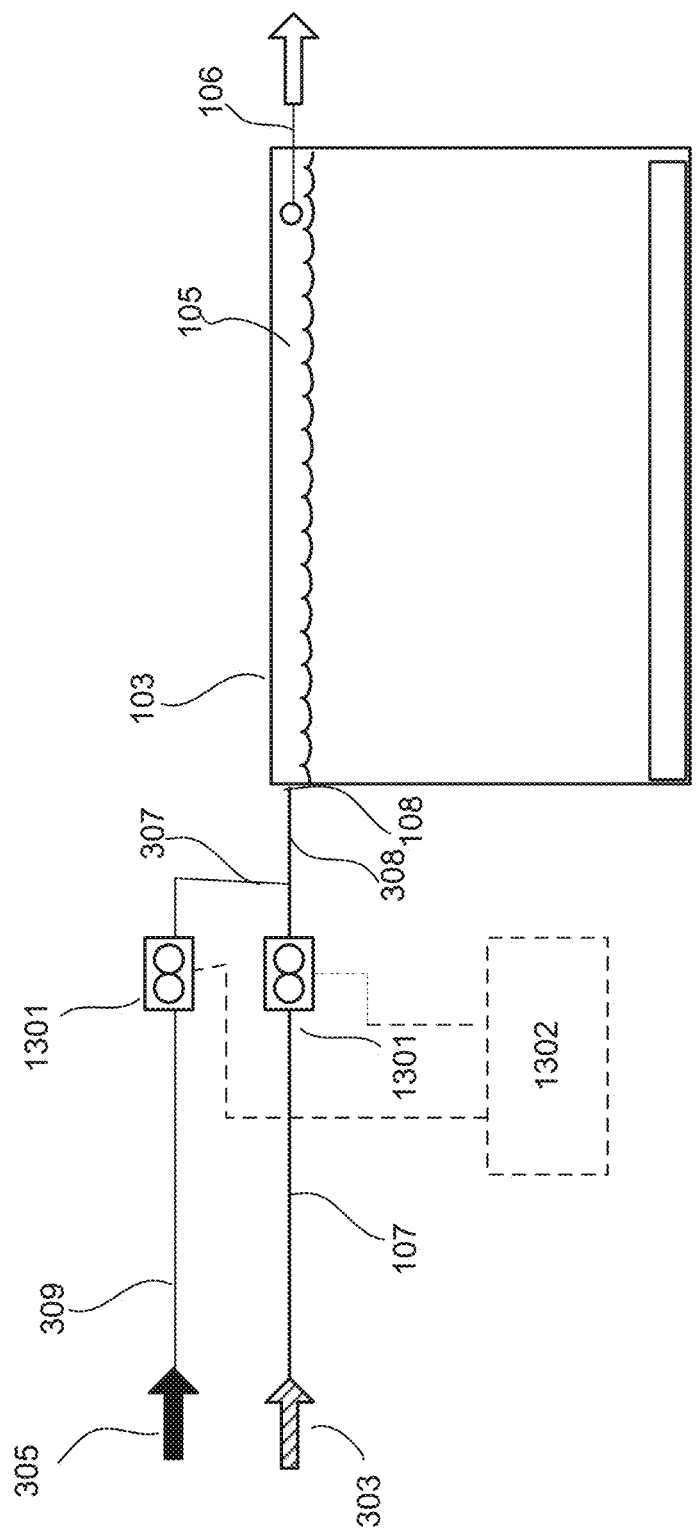
FIG. 23 illustrates a system configured to directly deliver gases to a photobioreactor system's free space, according to embodiments of the present invention.
Figure 24:
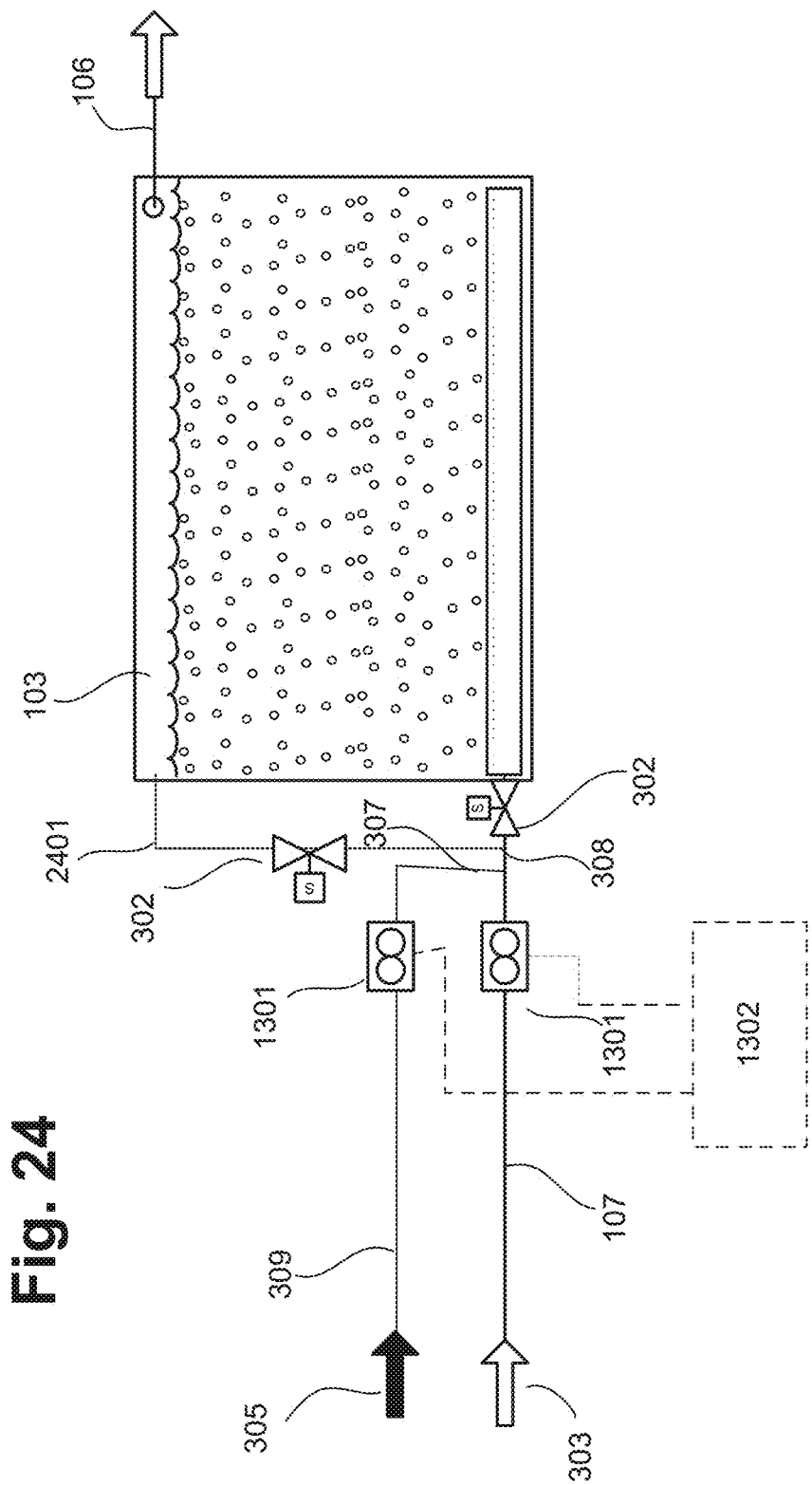
FIG. 24 illustrates a system configured to directly deliver gases to a photobioreactor system's free space and/or intermittently deliver gases to media of a culture, according to embodiments of the present invention.

FIG. 23 illustrates a bioreactor having gas added to head space or upper region of a bioreactor (e.g. in the upper part of media and/or above a free surface). In accordance with such an embodiment, carbon dioxide and/or other gases may be delivered without sparging through the media. An inlet 108 can directly supply gas through one or more ports 108 that can be, but are not necessarily, above the media level in the reactor 103. Directly supplying one or more gases to the head space above the media in this fashion can lower the supply pressures and hence lower the power requirements for the system; this method can also minimize agitation of the media if necessary. Any of the systems described may have gas(es) delivered to the top of a system alone or in combination with delivery of one or more gases to the bottom region of a bioreactor (e.g. beneath the media). FIG. 24 illustrates a system having dual port entry 308, 2401 of one or more gases to a bioreactor where gases can be delivered simultaneously, or at differing times and concentrations to the top or bottom of a bioreactor. Regulation of flow may be accomplished by valves 302 operably connected to one or more controllers 1301, 1302, according to embodiments of the present invention.

Figure 25:
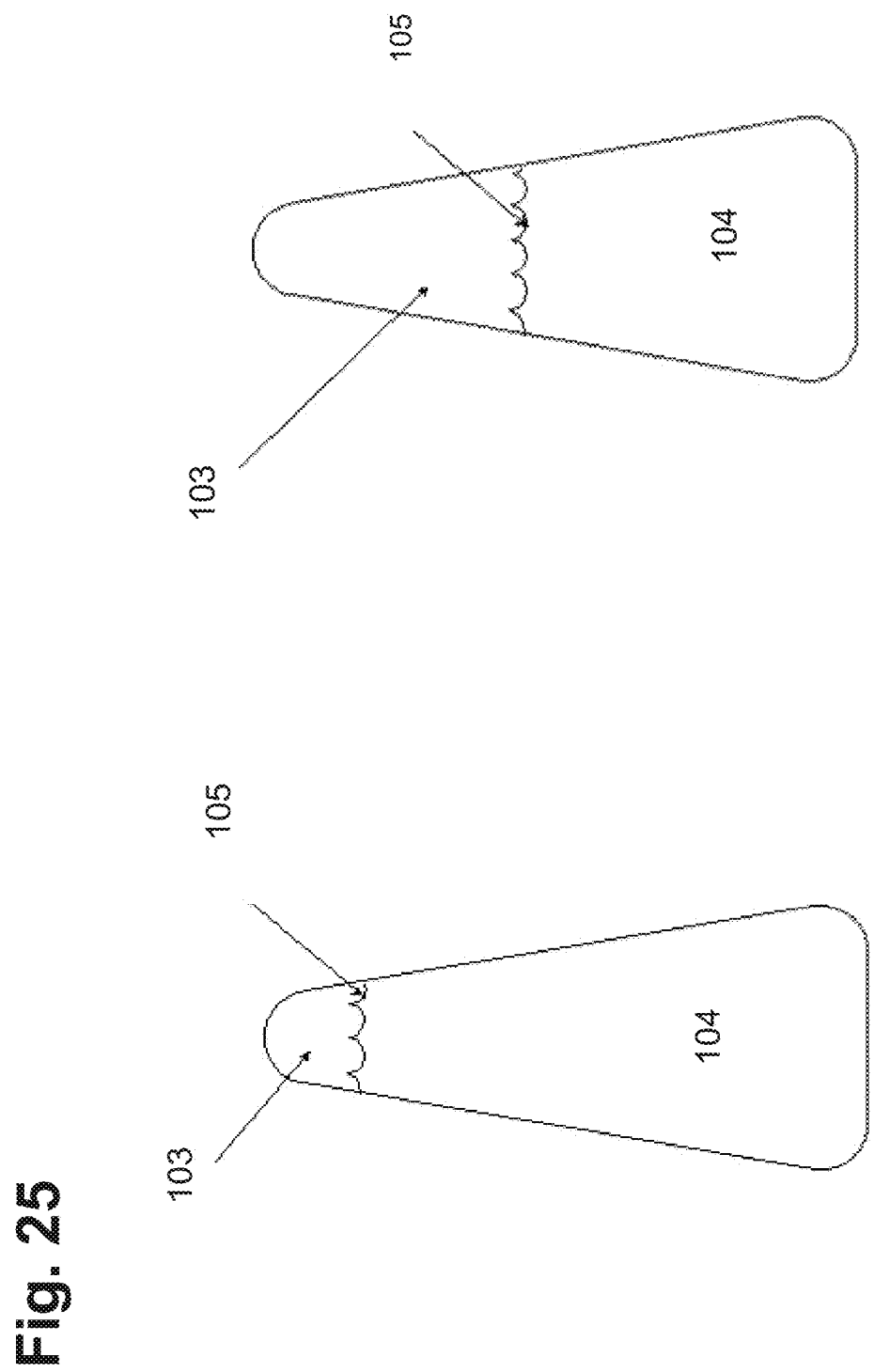
FIG. 25 illustrates cross-sectional views of photobioreactor systems having different levels of free space and culture media, according to embodiments of the present invention.

In other embodiments, surface area of a bioreactor system can be determined to control diffusion of carbon and dioxide and other gases into the media. In accordance with such embodiments, free surface areas can be varied depending on needs of a system. With any bioreactor with a non-uniform cross section, surface area can be a function of media depth. By controlling depth of the media in a bioreactor, surface area can be controlled, according to embodiments of the present invention. FIG. 25 illustrates a cross section of a roughly triangular bioreactor. As the media level 104 rises and surface area decreases, the surface to volume ratio drops. If the media level is lowered, surface area can increase and media volume decreases leading to an increase in surface area to volume.

Figure 26:
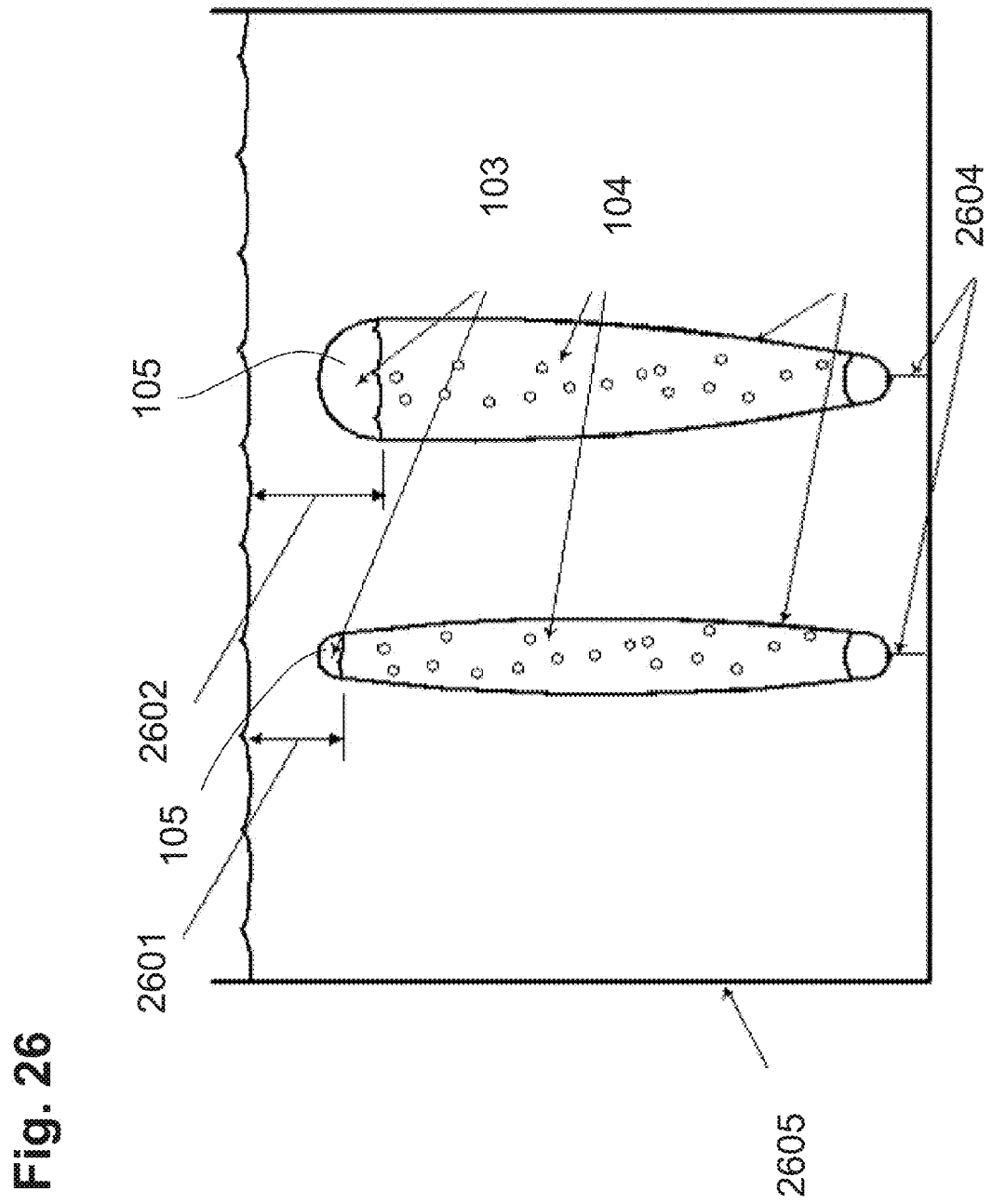
FIG. 26 illustrates cross-sectional views of two photobioreactor systems with different levels of free space, under different internal gas supply pressures, according to embodiments of the present invention.

In other embodiments, if film-based bioreactors or the like are used, pressure inside the bioreactor can be adjusted altering water level features, which can affect surface area of a media-gas interface. According to some embodiments of the present invention, the pH of the media can be controlled by controlling the pressure inside the bioreactors. FIG. 26 illustrates differences in pressure (e.g. back pressure; 2601, 2602) of two bioreactors due to submersion in a basin (e.g. thermal basin; 2605) while tethered 2604 to the bottom of the basin. As shown, the amount of gas (e.g. head space, 103) above the free surface 105 can vary due to a change in pressure. According to some embodiments of the present invention, the supply pressure of carbon dioxide and/or other gases may be varied to control the pressure within the photobioreactor 103, and thus to control the size of the gas-to-media surface area in the head space. Varying the internal pressure in this way also permits pH to be monitored and/or controlled by controlling the gas-to-media surface area in the head space to increase or decrease the diffusion rate of carbon dioxide into the media, according to embodiments of the present invention.

Figure 27:
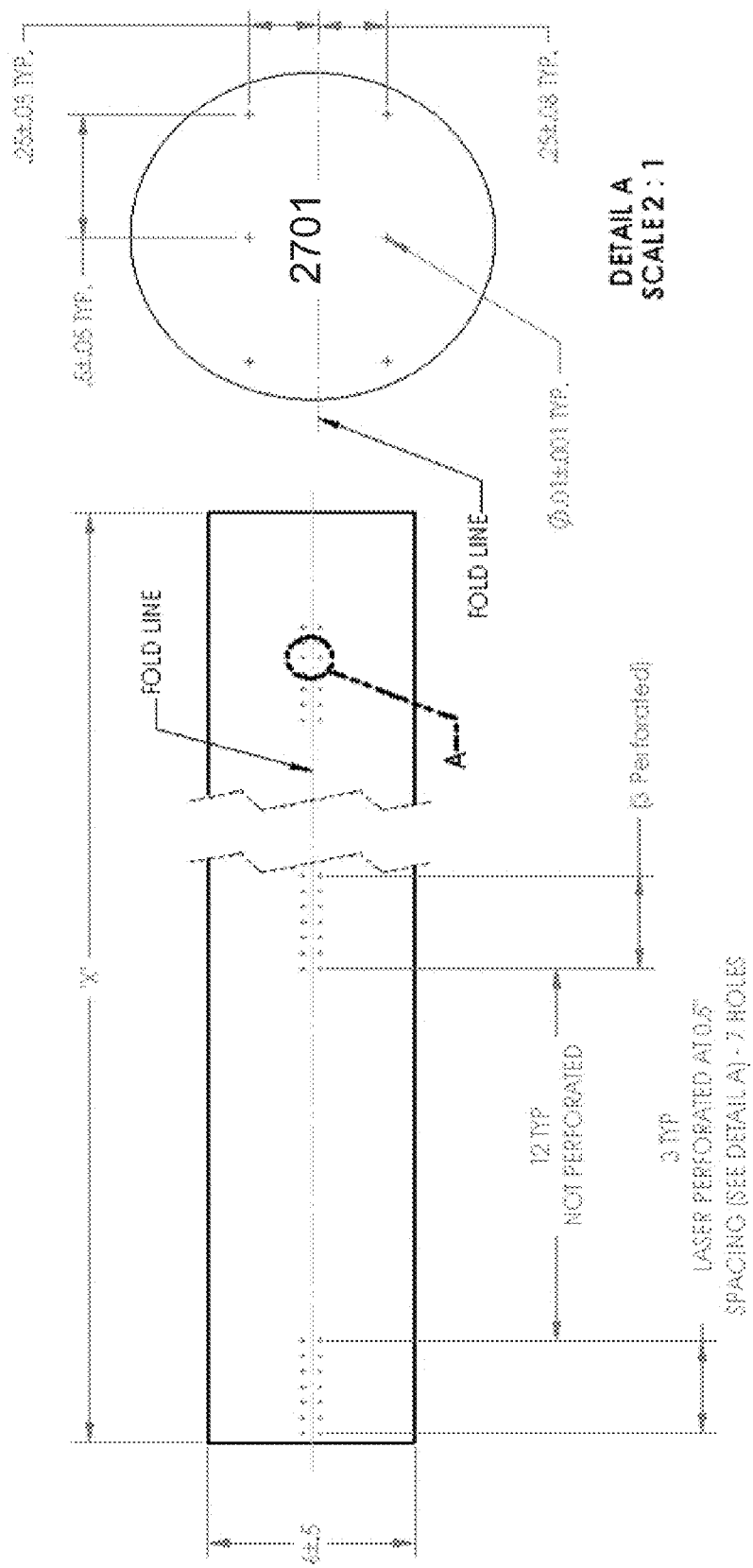
FIG. 27 illustrates perforation and assembly of a photobioreactor bag configured for intermittent gas delivery, according to embodiments of the present invention.
Figure 28:
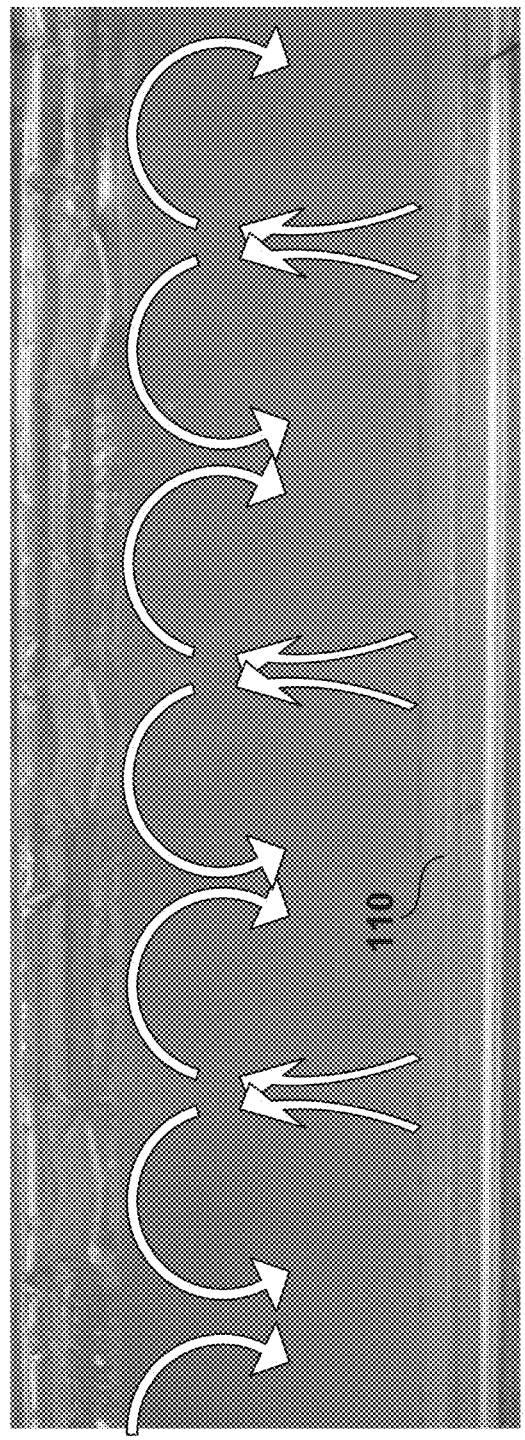
FIG. 28 illustrates fluid movement within a photobioreactor system during sparging, according to embodiments of the present invention.

According to some embodiments of the present invention, a photobioreactor provides spatially intermittent sparging with decreased flow and reduced power needs, yet produces equal or improved culturing results. In one embodiment, a bioreactor does not deliver gas or otherwise sparge along its entire length, but instead delivers gas through sets of one or more holes spaced at lengthwise intervals. FIG. 27 illustrates a print of a bubble tube 2701 used in a film based photobioreactor. The bubble tube 2701 has holes for a section (e.g. 3 inches) and then no holes (e.g. for the next 9 inches). The illustrated bubble tube 2701 pattern produces similar or better mixing than those with regularly spaced holes, with reduced gas and power needs. FIG. 28 illustrates a photograph, with convention lines superimposed thereon, of convection created in a bag using this pattern. In one experiment, sawdust was used inside of a reactor that was filled with water to illustrate the motion of the fluid. Some advantages of the spatially intermittent sparging bioreactors include: reduced power, lower operating costs, lower capital costs (at least partially due to downsizing of gas delivery equipment) and, in some systems, better mixing capabilities.

Figure 29:
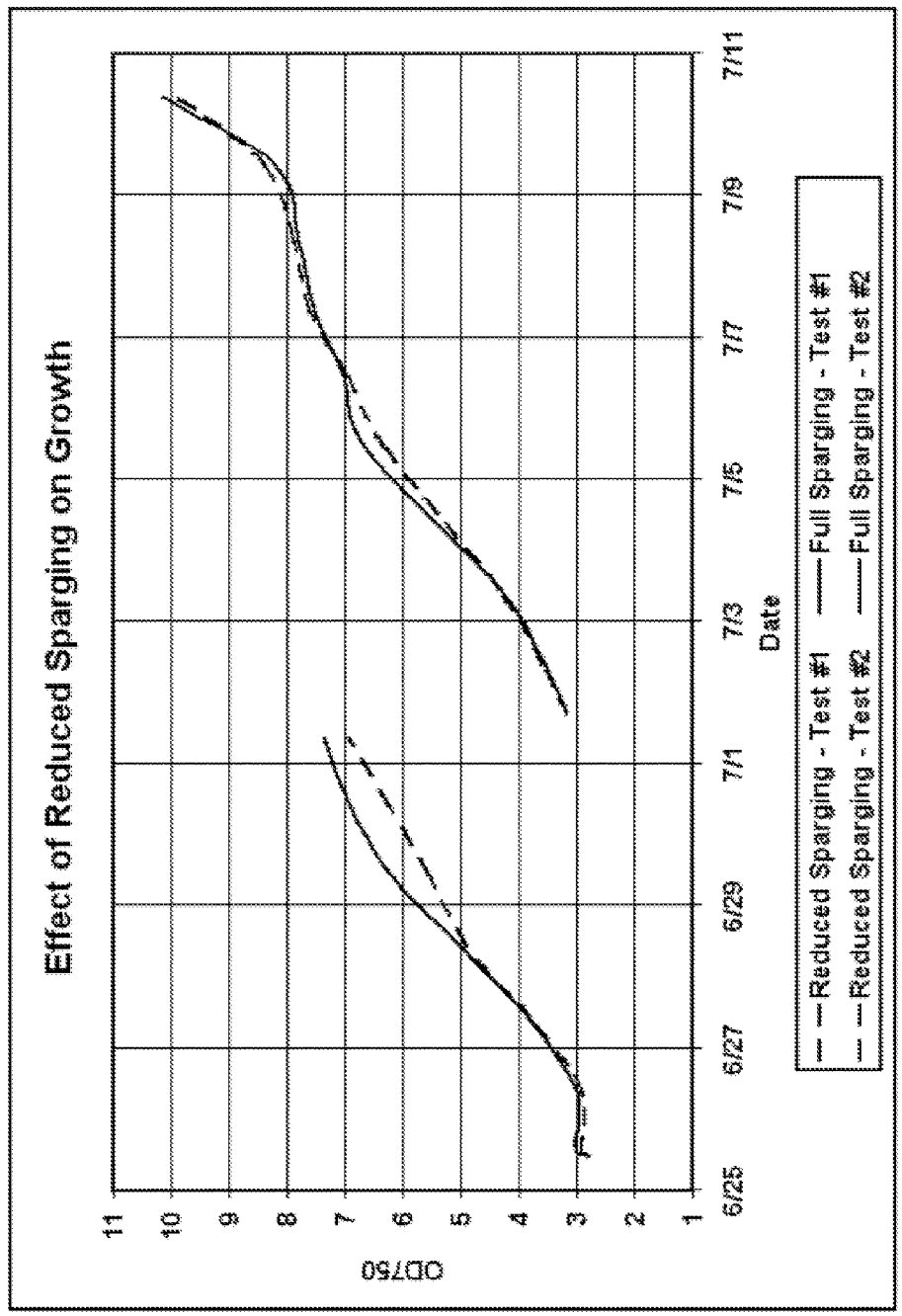
FIG. 29 depicts a plot of growth versus time illustrating the effect of reduced sparging on growth, according to embodiments of the present invention.
Figure 30:
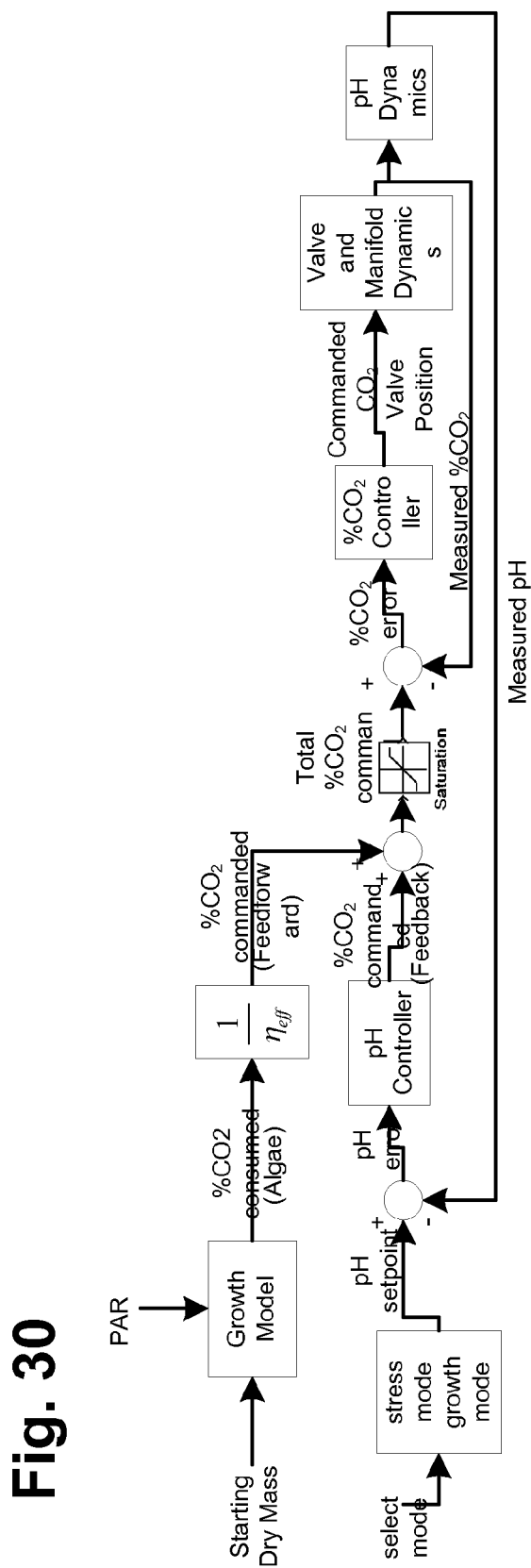
FIG. 30 illustrates a feedback and/or feedforward system for bioreactor control, according to embodiments of the present invention.

FIG. 29 illustrates experimental data in which low flow, spatially intermittently sparged bags are compared against standard hole spaced intermittently sparged bags. FIG. 29 represents a plot of various tests on growth (optical density related to time (date of observation) under varying sparging conditions, reduced sparging (dotted line) and full sparging (solid line)).

In certain embodiments of the present invention, when growing photosynthetic organisms one of the byproducts of growth is oxygen. While this can be a valuable co-product and may be captured for use, oxygen produced by the microorganisms can dissolve in media and can build up to supersaturated levels, well above those that would normally occur in the media at those conditions. High levels of dissolved oxygen can inhibit growth of photosynthetic organisms. Methods for removing dissolved oxygen from the media include, but are not limited to, adding chemicals to the media, shocking or agitating the media, pulling a vacuum or lower pressure on the media, and sparging. According to certain embodiments, sparging can be the simplest and most economical solution. For example, sparging with gases that have lower or no partial pressure of oxygen in them is even more effective than sparging with a mixture of gases that is predominantly air.

According to some embodiments of the present invention, a photobioreactor system has an open photobioreactor having a partially enclosed chamber where gases can build up and diffuse into the media. This chamber may be sized to permit distribution of carbon dioxide into the media. In some embodiments, the enclosed portion may cover most or only a part of the free surface of the media of a bioreactor.

According to one embodiments of the present invention, the size and/or cost of the hardware of a bioreactor system can be reduced by premixing atmospheric air with carbon dioxide to achieve a desired partial pressure of carbon dioxide in the gas mixture, and delivering the premixed gas to the bioreactor system. In accordance with such embodiments, gas delivery can be continuous or intermittent. If the gas delivery is intermittent, delivery can be on a fixed schedule or fixed duty cycle in which on and off times are constant. Other embodiments for gas delivery to a bioreactor include delivery of gas in which on and off times are preprogrammed as a function of time of day, days of the year, physical location of the bioreactor (e.g. altitude, latitude and/or longitude), or a combination of these parameters. In certain embodiments, such parameters can be fixed after programming, for example, a bioreactor system may be programmed years in advance so that the system does not rely on feedback or current information but can rely on predetermined parameters (e.g. parameters determined by historical data).

According to other embodiments of the present invention, a photobioreactor system is capable of receiving realtime information obtained with or without actual feedback. For example, a controller of a bioreactor system can be configured to receive weather information such as current conditions or predictions of future conditions. In certain embodiments, a constant concentration gas delivery system could use actual feedback data from local sensors for control and eventual adjustment of flow rates and/or times of delivery to a bioreactor.

In certain embodiments, a system using constant concentration of gas(es) could be used, in which the concentration of carbon dioxide is at a higher level in order to deliver a satisfactory level of carbon dioxide when demand is at its highest level. In accordance with such embodiments, an excess amount of gases can be delivered for a majority of the time. In order to compensate for the excess gases delivered to a bioreactor capture tanks can be fluidly connected to the head space of a bioreactor system for recovering exhaust gases, for example unused carbon dioxide.

According to other embodiments of the present invention, a bioreactor uses premixed gas that can be adjusted before distribution to a bioreactor. For example, carbon dioxide delivered to a system may be reduced at night (e.g. when culture growth is reduced), or gas delivery may be adjusted for seasonal changes, or local growing conditions that may include, but are not limited to, temperature, ambient lighting, and/or pressure fluctuations. As detailed previously, concentrations in premixed gas could be determined from open loop models using information gathered in advance, such as information captured from the web including, but not limited to, local weather conditions, or other information gathered from sensors, or a combination thereof.

According to yet other embodiments of the present invention, bioreactor systems deliver gases separately to a bioreactor. In such systems, the flow of air, carbon dioxide, inert gas or other gases is delivered to a bioreactor independently. Embodiments of the present invention may use a controller for determining an amount of carbon from carbon dioxide that a bioreactor needs in order to follow a command trajectory in one or more states. For example, this trajectory may be a constant value for operating a bioreactor at a constant pH (for example, at a pH of about 6.5 to about 8.0) or one pH by day and another pH by night. The details of the model based controllers used are well detailed in provisional patent application No. 61/076,103 filed Jun. 26, 2008, entitled Model Based Controls for Use with Bioreactors, incorporated herein by reference in its entirety.

In certain embodiments of the present invention, a model based controller, previously described, can be extended to include dynamics of gas/media interface such that the model can be used to determine what the composition of the gas in the head space should be in order to affect the desired carbon content (pH) of the media. In some of these embodiments, dynamics of diffusion of carbon dioxide would likely be included as a function of surface area, partial pressure of the carbon dioxide in head space of a bioreactor, equivalent partial pressure of the carbon dioxide in the media, temperature, media and gas motion, for example.

According to other embodiments of the present invention, a gas delivery system measures pH against a setpoint and determines if any correction is needed, and, if so, determines the direction and magnitude of the adjustment to gas delivery to achieve the setpoint in a bioreactor system. In one embodiment, an error may be calculated (e.g. desired pH minus measured pH) and if the absolute value of the result is greater than a predetermined amount, then correction may be initiated. If the error is less than a predetermined amount, then no corrective action is needed, and the feedback term for the carbon would be zero. If the error is greater than or equal to the predetermined amount (which may also be referred to as a "deadband"), than a need for an adjustment of the system is recognized.

In other embodiments, if absolute value of the error is too great, corrective action may be different if there is too much carbon in the media as opposed to a situation in which not enough carbon is present. If there is too much carbon (which may show up as a pH lower than desired), a decision needs to be made about whether to initiate corrective action. This is done by assessing the magnitude of the error. If the absolute value of the error is less than a certain amount, it may serve the system better by doing nothing and permitting photosynthesis to use up the carbon in an algae culture, raising the pH. If the magnitude of the error is large enough that the pH is significantly reduced, then some of the carbon may need to be removed. In order to raise the pH in such cases, a gas may be delivered to the photobioreactor chamber which is one hundred precent air followed by carbon dioxide at a predetermined later time, or a concentration of carbon dioxide in the feed gas may be reduced, according to embodiments of the present invention.

According to some embodiments of the present invention, introduction of the carbon dioxide is automated; according to other embodiments of the present invention, introduction of carbon dioxide is done manually. This correction can be done as a simple feedback solution in which the amount of carbon is proportional to the error (P controller), or based on a term proportional to the error and another term proportional to the integral of the error (PI controller). In such embodiments, a proportional controller may be used. Because there is an open loop term that accounts for the growth, this term only needs to account for the amount required to make the correction. In such embodiments, a proportional term can be determined and used. Other embodiments employ a "deadbeat"-type controller capable of calculating concentration needs to correct the error in a predefined amount of time (e.g. a one-time step). For example, one proportional term can be determined by tuning the controller while in operation. In one exemplary system, the amount of carbon required for a closed loop term can be calculated and added to an open loop term to get a total amount of carbon desired to be added to a bioreactor system.

There are many different ways that the reactor can be controlled to optimize either the carbon dioxide uptake efficiency or minimize the hardware required, durability, etc.:

Constant Concentration Premixed Gas:

In one embodiment, means from a hardware standpoint would be to premix atmospheric air with CO2 to achieve a desired partial pressure of $CO_2$ in the gas mixture and always use this gas to sparge with. The sparging could be continuous or could be intermittent. If the sparging is intermittent it could be on a fixed schedule where the duration of on and off time are constant. A slightly more complicated system might have the on and off times be a function of the time of day, a function of the day of the year, the physical location of the reactor (altitude and longitude), etc or any combination of the two or more of these. In this case all of these parameters are fixed parameters that could be programmed well in advance (years) and do not rely on any feedback or current information. An even more complicated version of this might include more current information that could be obtained without actual feedback. Examples of this might include receiving weather information that could include current conditions and might also include predictions. This constant concentration system could become even more sophisticated by using actual feedback from local sensors. Of course you could put together any combination of these above.

The limitation of this system is that a concentration of gas would need to be used that could handle the worst case $CO_2$ demand meaning that a majority of the time the concentration would be greater than what is needed and unless there are means to capture and recover the exhaust gases the use of $CO_2$ will be high. Also, by not separating the introduction of $CO_2$ from the sparging of the air, there may need to be times that $CO_2$ is added when it is not needed thus again using more $CO_2$ than needed. The advantage is that the gas could be premixed at a central point and distributed throughout the site, greatly reducing costs.

Variable Concentration Premixed Gas:

The system described above could be designed such that the concentration of the premixed gas can be adjusted in advance before it is distributed. For example the amount of $CO_2$ could be reduced at night, or adjusted for the seasons, or local growing conditions including temperature, ambient lighting, etc. As above the concentration in the premixed gas could be determined solely from open loop models using only information that can be tabled well in advance, it could use information from the web, it could use local weather conditions, it could use feedback information from sensors, and any combination of these.

Independent Air and CO2 Delivery

There could be advantages to not premixing the gases and controlling the flow of air, $CO_2$ and whatever gases to the bag independently.

One system is described in more detail here:

Determine the Amount of CO2 Needed from Growth:

The embodiment described in detail here used to control the reactor is to use model based controllers to determine ahead of time the amount of carbon that the reactor needs in order to follow a command trajectory in one or more states. This trajectory may be a constant value, for example it may be that it is desired to operate the reactor at a constant pH of 7.3 as was done in these experiments, or perhaps it is desired to have the pH remain at 7.3 and allow it to rise during the night.

The model based controller described earlier can be extended to include the dynamics of the gas/media interface such that the model can be used to determine what the composition of the gas in the headspace should be in order to affect the desired carbon content (pH) of the media. These models would likely include the dynamics of the diffusion of the carbon dioxide into the media as a function of surface area, partial pressure of the carbon dioxide in the head space, the equivalent partial pressure of the $CO_2$ in the media, temperature, media and gas motion, etc.

Determine if the pH is in Control:

The next step that happens in this embodiment is that the system compares the measure pH against a setpoint and determines if any correction is needed, and if so what is the direction and magnitude. This is done by calculating the error (desired pH—measured pH) and seeing if the absolute value of this is greater than a deadband. If it is less than the deadband than no corrective action in required and the feedback term for the carbon is zero. If the error is greater than or equal to the deadband, then a correction needs to be made.

If the pH Needs to be Corrected Determine how Much Carbon Needs to be Added or Removed:

If the absolute value of the error is too great the corrective action will be different if there is too much carbon in the media as opposed to if there is not enough. If there is too much carbon (pH lower than desired) a decision needs to be made if a correction should be made or not. This is done by assessing the magnitude of the error. If the absolute value of the error is less than a certain amount it is best to not do anything and let the photosynthesis use up the carbon raising the pH. If the magnitude of the error is large enough that the pH is dangerously low then some of the carbon needs to be removed and this will be accomplished by sparging the system with only air. There are numerous subtleties that can be done here to affect the results. Examples of this are that you could sparge with 100% air and then only add CO2 in at the very last moment. Alternatively, you could just reduce the concentration of the CO2 in the gas mixture. This would not raise the pH as fast, but would be more controllable and would minimize the danger of overshooting the desired pH. (the first case where the error is smaller than desired to be acted on can be covered by having different deadbands for positive and negative errors)

If the pH is too high then more carbon needs to be added. This correction can be done as a simple feedback problem where the amount of carbon is proportional to the error (P controller), or based on a term proportional to the error and another term proportional to the integral of the error (PI controller). In this case we use only a proportional controller. Because there is an open loop term that accounts for the growth this term is only needs to account for the amount required to make the correction. In this case a proportional term is determined and used. However, you could do this with a deadbeat type controller that calculates the required concentration to correct the error in a predefined amount of time (1 time step in the case of a deadbeat, but that is unlikely unless very long time steps are used). The proportional term we have been using was chosen by tuning the controller while it was in operation.

Find Out the Total Amount of Carbon Needed:

Once the amount of carbon required for the closed loop term has been calculated it can be added to the open loop term to get a total amount of carbon desired to be added.

Determine What the Sparging Needs to be Get that Amount of Carbon in:

Once the amount of carbon that is desired to be added to the media is calculated then an algorithm is needed that determines what the composition of the gas should look like in order to achieve that. Again, model based control would be the preferred method for this.

Reconcile with Other Demands for Sparging:

Finally, the other considerations for sparging need to be considered. Possibly the controller will determine that nothing needs to be done in order to maintain the desired pH, but sparging may be required for mixing the media. In this case the pH controller must be overridden and the sparging set to values that that satisfy both the other needs yet still maintain pH control.

Figure 31:
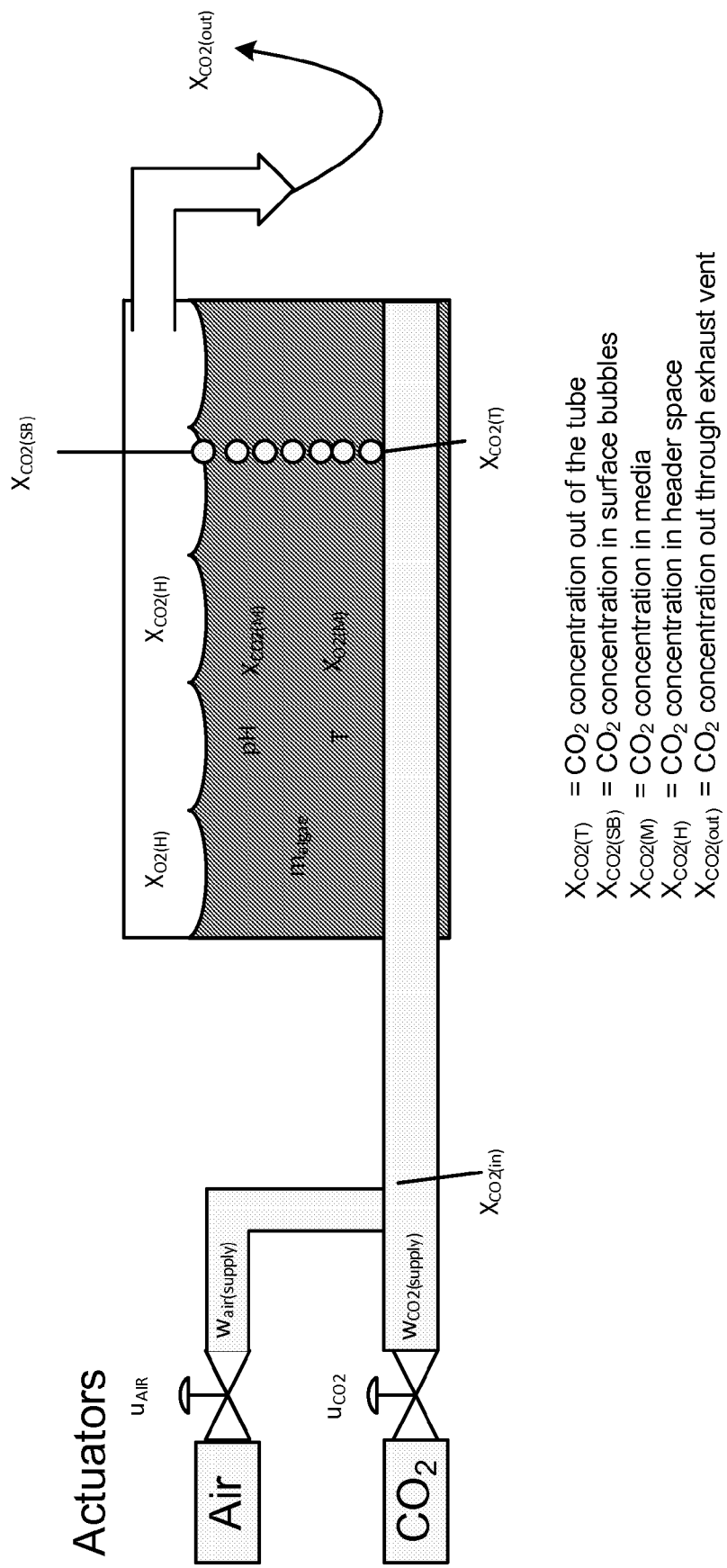
FIG. 31 illustrates a photobioreactor system, according to embodiments of the present invention.

FIG. 31 illustrates a photobioreactor system, according to embodiments of the present invention. Using a method for dynamic modeling of head space (e.g. header) concentration (not including diffusion dynamics), an assumption is made that bubbles pass through the media with no diffusion and just displace gas in the header, according to embodiments of the present invention. The rate at which this happens in determined by α, which in turn is a function of the sparge rate. The state equation for header $CO_2$ gas concentration is:

$$\frac{d}{dt}X_{CO2(H)} = \frac{w_{sparge(SLM)}}{m_{H(SL)}}(X_{CO_2(T)} - X_{CO_2(H)})$$

$$X_{CO_2(T)}(t) = X_{CO_2(in)}(t - \tau_d)$$

The variables and the values which they represent are described in FIG. 31. There is an assumed transportation delay between when the $CO_2$ concentration is changed at the source, namely $X_{CO_2(in)}$, and when it is pushed into the flat panel photobioreactor (e.g., $X_{CO_2(T)}$). This delay is represented by $\tau_d$. An example simulation where $w_{sparge}$=50 (standard liters per minute—SLM), $m_H$=50 (standard liters—SL), and $\tau_d$=0.3 (sec) is shown in FIGS. 32-34, for which the horizontal axes represent time in seconds. FIG. 32 illustrates an air flow rate using a dynamic modeling simulation for a photobioreactor having no diffusion dynamics, according to embodiments of the present invention. FIG. 33 illustrates a commanded carbon dioxide input flow rate using a dynamic modeling simulation for a photobioreactor having no diffusion dynamics, according to embodiments of the present invention. FIG. 34 illustrates a carbon dioxide header concentration using a dynamic modeling simulation for a photobioreactor having no diffusion dynamics, according to embodiments of the present invention. When the $CO_2$ MFC is turned off, the $CO_2$ concentration equals what it should in air, namely $X_{CO_2(H)}$=0.000383. Similarly, when the $CO_2$ MFC is turned on to 5 SLM, the final header concentration is $$X_{CO2(H)} = \frac{5}{55}*1 + 0.000383*\frac{50}{55} = 0.0913.$$

Another simulation may be performed to account for some diffusion dynamics between bubbles and media and between the head space surface and the media, according to embodiments of the present invention. The diffusion between the bubbles and media is assumed to be a function of the $CO_2$ concentration of the bubble at the surface, namely $X_{CO_2(SB)}$. The dynamics of the bubble gas concentration as it rises is implied by a state that models the difference between the bubble $CO_2$ concentration at the tube, namely $X_{CO_2(T)}$, and bubble $CO_2$ concentration at the surface, namely $X_{CO_2(SB)}$. The differential equations describing the gas transfer mechanisms are given by:

$$\frac{d}{dt}X_{CO_2(H)} = \alpha_{CO_2(SB \to H)}(w_{sparge})(X_{CO_2(SB)} - X_{CO_2(H)}) +$$
$$\alpha_{CO_2(M \to H)}(w_{sparge})(X_{CO_2(M)} - X_{CO_2(H)})$$

$$\frac{d}{dt}X_{CO_2(SB)} = \alpha_{CO_2(T \to SB)}(w_{sparge})(X_{CO_2(T)} - X_{CO_2(SB)}) +$$
$$\alpha_{CO_2(M \to SB)}(w_{sparge})(X_{CO_2(M)} - X_{CO_2(SB)})$$

$$\frac{d}{dt}X_{CO_2(M)} = \alpha_{CO_2(SB \to M)}(w_{sparge})(X_{CO_2(SB)} - X_{CO_2(M)}) +$$
$$\alpha_{CO_2(H \to M)}(w_{sparge})(X_{CO_2(H)} - X_{CO_2(M)}) - w_{CO_2 \text{ consumed}}$$

$$X_{CO_2(T)}(t) = X_{CO_2(in)}(t - \tau_d)$$

The last term in the equation for $$\frac{d}{dt}X_{CO_2(M)},$$

namely $w_{CO_2}$ consumed, represents the rate at which $CO_2$ (concentration) is being removed from the media due to microalgae growth, which will come from the growth model described in PCT Patent Application No. PCT/US2009/048976, filed on Jun. 26, 2009, and published as International Publication No. WO 2010/002745 A1 on Jan. 7, 2010, the contents of which are incorporated herein by reference. The values for the current simulation are given in Table 1.

TABLE 1

| Variable Name | Value |
| --- | --- |
| $\alpha_{CO_2}(SB \rightarrow H)$ | $0.15 * W_{sparge}$ |
| $\alpha_{CO_2}(M \rightarrow H) = \alpha_{CO_2}(H \rightarrow M)$ | $0.02 * W_{sparge}$ |
| $\alpha_{CO_2}(T \rightarrow SB)$ | $0.20 * W_{sparge}$ |
| $\alpha_{CO_2}(M \rightarrow SB) = \alpha_{CO_2}(SB \rightarrow M)$ | $0.04 * W_{sparge}$ |
| $\tau_d$ | $0.30 * W_{sparge}$ |
| $W_{CO_2 consumed}$ | 0 (no growth) |

Figure 35:
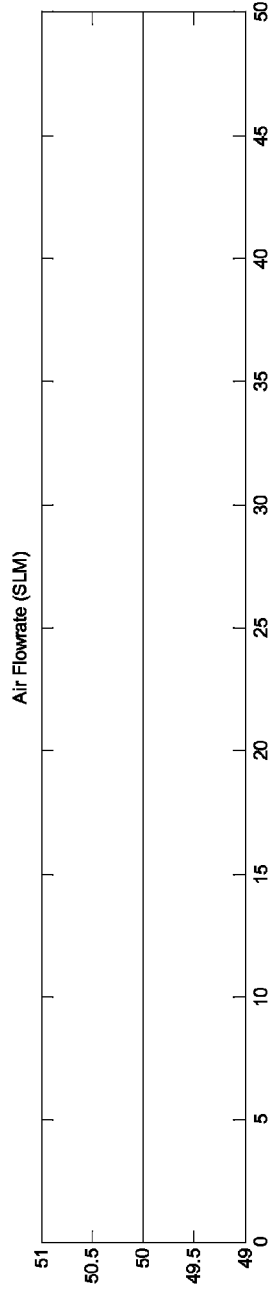
FIG. 35 illustrates an air flow rate using a dynamic modeling simulation for a photobioreactor accounting for some diffusion dynamics, according to embodiments of the present invention.
Figure 36:
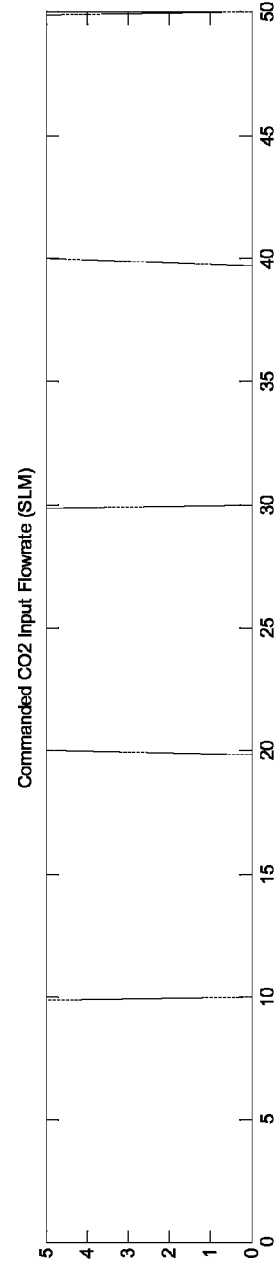
FIG. 36 illustrates a commanded carbon dioxide input flow rate using a dynamic modeling simulation for a photobioreactor accounting for some diffusion dynamics, according to embodiments of the present invention.
Figure 37:
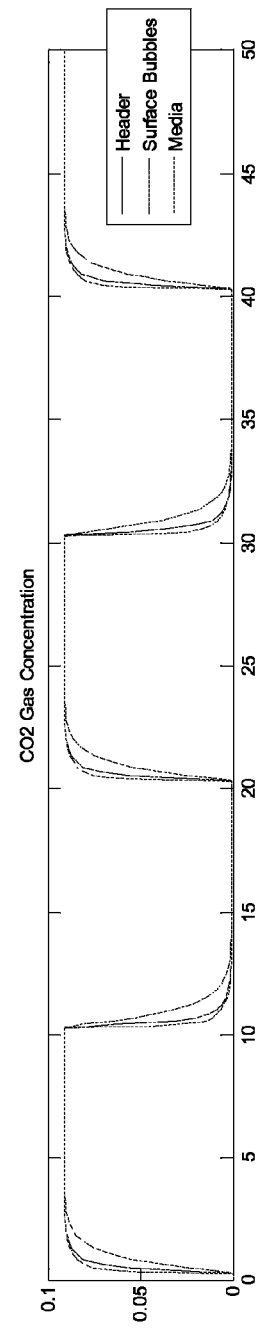
FIG. 37 illustrates a carbon dioxide header concentration using a dynamic modeling simulation for a photobioreactor accounting for some diffusion dynamics, according to embodiments of the present invention.

The resulting simulation is shown in FIGS. 35-37, for which the horizontal axes represent time in seconds. FIG. 35 illustrates an air flow rate using a dynamic modeling simulation for a photobioreactor accounting for some diffusion dynamics, according to embodiments of the present invention. FIG. 36 illustrates a commanded carbon dioxide input flow rate using a dynamic modeling simulation for a photobioreactor accounting for some diffusion dynamics, according to embodiments of the present invention. FIG. 37 illustrates a carbon dioxide header concentration using a dynamic modeling simulation for a photobioreactor accounting for some diffusion dynamics, according to embodiments of the present invention. This simulation shows that the surface bubbles and header space come to equilibrium first, respectively, which may be explained by the lack of gas-liquid diffusion. The media takes longer to come to equilibrium. These conditions are a function of the parameters in Table 1. At the time, it was hypothesized that the time for the $CO_2$ header space concentration to equal the $CO_2$ input concentration was relatively small compared to the time it took the $CO_2$ header space concentration to equal the dissolved media $CO_2$ concentration. The same equilibrium values are reached as outlined in the first method, described with respect to FIGS. 32-34, according to embodiments of the present invention.

Figure 38:
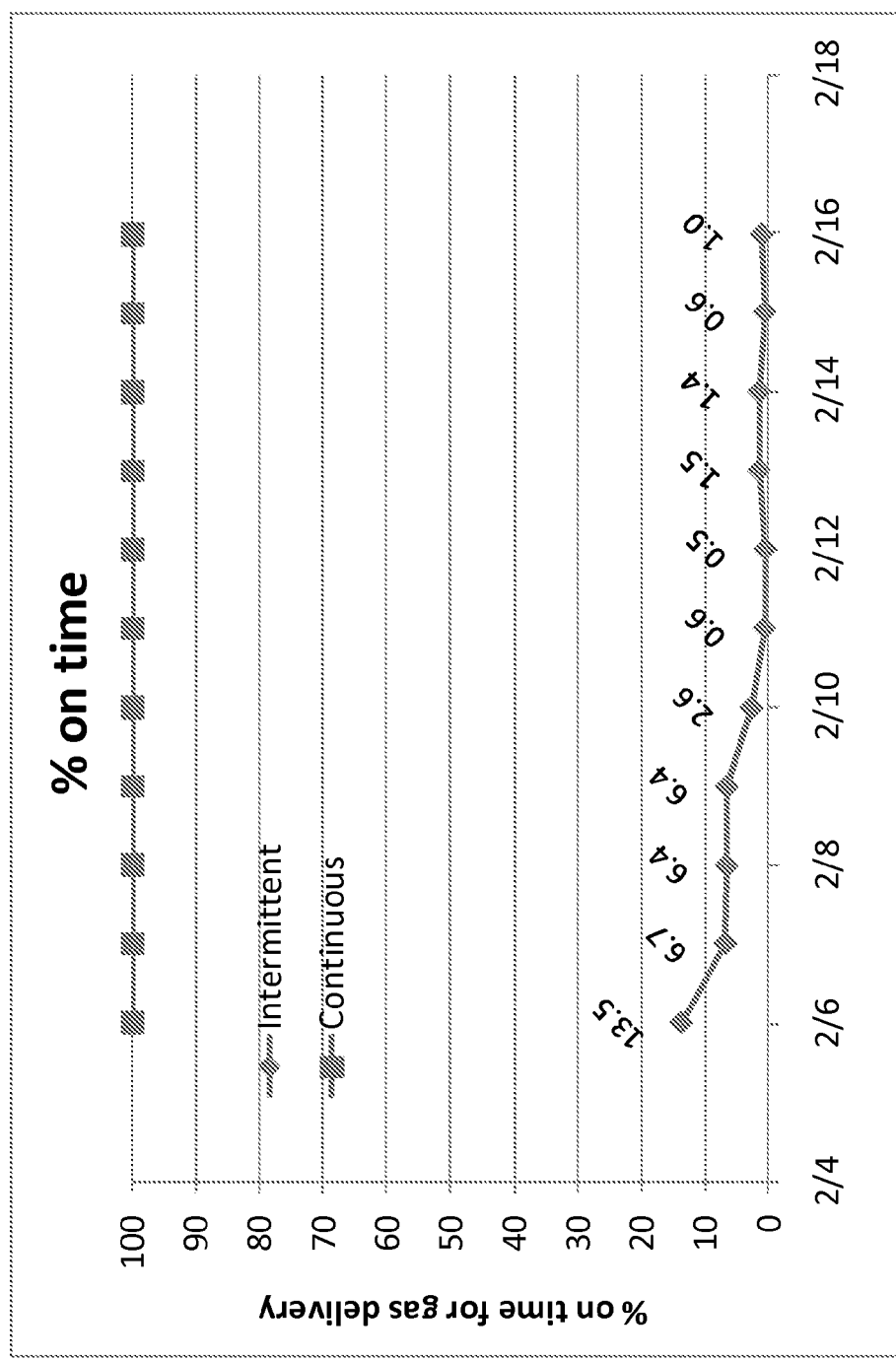
FIG. 38 depicts a plot illustrating a percentage of on time versus time for intermittent and continuous sparging, according to embodiments of the present invention.

FIGS. 38-46 illustrate experimental data involving intermittent gas delivery to a photobioreactor, according to embodiments of the present invention. FIG. 38 depicts a plot illustrating a percentage of on time versus time for intermittent and continuous sparging, according to embodiments of the present invention. FIG. 38 illustrates that intermittent sparging significantly reduces the amount of time a blower is used for sparging (e.g. as low as 0.5% of the time used for a continuous sparge, or 1% of daytime-only continuous sparge).

Figure 40:
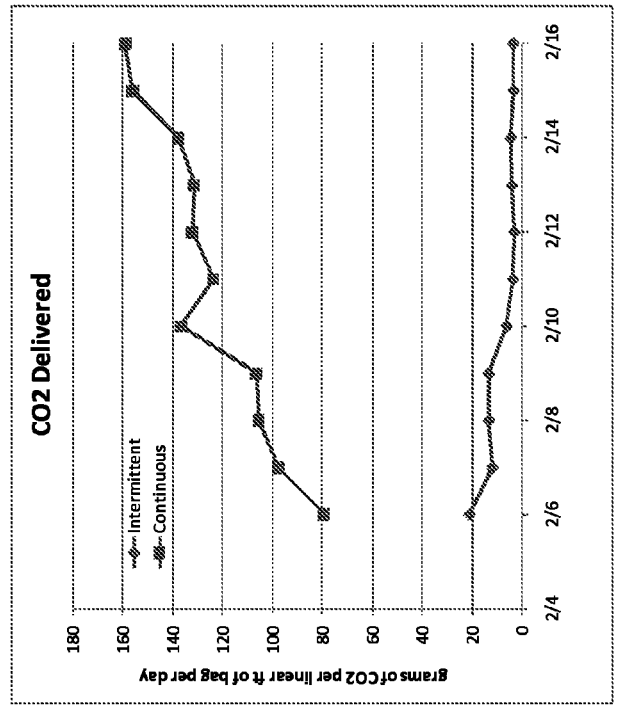
FIG. 40 depicts a plot illustrating grams of carbon dioxide delivered per linear foot of bag per day over time for intermittent and continuous sparging, according to embodiments of the present invention.
Figure 39:
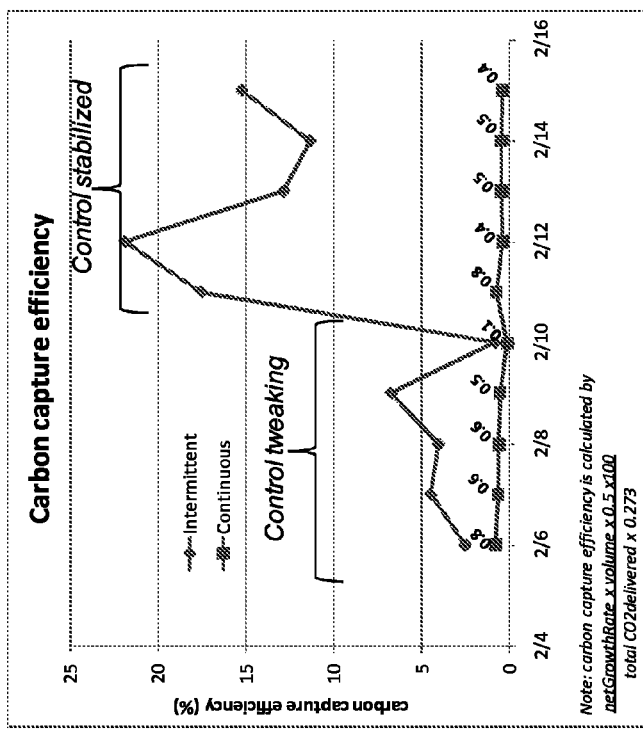
FIG. 39 depicts a plot illustrating carbon capture efficiency over time for intermittent and continuous sparging, according to embodiments of the present invention.

FIG. 39 depicts a plot illustrating carbon capture efficiency over time for intermittent and continuous sparging, according to embodiments of the present invention. FIG. 40 depicts a plot illustrating grams of carbon dioxide delivered per linear foot of bag per day over time for intermittent and continuous sparging, according to embodiments of the present invention. FIGS. 39 and 40 illustrate that intermittent sparging improves carbon dioxide use efficiency, with a carbon capture efficiency of up to twenty-two percent compared to an average of 0.5% for continuous sparging, according to embodiments of the present invention.

Figure 41:
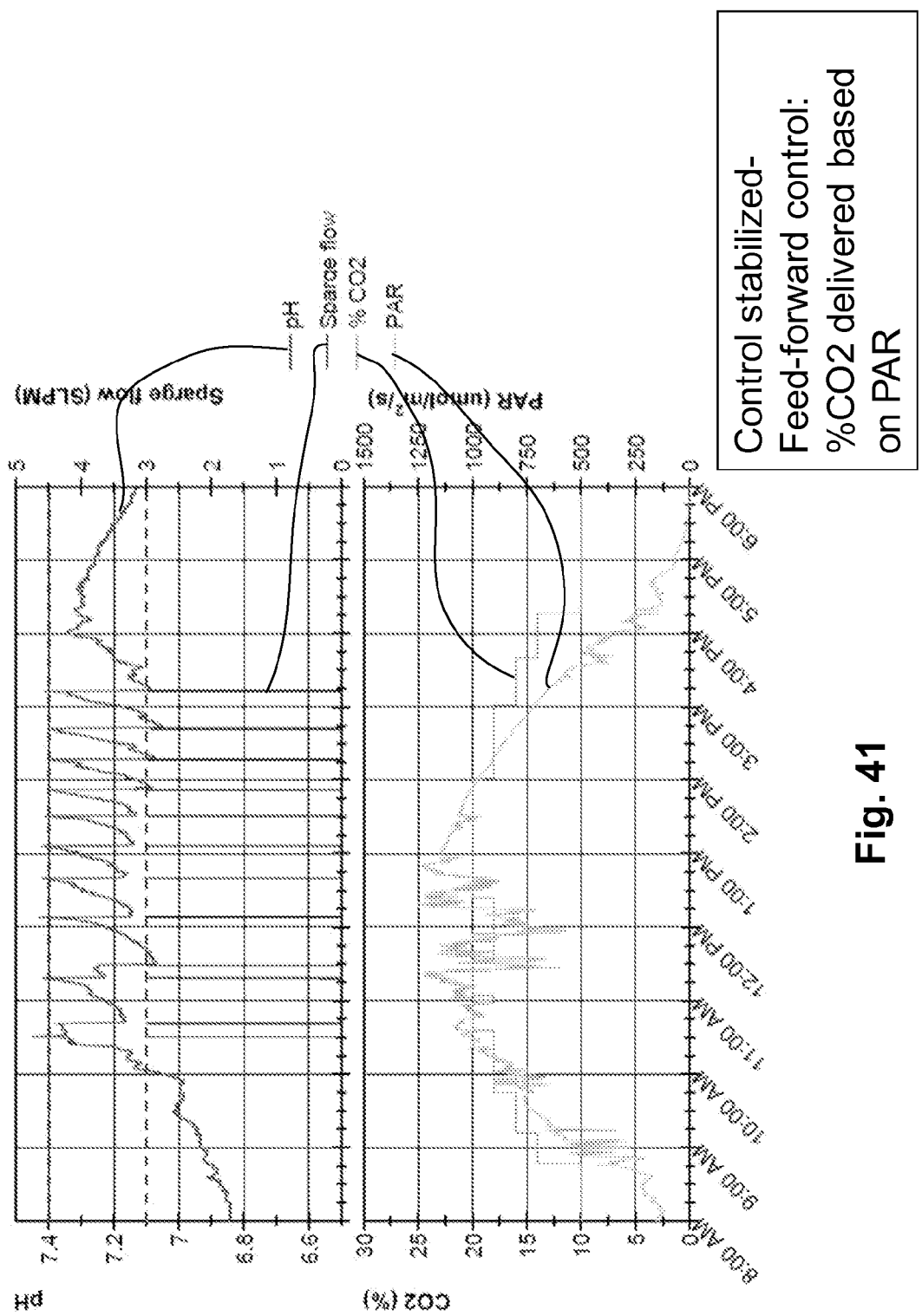
FIG. 41 depicts a plot illustrating pH and carbon dioxide percentage delivered compared with sparge flow and PAR during a daytime period, according to embodiments of the present invention.
Figure 42:
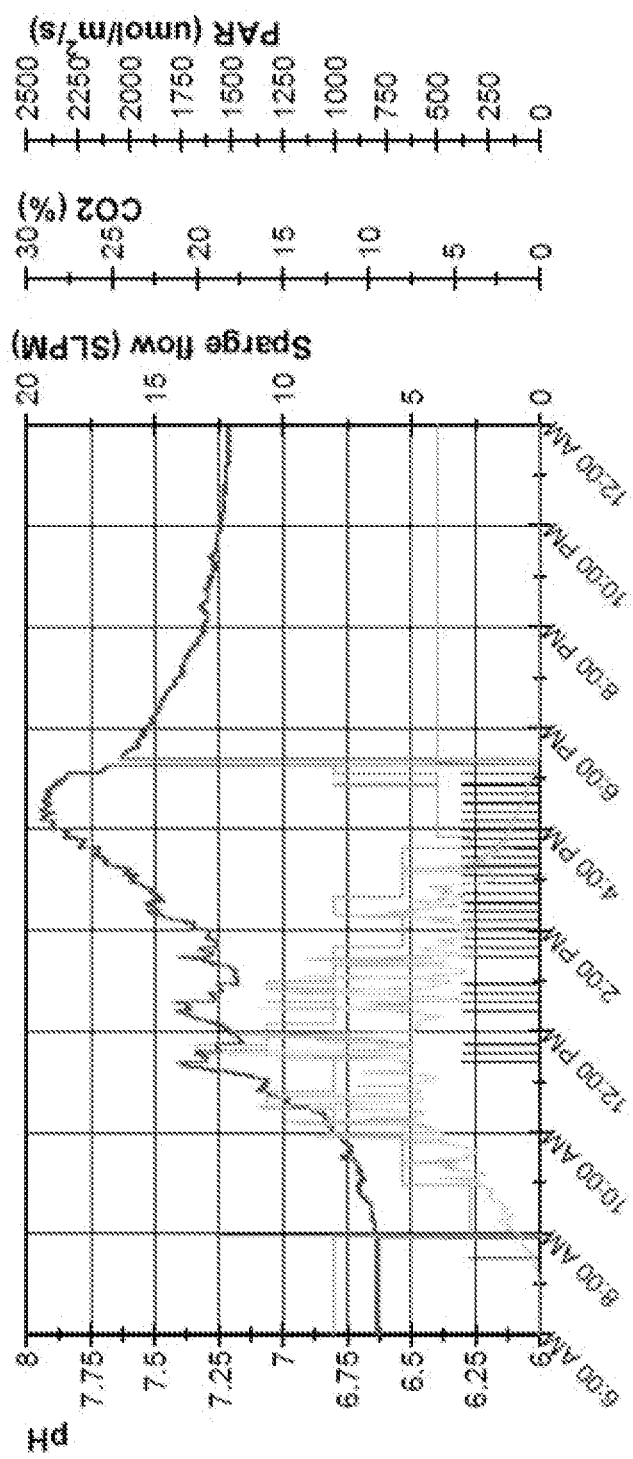
FIG. 42 depicts another plot illustrating pH and carbon dioxide percentage delivered compared with sparge flow and PAR over most of a day's time, according to embodiments of the present invention.

FIG. 41 depicts a plot illustrating pH and carbon dioxide percentage delivered compared with sparge flow and PAR during a daytime period, according to embodiments of the present invention. FIG. 41 illustrates that intermittent sparging can effectively control pH to a set range during daytime, according to embodiments of the present invention. FIG. 42 depicts another plot illustrating pH and carbon dioxide percentage delivered compared with sparge flow and PAR over most of a day's time, according to embodiments of the present invention.

Figure 43:
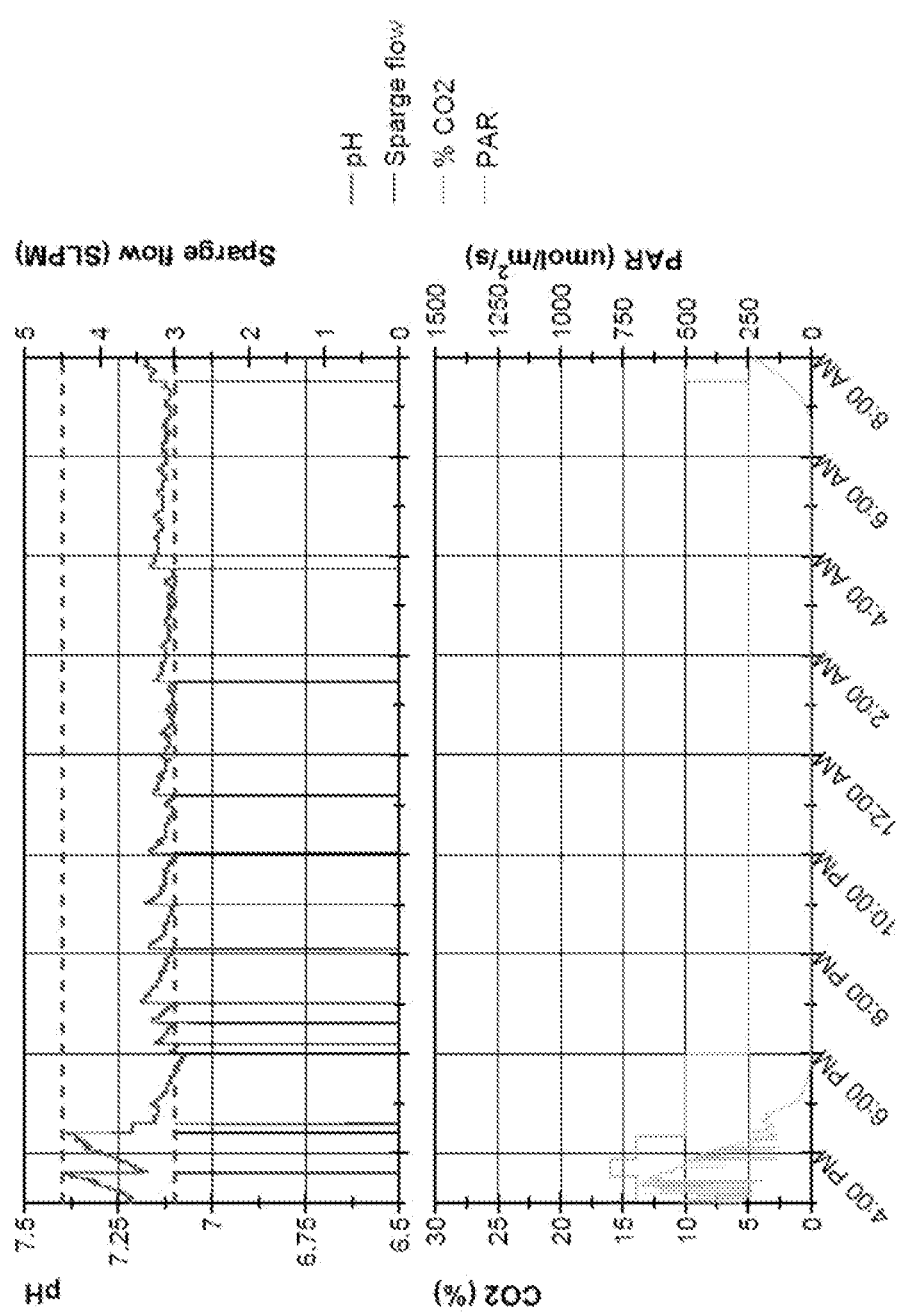
FIG. 43 depicts another plot illustrating pH and carbon dioxide percentage delivered compared with sparge flow and PAR during a nighttime period, according to embodiments of the present invention.

FIG. 43 depicts another plot illustrating pH and carbon dioxide percentage delivered compared with sparge flow and PAR during a nighttime period, according to embodiments of the present invention. FIG. 43 illustrates that intermittent sparging can effectively control pH to a set range during nighttime, according to embodiments of the present invention.

Figure 44:
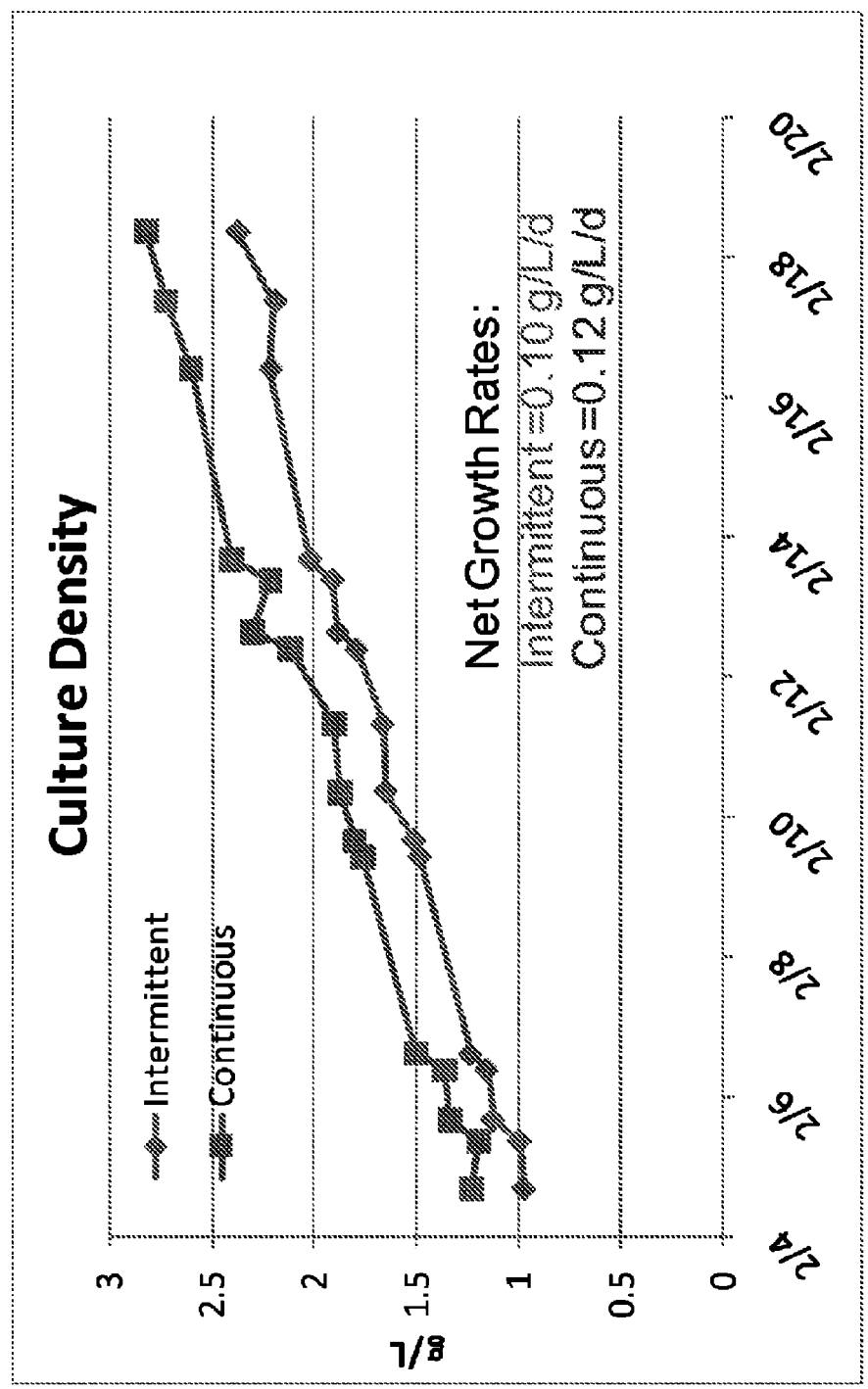
FIG. 44 depicts another plot illustrating culture density over several days comparing intermittent and continuous sparging for carbon dioxide delivery, according to embodiments of the present invention.

FIG. 44 depicts another plot illustrating culture density over several days comparing intermittent and continuous sparging for carbon dioxide delivery, according to embodiments of the present invention. FIG. 44 illustrates that intermittent sparging did not significantly decrease growth rate of the algal culture.

Figure 45:
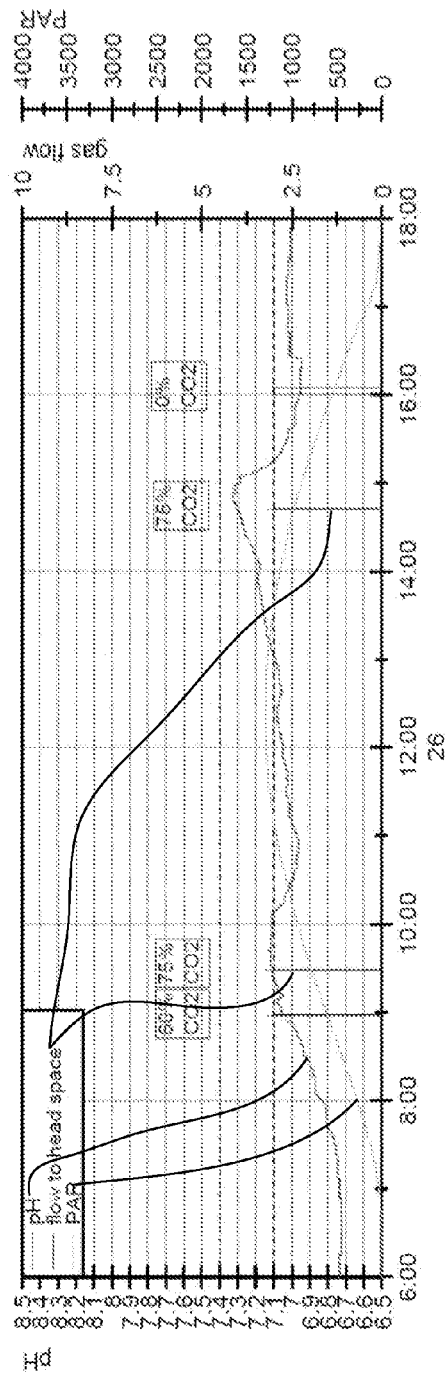
FIG. 45 depicts a plot illustrating pH, flow to head space, and PAR over a twelve hour time period during which carbon dioxide was delivered intermittently only to a head space of the photobioreactor and not sparged into the photobioreactor, according to embodiments of the present invention.
Figure 46:
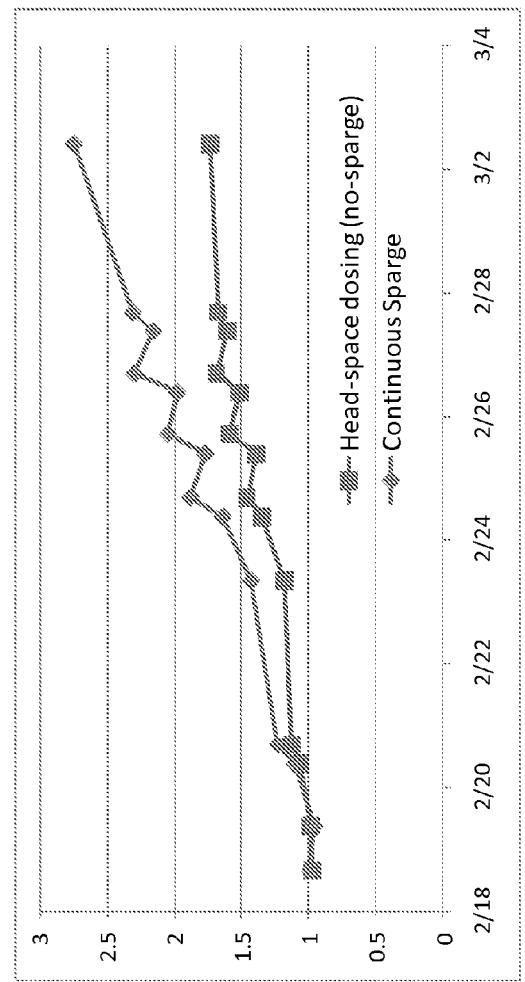
FIG. 46 depicts a plot illustrating algal culture density in grams per liter over a period of several days comparing a photobioreactor in which carbon dioxide was delivered intermittently only to a head space of the photobioreactor with a photobioreactor in which carbon dioxide was sparged continuously into the photobioreactor, according to embodiments of the present invention.

FIG. 45 depicts a plot illustrating pH, flow to head space, and PAR over a twelve hour time period during which carbon dioxide was delivered intermittently only to a head space of the photobioreactor and not sparged into the photobioreactor, according to embodiments of the present invention. FIG. 46 depicts a plot illustrating algal culture density in grams per liter over a period of eleven days comparing a photobioreactor in which carbon dioxide was delivered intermittently only to a head space of the photobioreactor with a photobioreactor in which carbon dioxide was sparged continuously into the photobioreactor, according to embodiments of the present invention. The plots of FIGS. 45 and 46 illustrate that head space direct delivery and/or dosing directly to the head space is capable of maintaining pH levels in the media during the day, with very little carbon dioxide or energy use, resulting in culture growth, according to embodiments of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method for regulating carbon dioxide introduction in a closed photobioreactor having a media, a culture of microorganisms in the media, and a head space adjacent to the media, the method comprising:
   determining a carbon dioxide deficiency in the media by determining pH of the media using a pH sensing device; and
   based on the pH of the media, delivering carbon dioxide into the photobioreactor according to a duty cycle, wherein the duty cycle consists of ON times and OFF times, wherein during the ON times a supply of carbon dioxide is delivered to the photobioreactor and at least a portion of gas already in the head space is exhausted, and wherein during the OFF times the supply of carbon dioxide is not delivered to the photobioreactor and carbon dioxide residing in the head space diffuses into the media, wherein the duty cycle is set to achieve a desired pH range, and wherein the desired pH range facilitates growth of the culture of microorganisms.

2. The method of claim 1, further comprising storing the gas from the head space after it has been exhausted from the photobioreactor.

3. The method of claim 2, further comprising reusing the stored gas from the head space by reintroducing the stored gas into the head space.

4. The method of claim 3, further comprising separating carbon dioxide from the stored gas, and wherein reintroducing the stored gas into the head space comprises reintroducing the separated carbon dioxide into the head space.

5. The method of claim 1, wherein delivering carbon dioxide into the photobioreactor comprises introducing the carbon dioxide directly into the head space.

6. The method of claim 5, further comprising agitating the media with a mechanism other than sparging.

7. The method of claim 1, wherein the carbon dioxide is a nutrient for the culture.

8. The method of claim 7, wherein the culture of microorganisms comprises algae.

9. The method of claim 7, wherein delivering carbon dioxide into the photobioreactor comprises introducing one or more gases by sparging the one or more gases into the culture of microorganisms.

10. The method of claim 9, wherein the one or more gases comprise one or more of carbon dioxide, air, and inert gas.

11. The method of claim 1, wherein determining the carbon dioxide deficiency is performed with a feedback system, and wherein the delivering of the carbon dioxide into the photobioreactor is performed with a controller system based on feedback from the feedback system.

12. The method of claim 1, wherein carbon dioxide flow rate is set based upon the desired pH range.

13. The method of claim 1, wherein flow rate and duration of carbon dioxide flow into the closed photobioreactor is based on an algorithm.

14. The method of claim 1, wherein the desired pH range is determined by a desired growth stage of the culture of microorganisms.

\* \* \* \* \*